United States Patent
Kissler et al.

(10) Patent No.: US 11,708,561 B2
(45) Date of Patent: Jul. 25, 2023

(54) PROTECTION OF BETA CELLS FROM IMMUNE ATTACK

(71) Applicant: Joslin Diabetes Center, Boston, MA (US)

(72) Inventors: Stephan Kissler, Arlington, MA (US); Peng Yi, Needham, MA (US)

(73) Assignee: Joslin Diabetes Center, Boston, MA (US)

( * ) Notice: Subject to any disclaimer, the term of this patent is extended or adjusted under 35 U.S.C. 154(b) by 582 days.

(21) Appl. No.: 16/542,721

(22) Filed: Aug. 16, 2019

(65) Prior Publication Data

US 2019/0376042 A1  Dec. 12, 2019

Related U.S. Application Data

(63) Continuation of application No. PCT/US2018/019862, filed on Feb. 27, 2018.

(60) Provisional application No. 62/464,532, filed on Feb. 28, 2017.

(51) Int. Cl.
| | |
|---|---|
| C12N 15/00 | (2006.01) |
| C12N 5/071 | (2010.01) |
| A61P 3/10 | (2006.01) |
| A61K 35/39 | (2015.01) |
| C12N 15/90 | (2006.01) |

(52) U.S. Cl.
CPC .......... *C12N 5/0676* (2013.01); *A61K 35/39* (2013.01); *A61P 3/10* (2018.01); *C12N 15/907* (2013.01); *C12N 2310/20* (2017.05); *C12N 2510/00* (2013.01); *C12N 2800/80* (2013.01)

(58) Field of Classification Search
CPC ... C12N 15/00; C12N 2510/00; C12N 5/0676
See application file for complete search history.

(56) References Cited

U.S. PATENT DOCUMENTS

2013/0023491 A1   1/2013   Annes et al.

FOREIGN PATENT DOCUMENTS

| WO | 2009045403 A2 | 4/2009 |
| WO | 2016040330 A1 | 3/2016 |

OTHER PUBLICATIONS

Guo et al. (Mar. 2016) "Inhibition of renalase expression and signaling has antitumor activity in pancreatic cancer" Scientific reports, 6(1), 1-10. (Year: 2016).*
Moede et al. (2020) "Alpha cell regulation of beta cell function" Diabetologia, 63(10), 2064-2075. (Year: 2020).*
Howson et al. (2012) "Evidence of gene-gene interaction and age-at-diagnosis effects in type 1 diabetes" Diabetes, 61(11), 3012-3017. (Year: 2012).*
Li et al. (2014) "Renalase, a new secretory enzyme: Its role in hypertensive-ischemic cardiovascular diseases" Medical Science Monitor: international medical journal of experimental and clinical research, 20, 688. (Year: 2014).*
Steinfeld et al. (Mar. 2016) "Mutations in HIVEP2 are associated with developmental delay, intellectual disability, and dysmorphic features" Neurogenetics, 17(3), 159-164. (Year: 2016).*
Addgene, "Mouse CRISPR Knockout Pooled Library (GeCKO v2)", webpage: www.addgene.org/pooled-library/zhang-mouse-gecko-v2/, accessed: Jun. 3, 2022, library published: Mar. 9, 2015. (Year: 2015).*
Sanjana et al. (2014) "Improved vectors and genome-wide libraries for CRISPR screening" Nature methods, 11(8), 783-784. (Year: 2014).*
Brorsson et al. "Genetic Risk Score Modelling for Disease Progression in New-Onset Type 1 Diabetes Patients: Increased Genetic Load of Islet-Expressed and Cytokine-Regulated Candidate Genes Predicts Poorer Glycemic Control" Journal of Diabetes Research, vol. 2016, Article ID 9570424, 8 pages. (Year: 2016).*
Ariyachet C et al., "Reprogrammed Stomach Tissue as a Renewable Source of Functional β Cells for Blood Glucose Regulation" Cell Stem Cell 18(3):410-21 (2016).
Hamaguchi, K et al., "NIT-1, a pancreatic beta-cell line established from a transgenic NOD/Lt mouse" Diabetes 40:842-9 (1991).
International Search Report and Written Opinion for PCT/US2018/019862 dated Jul. 9, 2018.
Kroon, E. et al., "Pancreatic endoderm derived from human embryonic stem cells generates glucose-responsive insulin-secreting cells in vivo" Nature Biotech 26(4):443-452 (2008).
Mosmann T, "Rapid colorimetric assay for cellular growth and survival: application to proliferation and cytotoxicity assays" J Immunol Methods 65(1-2):55-63 (1983).
Pagliuca et al., "Generation of functional human pancreatic β cells in vitro" Cell 159:428-439 (2014).
Pearson, JA et al., "The importance of the Non Obese Diabetic (NOD) mouse model in autoimmune diabetes" J Autoimmun. 66:76-88 (2016).
Podkowa, K et al., "Group II mGlu receptor antagonist LY341495 enhances the antidepressant-like effects of ketamine in the forced swim test in rats" Psychopharmacology (Berl) 233(15-16):2901-14 (2016).
Rezania, A. et al., "Reversal of diabetes with insulin-producing cells derived in vitro from human pluripotent stem cells" Nature Biotech 32(11): 1121-1133 (2014).
Xie, M et al., "β-cell-mimetic designer cells provide closed-loop glycemic control" Science 354(6317):1296-1301 (2016).
Zhou, Q. et al., "In vivo reprogramming of adult pancreatic exocrine cells to beta-cells" Nature 455:627-633 (2008).

(Continued)

*Primary Examiner* — James D Schultz
*Assistant Examiner* — James Joseph Graber
(74) *Attorney, Agent, or Firm* — McNeill Baur PLLC

(57) ABSTRACT

Compositions of genetically modified beta-like cells are encompassed. Also encompassed are methods of treatment of type 1 diabetes using these compositions or compositions that inhibit the function of the identified genes.

9 Claims, 12 Drawing Sheets

Specification includes a Sequence Listing.

(56) References Cited

OTHER PUBLICATIONS

Ben-Othman, N et al., "Long-Term GABA Administration Induces Alpha Cell-Mediated Beta-like Cell Neogenesis" Cell 168(1-2):73-85 (Jan. 12, 2017).
Li et al, "Artemisinins Target GABAA Receptor Signaling and Impair α Cell Identity" Cell 168:86-100 (Jan. 12, 2017).
Morita, S. et al. "Targeting ABL-IRE1α Signaling Spares ER-Stressed Pancreatic β Cells to Reverse Autoimmune Diabetes" Cell Metabolism; 25(4):883-897 (Apr. 4, 2017).

* cited by examiner gene locus

*gRNA targeting site*

SEQUENCE LISTING

```
<160> NUMBER OF SEQ ID NOS: 61

<210> SEQ ID NO 1
<211> LENGTH: 615
<212> TYPE: PRT
<213> ORGANISM: Homo sapiens

<400> SEQUENCE: 1

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
            100                 105                 110

Ser Ser Arg Glu Leu Val Lys Lys Val Ser Asp Val Ile Trp Asn Ser
        115                 120                 125

Leu Ser Arg Ser Tyr Phe Lys Asp Arg Ala His Ile Gln Ser Leu Phe
    130                 135                 140

Ser Phe Ile Thr Gly Trp Ser Pro Val Gly Thr Lys Leu Asp Ser Ser
145                 150                 155                 160
```

```
Gly Val Ala Phe Ala Val Val Gly Ala Cys Gln Ala Leu Gly Leu Arg
                165                 170                 175

Asp Val His Leu Ala Leu Ser Glu Asp His Ala Trp Val Val Phe Gly
            180                 185                 190

Pro Asn Gly Glu Gln Thr Ala Glu Val Thr Trp His Gly Lys Gly Asn
        195                 200                 205

Glu Asp Arg Arg Gly Gln Thr Val Asn Ala Gly Val Ala Glu Arg Ser
    210                 215                 220

Trp Leu Tyr Leu Lys Gly Ser Tyr Met Arg Cys Asp Arg Lys Met Glu
225                 230                 235                 240

Val Ala Phe Met Val Cys Ala Ile Asn Pro Ser Ile Asp Leu His Thr
                245                 250                 255

Asp Ser Leu Glu Leu Leu Gln Leu Gln Gln Lys Leu Leu Trp Leu Leu
            260                 265                 270

Tyr Asp Leu Gly His Leu Glu Arg Tyr Pro Met Ala Leu Gly Asn Leu
        275                 280                 285

Ala Asp Leu Glu Glu Leu Glu Pro Thr Pro Gly Arg Pro Asp Pro Leu
    290                 295                 300

Thr Leu Tyr His Lys Gly Ile Ala Ser Ala Lys Thr Tyr Tyr Arg Asp
305                 310                 315                 320

Glu His Ile Tyr Pro Tyr Met Tyr Leu Ala Gly Tyr His Cys Arg Asn
                325                 330                 335

Arg Asn Val Arg Glu Ala Leu Gln Ala Trp Ala Asp Thr Ala Thr Val
            340                 345                 350

Ile Gln Asp Tyr Asn Tyr Cys Arg Glu Asp Glu Ile Tyr Lys Glu
        355                 360                 365

Phe Phe Glu Val Ala Asn Asp Val Ile Pro Asn Leu Leu Lys Glu Ala
    370                 375                 380

Ala Ser Leu Leu Glu Ala Gly Glu Glu Arg Pro Gly Glu Gln Ser Gln
385                 390                 395                 400

Gly Thr Gln Ser Gln Gly Ser Ala Leu Gln Asp Pro Glu Cys Phe Ala
                405                 410                 415

His Leu Leu Arg Phe Tyr Asp Gly Ile Cys Lys Trp Glu Glu Gly Ser
            420                 425                 430

Pro Thr Pro Val Leu His Val Gly Trp Ala Thr Phe Leu Val Gln Ser
        435                 440                 445

Leu Gly Arg Phe Glu Gly Gln Val Arg Gln Lys Val Arg Ile Val Ser
    450                 455                 460

Arg Glu Ala Glu Ala Glu Ala Glu Glu Pro Trp Gly Glu Glu Ala
465                 470                 475                 480

Arg Glu Gly Arg Arg Gly Pro Arg Glu Ser Lys Pro Glu Glu
                485                 490                 495

Pro Pro Pro Pro Lys Lys Pro Ala Leu Asp Lys Gly Leu Gly Thr Gly
            500                 505                 510

Gln Gly Ala Val Ser Gly Pro Pro Arg Lys Pro Pro Gly Thr Val Ala
        515                 520                 525

Gly Thr Ala Arg Gly Pro Glu Gly Gly Ser Thr Ala Gln Val Pro Ala
    530                 535                 540

Pro Thr Ala Ser Pro Pro Glu Gly Pro Val Leu Thr Phe Gln Ser
545                 550                 555                 560

Glu Lys Met Lys Gly Met Lys Glu Leu Leu Val Ala Thr Lys Ile Asn
                565                 570                 575
```

```
Ser Ser Ala Ile Lys Leu Gln Leu Thr Ala Gln Ser Gln Val Gln Met
            580                 585                 590

Lys Lys Gln Lys Val Ser Thr Pro Ser Asp Tyr Thr Leu Ser Phe Leu
    595                 600                 605

Lys Arg Gln Arg Lys Gly Leu
    610                 615

<210> SEQ ID NO 2
<211> LENGTH: 2446
<212> TYPE: PRT
<213> ORGANISM: Homo sapiens

<400> SEQUENCE: 2

Met Asp Thr Gly Asp Thr Ala Leu Gly Gln Lys Ala Thr Ser Arg Ser
1               5                   10                  15

Gly Glu Thr Asp Lys Ala Ser Gly Arg Trp Arg Gln Glu Gln Ser Ala
            20                  25                  30

Val Ile Lys Met Ser Thr Phe Gly Ser His Glu Gly Gln Arg Gln Pro
        35                  40                  45

Gln Ile Glu Pro Glu Gln Ile Gly Asn Thr Ala Ser Ala Gln Leu Phe
    50                  55                  60

Gly Ser Gly Lys Leu Ala Ser Pro Ser Glu Val Val Gln Val Ala
65                  70                  75                  80

Glu Lys Gln Tyr Pro Pro His Arg Pro Ser Pro Tyr Ser Cys Gln His
                85                  90                  95

Ser Leu Ser Phe Pro Gln His Ser Leu Pro Gln Gly Val Met His Ser
            100                 105                 110

Thr Lys Pro His Gln Ser Leu Glu Gly Pro Pro Trp Leu Phe Pro Gly
        115                 120                 125

Pro Leu Pro Ser Val Ala Ser Glu Asp Leu Phe Pro Phe Pro Ile His
    130                 135                 140

Gly His Ser Gly Gly Tyr Pro Arg Lys Lys Ile Ser Ser Leu Asn Pro
145                 150                 155                 160

Ala Tyr Ser Gln Tyr Ser Gln Lys Ser Ile Glu Gln Ala Glu Ala
                165                 170                 175

His Lys Lys Glu His Lys Pro Lys Lys Pro Gly Lys Tyr Ile Cys Pro
            180                 185                 190

Tyr Cys Ser Arg Ala Cys Ala Lys Pro Ser Val Leu Lys Lys His Ile
        195                 200                 205

Arg Ser His Thr Gly Glu Arg Pro Tyr Pro Cys Ile Pro Cys Gly Phe
    210                 215                 220

Ser Phe Lys Thr Lys Ser Asn Leu Tyr Lys His Arg Lys Ser His Ala
225                 230                 235                 240

His Ala Ile Lys Ala Gly Leu Val Pro Phe Thr Glu Ser Ala Val Ser
                245                 250                 255

Lys Leu Asp Leu Glu Ala Gly Phe Ile Asp Val Glu Ala Glu Ile His
            260                 265                 270

Ser Asp Gly Glu Gln Ser Thr Asp Thr Asp Glu Glu Ser Ser Leu Phe
        275                 280                 285

Ala Glu Ala Ser Asp Lys Met Ser Pro Gly Pro Ile Pro Leu Asp
    290                 295                 300

Ile Ala Ser Arg Gly Gly Tyr His Gly Ser Leu Glu Glu Ser Leu Gly
305                 310                 315                 320

Gly Pro Met Lys Val Pro Ile Leu Ile Ile Pro Lys Ser Gly Ile Pro
                325                 330                 335
```

```
Leu Pro Asn Glu Ser Ser Gln Tyr Ile Gly Pro Asp Met Leu Pro Asn
            340                 345                 350

Pro Ser Leu Asn Thr Lys Ala Asp Ser His Thr Val Lys Gln Lys
        355                 360                 365

Leu Ala Leu Arg Leu Ser Glu Lys Lys Gly Gln Asp Ser Glu Pro Ser
370                 375                 380

Leu Asn Leu Leu Ser Pro His Ser Lys Gly Ser Thr Asp Ser Gly Tyr
385                 390                 395                 400

Phe Ser Arg Ser Glu Ser Ala Glu Gln Gln Ile Ser Pro Pro Asn Thr
                405                 410                 415

Asn Ala Lys Ser Tyr Glu Glu Ile Ile Phe Gly Lys Tyr Cys Arg Leu
            420                 425                 430

Ser Pro Arg Asn Ala Leu Ser Val Thr Thr Thr Ser Gln Glu Arg Ala
        435                 440                 445

Ala Met Gly Arg Lys Gly Ile Met Glu Pro Leu Pro His Val Asn Thr
    450                 455                 460

Arg Leu Asp Val Lys Met Phe Glu Asp Pro Val Ser Gln Leu Ile Pro
465                 470                 475                 480

Ser Lys Gly Asp Val Asp Pro Ser Gln Thr Ser Met Leu Lys Ser Thr
                485                 490                 495

Lys Phe Asn Ser Glu Ser Arg Gln Pro Gln Ile Ile Pro Ser Ser Ile
            500                 505                 510

Arg Asn Glu Gly Lys Leu Tyr Pro Ala Asn Phe Gln Gly Ser Asn Pro
        515                 520                 525

Val Leu Leu Glu Ala Pro Val Asp Ser Ser Pro Leu Ile Arg Ser Asn
    530                 535                 540

Ser Val Pro Thr Ser Ser Ala Thr Asn Leu Thr Ile Pro Pro Ser Leu
545                 550                 555                 560

Arg Gly Ser His Ser Phe Asp Glu Arg Met Thr Gly Ser Asp Asp Val
                565                 570                 575

Phe Tyr Pro Gly Thr Val Gly Ile Pro Pro Gln Arg Met Leu Arg Arg
            580                 585                 590

Gln Ala Ala Phe Glu Leu Pro Ser Val Gln Glu Gly His Val Glu Val
        595                 600                 605

Glu His His Gly Arg Met Leu Lys Gly Ile Ser Ser Ser Ser Leu Lys
    610                 615                 620

Glu Lys Lys Leu Ser Pro Gly Asp Arg Val Gly Tyr Asp Tyr Asp Val
625                 630                 635                 640

Cys Arg Lys Pro Tyr Lys Lys Trp Glu Asp Ser Glu Thr Pro Lys Gln
                645                 650                 655

Asn Tyr Arg Asp Ile Ser Cys Leu Ser Ser Leu Lys His Gly Gly Glu
            660                 665                 670

Tyr Phe Met Asp Pro Val Val Pro Leu Gln Gly Val Pro Ser Met Phe
        675                 680                 685

Gly Thr Thr Cys Glu Asn Arg Lys Arg Lys Glu Lys Ser Val Gly
    690                 695                 700

Asp Glu Glu Asp Thr Pro Met Ile Cys Ser Ser Ile Val Ser Thr Pro
705                 710                 715                 720

Val Gly Ile Met Ala Ser Asp Tyr Asp Pro Lys Leu Gln Met Gln Glu
                725                 730                 735

Gly Val Arg Ser Gly Phe Ala Met Ala Gly His Glu Asn Leu Ser His
            740                 745                 750
```

```
Gly His Thr Glu Arg Phe Asp Pro Cys Arg Pro Gln Leu Gln Pro Gly
        755                 760                 765

Ser Pro Ser Leu Val Ser Glu Glu Ser Pro Ser Ala Ile Asp Ser Asp
770                 775                 780

Lys Met Ser Asp Leu Gly Gly Arg Lys Pro Pro Gly Asn Val Ile Ser
785                 790                 795                 800

Val Ile Gln His Thr Asn Ser Leu Ser Arg Pro Asn Ser Phe Glu Arg
                805                 810                 815

Ser Glu Ser Ala Glu Leu Val Ala Cys Thr Gln Asp Lys Ala Pro Ser
            820                 825                 830

Pro Ser Glu Thr Cys Asp Ser Glu Ile Ser Glu Ala Pro Val Ser Pro
        835                 840                 845

Glu Trp Ala Pro Pro Gly Asp Gly Ala Glu Ser Gly Gly Lys Pro Ser
    850                 855                 860

Pro Ser Gln Gln Val Gln Gln Ser Tyr His Thr Gln Pro Arg Leu
865                 870                 875                 880

Val Arg Gln His Asn Ile Gln Val Pro Glu Ile Arg Val Thr Glu Glu
                885                 890                 895

Pro Asp Lys Pro Glu Lys Glu Lys Glu Ala Gln Ser Lys Glu Pro Glu
            900                 905                 910

Lys Pro Val Glu Glu Phe Gln Trp Pro Gln Arg Ser Glu Thr Leu Ser
        915                 920                 925

Gln Leu Pro Ala Glu Lys Leu Pro Pro Lys Lys Lys Arg Leu Arg Leu
    930                 935                 940

Ala Asp Met Glu His Ser Ser Gly Glu Ser Ser Phe Glu Ser Thr Gly
945                 950                 955                 960

Thr Gly Leu Ser Arg Ser Pro Ser Gln Glu Ser Asn Leu Ser His Ser
                965                 970                 975

Ser Ser Phe Ser Met Ser Phe Glu Arg Glu Glu Thr Ser Lys Leu Ser
            980                 985                 990

Ala Leu Pro Lys Gln Asp Glu Phe Gly Lys His Ser Glu Phe Leu Thr
        995                 1000                1005

Val Pro Ala Gly Ser Tyr Ser Leu Ser Val Pro Gly His His His
    1010                1015                1020

Gln Lys Glu Met Arg Arg Cys Ser Ser Glu Gln Met Pro Cys Pro
    1025                1030                1035

His Pro Ala Glu Val Pro Glu Val Arg Ser Lys Ser Phe Asp Tyr
    1040                1045                1050

Gly Asn Leu Ser His Ala Pro Val Ser Gly Ala Ala Ala Ser Thr
    1055                1060                1065

Val Ser Pro Ser Arg Glu Arg Lys Lys Cys Phe Leu Val Arg Gln
    1070                1075                1080

Ala Ser Phe Ser Gly Ser Pro Glu Ile Ser Gln Gly Glu Val Gly
    1085                1090                1095

Met Asp Gln Ser Val Lys Gln Glu Gln Leu Glu His Leu His Ala
    1100                1105                1110

Gly Leu Arg Ser Gly Trp His His Gly Pro Ala Val Leu Pro
    1115                1120                1125

Pro Leu Gln Gln Glu Asp Pro Gly Lys Gln Val Ala Gly Pro Cys
    1130                1135                1140

Pro Pro Leu Ser Ser Gly Pro Leu His Leu Ala Gln Pro Gln Ile
    1145                1150                1155

Met His Met Asp Ser Gln Glu Ser Leu Arg Asn Pro Leu Ile Gln
```

|   |   |   |   |   |   |   |   |   |   |
|---|---|---|---|---|---|---|---|---|---|
|   | 1160 |   |   | 1165 |   |   | 1170 |   |   |
| Pro | Thr | Ser | Tyr | Met | Thr | Ser | Lys | His | Leu |
|   | 1175 |   |   | 1180 |   |   | 1185 |   |   |
| Pro | Glu | Gln | Pro | His |   |   |   |   |   |
| Leu | Phe | Pro | His | Gln | Glu | Thr | Ile | Pro | Phe |
|   | 1190 |   |   | 1195 |   |   | 1200 |   |   |
| Ser | Pro | Ile | Gln | Asn |   |   |   |   |   |
| Ala | Leu | Phe | Gln | Phe | Gln | Tyr | Pro | Thr | Val |
|   | 1205 |   |   | 1210 |   |   | 1215 |   |   |
| Cys | Met | Val | His | Leu |   |   |   |   |   |
| Pro | Ala | Gln | Gln | Pro | Pro | Trp | Trp | Gln | Ala |
|   | 1220 |   |   | 1225 |   |   | 1230 |   |   |
| His | Phe | Pro | His | Pro |   |   |   |   |   |
| Phe | Ala | Gln | His | Pro | Gln | Lys | Ser | Tyr | Gly |
|   | 1235 |   |   | 1240 |   |   | 1245 |   |   |
| Lys | Pro | Ser | Phe | Gln |   |   |   |   |   |
| Thr | Glu | Ile | His | Ser | Ser | Tyr | Pro | Leu | Glu |
|   | 1250 |   |   | 1255 |   |   | 1260 |   |   |
| His | Val | Ala | Glu | His |   |   |   |   |   |
| Thr | Gly | Lys | Lys | Pro | Ala | Glu | Tyr | Ala | His |
|   | 1265 |   |   | 1270 |   |   | 1275 |   |   |
| Thr | Lys | Glu | Gln | Thr |   |   |   |   |   |
| Tyr | Pro | Cys | Tyr | Ser | Gly | Ala | Ser | Gly | Leu |
|   | 1280 |   |   | 1285 |   |   | 1290 |   |   |
| His | Pro | Lys | Asn | Leu |   |   |   |   |   |
| Leu | Pro | Lys | Phe | Pro | Ser | Asp | Gln | Ser | Ser |
|   | 1295 |   |   | 1300 |   |   | 1305 |   |   |
| Lys | Ser | Thr | Glu | Thr |   |   |   |   |   |
| Pro | Ser | Glu | Gln | Val | Leu | Gln | Glu | Asp | Phe |
|   | 1310 |   |   | 1315 |   |   | 1320 |   |   |
| Ala | Ser | Ala | Asn | Ala |   |   |   |   |   |
| Gly | Ser | Leu | Gln | Ser | Leu | Pro | Gly | Thr | Val |
|   | 1325 |   |   | 1330 |   |   | 1335 |   |   |
| Val | Pro | Val | Arg | Ile |   |   |   |   |   |
| Gln | Thr | His | Val | Pro | Ser | Tyr | Gly | Ser | Val |
|   | 1340 |   |   | 1345 |   |   | 1350 |   |   |
| Met | Tyr | Thr | Ser | Ile |   |   |   |   |   |
| Ser | Gln | Ile | Leu | Gly | Gln | Asn | Ser | Pro | Ala |
|   | 1355 |   |   | 1360 |   |   | 1365 |   |   |
| Ile | Val | Ile | Cys | Lys |   |   |   |   |   |
| Val | Asp | Glu | Asn | Met | Thr | Gln | Arg | Thr | Leu |
|   | 1370 |   |   | 1375 |   |   | 1380 |   |   |
| Val | Thr | Asn | Ala | Ala |   |   |   |   |   |
| Met | Gln | Gly | Ile | Gly | Phe | Asn | Ile | Ala | Gln |
|   | 1385 |   |   | 1390 |   |   | 1395 |   |   |
| Val | Leu | Gly | Gln | His |   |   |   |   |   |
| Ala | Gly | Leu | Glu | Lys | Tyr | Pro | Ile | Trp | Lys |
|   | 1400 |   |   | 1405 |   |   | 1410 |   |   |
| Ala | Pro | Gln | Thr | Leu |   |   |   |   |   |
| Pro | Leu | Gly | Leu | Glu | Ser | Ser | Ile | Pro | Leu |
|   | 1415 |   |   | 1420 |   |   | 1425 |   |   |
| Cys | Leu | Pro | Ser | Thr |   |   |   |   |   |
| Ser | Asp | Ser | Val | Ala | Thr | Leu | Gly | Gly | Ser |
|   | 1430 |   |   | 1435 |   |   | 1440 |   |   |
| Lys | Arg | Met | Leu | Ser |   |   |   |   |   |
| Pro | Ala | Ser | Ser | Leu | Glu | Leu | Phe | Met | Glu |
|   | 1445 |   |   | 1450 |   |   | 1455 |   |   |
| Thr | Lys | Gln | Gln | Lys |   |   |   |   |   |
| Arg | Val | Lys | Glu | Glu | Lys | Met | Tyr | Gly | Gln |
|   | 1460 |   |   | 1465 |   |   | 1470 |   |   |
| Ile | Val | Glu | Glu | Leu |   |   |   |   |   |
| Ser | Ala | Val | Glu | Leu | Thr | Asn | Ser | Asp | Ile |
|   | 1475 |   |   | 1480 |   |   | 1485 |   |   |
| Lys | Lys | Asp | Leu | Ser |   |   |   |   |   |
| Arg | Pro | Gln | Lys | Pro | Gln | Leu | Val | Arg | Gln |
|   | 1490 |   |   | 1495 |   |   | 1500 |   |   |
| Gly | Cys | Ala | Ser | Glu |   |   |   |   |   |
| Pro | Lys | Asp | Gly | Leu | Gln | Ser | Gly | Ser | Ser |
|   | 1505 |   |   | 1510 |   |   | 1515 |   |   |
| Ser | Phe | Ser | Ser | Leu |   |   |   |   |   |
| Ser | Pro | Ser | Ser | Ser | Gln | Asp | Tyr | Pro | Ser |
|   | 1520 |   |   | 1525 |   |   | 1530 |   |   |
| Val | Ser | Pro | Ser | Ser |   |   |   |   |   |
| Arg | Glu | Pro | Phe | Leu | Pro | Ser | Lys | Glu | Met |
|   | 1535 |   |   | 1540 |   |   | 1545 |   |   |
| Leu | Ser | Gly | Ser | Arg |   |   |   |   |   |
| Ala | Pro | Leu | Pro | Gly | Gln | Lys | Ser | Ser | Gly |
|   | 1550 |   |   | 1555 |   |   | 1560 |   |   |
| Pro | Ser | Glu | Ser | Lys |   |   |   |   |   |

-continued

```
Glu Ser Ser Asp Glu Leu Asp Ile Asp Glu Thr Ala Ser Asp Met
1565                1570                1575
Ser Met Ser Pro Gln Ser Ser Ser Leu Pro Ala Gly Asp Gly Gln
1580                1585                1590
Leu Glu Glu Glu Gly Lys Gly His Lys Arg Pro Val Gly Met Leu
1595                1600                1605
Val Arg Met Ala Ser Ala Pro Ser Gly Asn Val Ala Asp Ser Thr
1610                1615                1620
Leu Leu Leu Thr Asp Met Ala Asp Phe Gln Gln Ile Leu Gln Phe
1625                1630                1635
Pro Ser Leu Arg Thr Thr Thr Thr Val Ser Trp Cys Phe Leu Asn
1640                1645                1650
Tyr Thr Lys Pro Asn Tyr Val Gln Gln Ala Thr Phe Lys Ser Ser
1655                1660                1665
Val Tyr Ala Ser Trp Cys Ile Ser Ser Cys Asn Pro Asn Pro Ser
1670                1675                1680
Gly Leu Asn Thr Lys Thr Thr Leu Ala Leu Leu Arg Ser Lys Gln
1685                1690                1695
Lys Ile Thr Ala Glu Ile Tyr Thr Leu Ala Ala Met His Arg Pro
1700                1705                1710
Gly Thr Gly Lys Leu Thr Ser Ser Ser Ala Trp Lys Gln Phe Thr
1715                1720                1725
Gln Met Lys Pro Asp Ala Ser Phe Leu Phe Gly Ser Lys Leu Glu
1730                1735                1740
Arg Lys Leu Val Gly Asn Ile Leu Lys Glu Arg Gly Lys Gly Asp
1745                1750                1755
Ile His Gly Asp Lys Asp Ile Gly Ser Lys Gln Thr Glu Pro Ile
1760                1765                1770
Arg Ile Lys Ile Phe Glu Gly Gly Tyr Lys Ser Asn Glu Asp Tyr
1775                1780                1785
Val Tyr Val Arg Gly Arg Gly Arg Gly Lys Tyr Ile Cys Glu Glu
1790                1795                1800
Cys Gly Ile Arg Cys Lys Lys Pro Ser Met Leu Lys Lys His Ile
1805                1810                1815
Arg Thr His Thr Asp Val Arg Pro Tyr Val Cys Lys Leu Cys Asn
1820                1825                1830
Phe Ala Phe Lys Thr Lys Gly Asn Leu Thr Lys His Met Lys Ser
1835                1840                1845
Lys Ala His Met Lys Lys Cys Leu Glu Leu Gly Val Ser Met Thr
1850                1855                1860
Ser Val Asp Asp Thr Glu Thr Glu Glu Ala Glu Asn Leu Glu Asp
1865                1870                1875
Leu His Lys Ala Ala Glu Lys His Ser Met Ser Ser Ile Ser Thr
1880                1885                1890
Asp His Gln Phe Ser Asp Ala Glu Glu Ser Asp Gly Glu Asp Gly
1895                1900                1905
Asp Asp Asn Asp Asp Asp Asp Glu Asp Glu Asp Phe Asp Asp
1910                1915                1920
Gln Gly Asp Leu Thr Pro Lys Thr Arg Ser Arg Ser Thr Ser Pro
1925                1930                1935
Gln Pro Pro Arg Phe Ser Ser Leu Pro Val Asn Val Gly Ala Val
1940                1945                1950
```

```
Pro His Gly Val Pro Ser Asp Ser Ser Leu Gly His Ser Ser Leu
1955                1960                1965

Ile Ser Tyr Leu Val Thr Leu Pro Ser Ile Arg Val Thr Gln Leu
1970                1975                1980

Met Thr Pro Ser Asp Ser Cys Glu Asp Thr Gln Met Thr Glu Tyr
1985                1990                1995

Gln Arg Leu Phe Gln Ser Lys Ser Thr Asp Ser Glu Pro Asp Lys
2000                2005                2010

Asp Arg Leu Asp Ile Pro Ser Cys Met Asp Glu Glu Cys Met Leu
2015                2020                2025

Pro Ser Glu Pro Ser Ser Pro Arg Asp Phe Ser Pro Ser Ser
2030                2035                2040

His His Ser Ser Pro Gly Tyr Asp Ser Ser Pro Cys Arg Asp Asn
2045                2050                2055

Ser Pro Lys Arg Tyr Leu Ile Pro Lys Gly Asp Leu Ser Pro Arg
2060                2065                2070

Arg His Leu Ser Pro Arg Arg Asp Leu Ser Pro Met Arg His Leu
2075                2080                2085

Ser Pro Arg Lys Glu Ala Ala Leu Arg Arg Glu Met Ser Gln Arg
2090                2095                2100

Asp Val Ser Pro Arg Arg His Leu Ser Pro Arg Arg Pro Val Ser
2105                2110                2115

Pro Gly Lys Asp Ile Thr Ala Arg Arg Asp Leu Ser Pro Arg Arg
2120                2125                2130

Glu Arg Arg Tyr Met Thr Thr Ile Arg Ala Pro Ser Pro Arg Arg
2135                2140                2145

Ala Leu Tyr His Asn Pro Pro Leu Ser Met Gly Gln Tyr Leu Gln
2150                2155                2160

Ala Glu Pro Ile Val Leu Gly Pro Pro Asn Leu Arg Arg Gly Leu
2165                2170                2175

Pro Gln Val Pro Tyr Phe Ser Leu Tyr Gly Asp Gln Glu Gly Ala
2180                2185                2190

Tyr Glu His Pro Gly Ser Ser Leu Phe Pro Glu Gly Pro Asn Asp
2195                2200                2205

Tyr Val Phe Ser His Leu Pro Leu His Ser Gln Gln Gln Val Arg
2210                2215                2220

Ala Pro Ile Pro Met Val Pro Val Gly Gly Ile Gln Met Val His
2225                2230                2235

Ser Met Pro Pro Ala Leu Ser Ser Leu His Pro Ser Pro Thr Leu
2240                2245                2250

Pro Leu Pro Met Glu Gly Phe Glu Glu Lys Lys Gly Ala Ser Gly
2255                2260                2265

Glu Ser Phe Ser Lys Asp Pro Tyr Val Leu Ser Lys Gln His Glu
2270                2275                2280

Lys Arg Gly Pro His Ala Leu Gln Ser Ser Gly Pro Pro Ser Thr
2285                2290                2295

Pro Ser Ser Pro Arg Leu Leu Met Lys Gln Ser Thr Ser Glu Asp
2300                2305                2310

Ser Leu Asn Ala Thr Glu Arg Glu Gln Glu Glu Asn Ile Gln Thr
2315                2320                2325

Cys Thr Lys Ala Ile Ala Ser Leu Arg Ile Ala Thr Glu Glu Ala
2330                2335                2340

Ala Leu Leu Gly Pro Asp Gln Pro Ala Arg Val Gln Glu Pro His
```

```
            2345                2350                2355
Gln Asn Pro Leu Gly Ser Ala His Val Ser Ile Arg His Phe Ser
        2360                2365                2370

Arg Pro Glu Pro Gly Gln Pro Cys Thr Ser Ala Thr His Pro Asp
    2375                2380                2385

Leu His Asp Gly Glu Lys Asp Asn Phe Gly Thr Ser Gln Thr Pro
        2390                2395                2400

Leu Ala His Ser Thr Phe Tyr Ser Lys Ser Cys Val Asp Asp Lys
    2405                2410                2415

Gln Leu Asp Phe His Ser Ser Lys Glu Leu Ser Ser Ser Thr Glu
        2420                2425                2430

Glu Ser Lys Asp Pro Ser Ser Glu Lys Ser Gln Leu His
    2435                2440                2445

<210> SEQ ID NO 3
<211> LENGTH: 342
<212> TYPE: PRT
<213> ORGANISM: Homo sapiens

<400> SEQUENCE: 3

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Glu Asp Ser Gly Gly Arg Met Thr Thr Ala Cys Ser
        35                  40                  45

Pro His Asn Pro Gln Cys Thr Ala Asp Leu Gly Ala Gln Tyr Ile Thr
    50                  55                  60

Cys Thr Pro His Tyr Ala Lys Lys His Gln Arg Phe Tyr Asp Glu Leu
65                  70                  75                  80

Leu Ala Tyr Gly Val Leu Arg Pro Leu Ser Ser Pro Ile Glu Gly Met
                85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
        115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
        195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270
```

```
Ile Leu Pro Gly Leu Pro Gln Pro Ile Ala Thr Lys Cys Gln Lys Trp
            275                 280                 285

Arg His Ser Gln Val Thr Asn Ala Ala Ala Asn Cys Pro Gly Gln Met
        290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
                325                 330                 335

Ala Leu Lys Asn Tyr Ile
            340

<210> SEQ ID NO 4
<211> LENGTH: 509
<212> TYPE: PRT
<213> ORGANISM: Homo sapiens

<400> SEQUENCE: 4

Met Asn Glu Glu Asp Leu Leu Gln Glu Asp Ser Thr Arg Asp Glu
1               5                   10                  15

Gly Asn Glu Thr Glu Ala Asn Ser Met Asn Thr Leu Arg Arg Thr Arg
            20                  25                  30

Lys Lys Val Thr Lys Pro Tyr Val Cys Ser Thr Glu Val Gly Glu Thr
        35                  40                  45

Asp Met Ser Asn Ser Asn Asp Cys Met Arg Asp Ser Ser Gln Ile Leu
    50                  55                  60

Thr Pro Pro Gln Leu Ser Ser Arg Met Lys His Ile Arg Gln Ala Met
65                  70                  75                  80

Ala Lys Asn Arg Leu Gln Phe Val Arg Phe Glu Ala Thr Asp Leu His
                85                  90                  95

Gly Val Ser Arg Ser Lys Thr Ile Pro Ala His Phe Gln Glu Lys
            100                 105                 110

Val Ser His Gly Val Cys Met Pro Arg Gly Tyr Leu Glu Val Ile Pro
        115                 120                 125

Asn Pro Lys Asp Asn Glu Met Asn Asn Ile Arg Ala Thr Cys Phe Asn
    130                 135                 140

Ser Asp Ile Val Leu Met Pro Glu Leu Ser Thr Phe Arg Val Leu Pro
145                 150                 155                 160

Trp Ala Asp Arg Thr Ala Arg Val Ile Cys Asp Thr Phe Thr Val Thr
                165                 170                 175

Gly Glu Pro Leu Leu Thr Ser Pro Arg Tyr Ile Ala Lys Arg Gln Leu
            180                 185                 190

Ser His Leu Gln Ala Ser Gly Phe Ser Leu Leu Ser Ala Phe Ile Tyr
        195                 200                 205

Asp Phe Cys Ile Phe Gly Val Pro Glu Ile Leu Asn Ser Lys Ile Ile
    210                 215                 220

Ser Phe Pro Ala Leu Thr Phe Leu Asn Asn His Asp Gln Pro Phe Met
225                 230                 235                 240

Gln Glu Leu Val Asp Gly Leu Tyr His Thr Gly Ala Asn Val Glu Ser
                245                 250                 255

Phe Ser Ser Ser Thr Arg Pro Gly Gln Met Glu Ile Ser Phe Leu Pro
            260                 265                 270

Glu Phe Gly Ile Ser Ser Ala Asp Asn Ala Phe Thr Leu Arg Thr Gly
        275                 280                 285

Val Lys Glu Val Ala Arg Lys Tyr Asn Tyr Ile Ala Ser Phe Phe Ile
    290                 295                 300
```

```
Glu Thr Gly Phe Cys Asp Ser Gly Ile Leu Ser His Ser Leu Trp Asp
305                 310                 315                 320

Val Asp Arg Lys Lys Asn Met Phe Cys Ser Thr Ser Gly Thr Glu Gln
                325                 330                 335

Leu Thr Ile Thr Gly Lys Lys Trp Leu Ala Gly Leu Leu Lys His Ser
            340                 345                 350

Ala Ala Leu Ser Cys Leu Met Ala Pro Ser Val Ser Cys Arg Lys Arg
        355                 360                 365

Tyr Ser Lys Asp Arg Lys Asp Leu Lys Lys Ser Val Pro Thr Thr Trp
    370                 375                 380

Gly Tyr Asn Asp Asn Ser Cys Ile Phe Asn Ile Lys Cys His Gly Glu
385                 390                 395                 400

Lys Gly Thr Arg Ile Glu Asn Lys Leu Gly Ser Ala Thr Ala Asn Pro
                405                 410                 415

Tyr Leu Val Leu Ala Ala Thr Val Ala Ala Gly Leu Asp Gly Leu His
            420                 425                 430

Ser Ser Asn Glu Val Leu Ala Gly Pro Asp Glu Ser Thr Asp Phe Tyr
        435                 440                 445

Gln Val Glu Pro Ser Glu Ile Pro Leu Lys Leu Glu Asp Ala Leu Val
    450                 455                 460

Ala Leu Glu Glu Asp Gln Cys Leu Arg Gln Ala Leu Gly Glu Thr Phe
465                 470                 475                 480

Ile Arg Tyr Phe Val Ala Met Lys Lys Tyr Glu Leu Glu Asn Glu Glu
                485                 490                 495

Ile Ala Ala Glu Arg Asn Lys Phe Leu Glu Tyr Phe Ile
                500                 505

<210> SEQ ID NO 5
<211> LENGTH: 2671
<212> TYPE: PRT
<213> ORGANISM: Homo sapiens

<400> SEQUENCE: 5

Met Ala Ala Asp Thr Gln Val Ser Glu Thr Leu Lys Arg Phe Ala Gly
1               5                   10                  15

Lys Val Thr Thr Ala Ser Val Lys Glu Arg Arg Glu Ile Leu Ser Glu
                20                  25                  30

Leu Gly Lys Cys Val Ala Gly Lys Asp Leu Pro Glu Gly Ala Val Lys
            35                  40                  45

Gly Leu Cys Lys Leu Phe Cys Leu Thr Leu His Arg Tyr Arg Asp Ala
        50                  55                  60

Ala Ser Arg Arg Ala Leu Gln Ala Ala Ile Gln Gln Leu Ala Glu Ala
65                  70                  75                  80

Gln Pro Glu Ala Thr Ala Lys Asn Leu Leu His Ser Leu Gln Ser Ser
                85                  90                  95

Gly Ile Gly Ser Lys Ala Gly Val Pro Ser Lys Ser Ser Gly Ser Ala
            100                 105                 110

Ala Leu Leu Ala Leu Thr Trp Thr Cys Leu Leu Val Arg Ile Val Phe
        115                 120                 125

Pro Ser Arg Ala Lys Arg Gln Gly Asp Ile Trp Asn Lys Leu Val Glu
    130                 135                 140

Val Gln Cys Leu Leu Leu Leu Glu Val Leu Gly Gly Ser His Lys His
145                 150                 155                 160

Ala Val Asp Gly Ala Val Lys Lys Leu Thr Lys Leu Trp Lys Glu Asn
```

```
            165                 170                 175
Pro Gly Leu Val Glu Gln Tyr Leu Ser Ala Ile Leu Ser Leu Glu Pro
            180                 185                 190

Asn Gln Asn Tyr Ala Gly Met Leu Gly Leu Leu Val Gln Phe Cys Thr
            195                 200                 205

Ser His Lys Glu Met Asp Val Val Ser Gln His Lys Ser Ala Leu Leu
            210                 215                 220

Asp Phe Tyr Met Lys Asn Ile Leu Met Ser Lys Val Lys Pro Pro Lys
225                 230                 235                 240

Tyr Leu Leu Asp Ser Cys Ala Pro Leu Leu Arg Tyr Leu Ser His Ser
                245                 250                 255

Glu Phe Lys Asp Leu Ile Leu Pro Thr Ile Gln Lys Ser Leu Leu Arg
            260                 265                 270

Ser Pro Glu Asn Val Ile Glu Thr Ile Ser Ser Leu Leu Ala Ser Val
            275                 280                 285

Thr Leu Asp Leu Ser Gln Tyr Ala Met Asp Ile Val Lys Gly Leu Ala
            290                 295                 300

Gly His Leu Lys Ser Asn Ser Pro Arg Leu Met Asp Glu Ala Val Leu
305                 310                 315                 320

Ala Leu Arg Asn Leu Ala Arg Gln Cys Ser Asp Ser Ala Met Glu
                325                 330                 335

Ser Leu Thr Lys His Leu Phe Ala Ile Leu Gly Gly Ser Glu Gly Lys
            340                 345                 350

Leu Thr Val Val Ala Gln Lys Met Ser Val Leu Ser Gly Ile Gly Ser
            355                 360                 365

Val Ser His His Val Val Ser Gly Pro Ser Ser Gln Val Leu Asn Gly
            370                 375                 380

Ile Val Ala Glu Leu Phe Ile Pro Phe Leu Gln Gln Glu Val His Glu
385                 390                 395                 400

Gly Thr Leu Val His Ala Val Ser Val Leu Ala Leu Trp Cys Asn Arg
                405                 410                 415

Phe Thr Met Glu Val Pro Lys Lys Leu Thr Glu Trp Phe Lys Lys Ala
            420                 425                 430

Phe Ser Leu Lys Thr Ser Thr Ser Ala Val Arg His Ala Tyr Leu Gln
            435                 440                 445

Cys Met Leu Ala Ser Tyr Arg Gly Asp Thr Leu Leu Gln Ala Leu Asp
            450                 455                 460

Leu Leu Pro Leu Leu Ile Gln Thr Val Glu Lys Ala Ala Ser Gln Ser
465                 470                 475                 480

Thr Gln Val Pro Thr Ile Thr Glu Gly Val Ala Ala Ala Leu Leu Leu
                485                 490                 495

Leu Lys Leu Ser Val Ala Asp Ser Gln Ala Glu Ala Lys Leu Ser Ser
            500                 505                 510

Phe Trp Gln Leu Ile Val Asp Glu Lys Lys Gln Val Phe Thr Ser Glu
            515                 520                 525

Lys Phe Leu Val Met Ala Ser Glu Asp Ala Leu Cys Thr Val Leu His
            530                 535                 540

Leu Thr Glu Arg Leu Phe Leu Asp His Pro His Arg Leu Thr Gly Asn
545                 550                 555                 560

Lys Val Gln Gln Tyr His Arg Ala Leu Val Ala Val Leu Leu Ser Arg
                565                 570                 575

Thr Trp His Val Arg Arg Gln Ala Gln Gln Thr Val Arg Lys Leu Leu
            580                 585                 590
```

```
Ser Ser Leu Gly Gly Phe Lys Leu Ala His Gly Leu Glu Glu Leu
        595                 600                 605

Lys Thr Val Leu Ser Ser His Lys Val Leu Pro Leu Glu Ala Leu Val
        610                 615                 620

Thr Asp Ala Gly Glu Val Thr Glu Ala Gly Lys Ala Tyr Val Pro Pro
625                 630                 635                 640

Arg Val Leu Gln Glu Ala Leu Cys Val Ile Ser Gly Val Pro Gly Leu
            645                 650                 655

Lys Gly Asp Val Thr Asp Thr Glu Gln Leu Ala Gln Glu Met Leu Ile
            660                 665                 670

Ile Ser His His Pro Ser Leu Val Ala Val Gln Ser Gly Leu Trp Pro
        675                 680                 685

Ala Leu Leu Ala Arg Met Lys Ile Asp Pro Glu Ala Phe Ile Thr Arg
        690                 695                 700

His Leu Asp Gln Ile Ile Pro Arg Met Thr Thr Gln Ser Pro Leu Asn
705                 710                 715                 720

Gln Ser Ser Met Asn Ala Met Gly Ser Leu Ser Val Leu Ser Pro Asp
                725                 730                 735

Arg Val Leu Pro Gln Leu Ile Ser Thr Ile Thr Ala Ser Val Gln Asn
            740                 745                 750

Pro Ala Leu Arg Leu Val Thr Arg Glu Glu Phe Ala Ile Met Gln Thr
            755                 760                 765

Pro Ala Gly Glu Leu Tyr Asp Lys Ser Ile Ile Gln Ser Ala Gln Gln
        770                 775                 780

Asp Ser Ile Lys Lys Ala Asn Met Lys Arg Glu Asn Lys Ala Tyr Ser
785                 790                 795                 800

Phe Lys Glu Gln Ile Ile Glu Leu Glu Leu Lys Glu Glu Ile Lys Lys
                805                 810                 815

Lys Lys Gly Ile Lys Glu Glu Val Gln Leu Thr Ser Lys Gln Lys Glu
            820                 825                 830

Met Leu Gln Ala Gln Leu Asp Arg Glu Ala Gln Val Arg Arg Arg Leu
        835                 840                 845

Gln Glu Leu Asp Gly Glu Leu Glu Ala Ala Leu Gly Leu Leu Asp Ile
        850                 855                 860

Ile Leu Ala Lys Asn Pro Ser Gly Leu Thr Gln Tyr Ile Pro Val Leu
865                 870                 875                 880

Val Asp Ser Phe Leu Pro Leu Leu Lys Ser Pro Leu Ala Ala Pro Arg
                885                 890                 895

Ile Lys Asn Pro Phe Leu Ser Leu Ala Ala Cys Val Met Pro Ser Arg
            900                 905                 910

Leu Lys Ala Leu Gly Thr Leu Val Ser His Val Thr Leu Arg Leu Leu
        915                 920                 925

Lys Pro Glu Cys Val Leu Asp Lys Ser Trp Cys Gln Glu Glu Leu Ser
        930                 935                 940

Val Ala Val Lys Arg Ala Val Met Leu Leu His Thr His Thr Ile Thr
945                 950                 955                 960

Ser Arg Val Gly Lys Gly Glu Pro Gly Ala Ala Pro Leu Ser Ala Pro
                965                 970                 975

Ala Phe Ser Leu Val Phe Pro Phe Leu Lys Met Val Leu Thr Glu Met
            980                 985                 990

Pro His His Ser Glu Glu Glu Glu Trp Met Ala Gln Ile Leu Gln
        995                 1000                1005
```

```
Ile Leu Thr Val Gln Ala Gln Leu Arg Ala Ser Pro Asn Thr Pro
    1010                1015                1020

Pro Gly Arg Val Asp Glu Asn Gly Pro Glu Leu Leu Pro Arg Val
    1025                1030                1035

Ala Met Leu Arg Leu Leu Thr Trp Val Ile Gly Thr Gly Ser Pro
    1040                1045                1050

Arg Leu Gln Val Leu Ala Ser Asp Thr Leu Thr Thr Leu Cys Ala
    1055                1060                1065

Ser Ser Ser Gly Asp Asp Gly Cys Ala Phe Ala Glu Gln Glu Glu
    1070                1075                1080

Val Asp Val Leu Leu Cys Ala Leu Gln Ser Pro Cys Ala Ser Val
    1085                1090                1095

Arg Glu Thr Val Leu Arg Gly Leu Met Glu Leu His Met Val Leu
    1100                1105                1110

Pro Ala Pro Asp Thr Asp Glu Lys Asn Gly Leu Asn Leu Leu Arg
    1115                1120                1125

Arg Leu Trp Val Val Lys Phe Asp Lys Glu Glu Glu Ile Arg Lys
    1130                1135                1140

Leu Ala Glu Arg Leu Trp Ser Met Met Gly Leu Asp Leu Gln Pro
    1145                1150                1155

Asp Leu Cys Ser Leu Leu Ile Asp Asp Val Ile Tyr His Glu Ala
    1160                1165                1170

Ala Val Arg Gln Ala Gly Ala Glu Ala Leu Ser Gln Ala Val Ala
    1175                1180                1185

Arg Tyr Gln Arg Gln Ala Ala Glu Val Met Gly Arg Leu Met Glu
    1190                1195                1200

Ile Tyr Gln Glu Lys Leu Tyr Arg Pro Pro Val Leu Asp Ala
    1205                1210                1215

Leu Gly Arg Val Ile Ser Glu Ser Pro Pro Asp Gln Trp Glu Ala
    1220                1225                1230

Arg Cys Gly Leu Ala Leu Ala Leu Asn Lys Leu Ser Gln Tyr Leu
    1235                1240                1245

Asp Ser Ser Gln Val Lys Pro Leu Phe Gln Phe Val Pro Asp
    1250                1255                1260

Ala Leu Asn Asp Arg His Pro Asp Val Arg Lys Cys Met Leu Asp
    1265                1270                1275

Ala Ala Leu Ala Thr Leu Asn Thr His Gly Lys Glu Asn Val Asn
    1280                1285                1290

Ser Leu Leu Pro Val Phe Glu Glu Phe Leu Lys Asn Ala Pro Asn
    1295                1300                1305

Asp Ala Ser Tyr Asp Ala Val Arg Gln Ser Val Val Val Leu Met
    1310                1315                1320

Gly Ser Leu Ala Lys His Leu Asp Lys Ser Asp Pro Lys Val Lys
    1325                1330                1335

Pro Ile Val Ala Lys Leu Ile Ala Ala Leu Ser Thr Pro Ser Gln
    1340                1345                1350

Gln Val Gln Glu Ser Val Ala Ser Cys Leu Pro Pro Leu Val Pro
    1355                1360                1365

Ala Ile Lys Glu Asp Ala Gly Gly Met Ile Gln Arg Leu Met Gln
    1370                1375                1380

Gln Leu Leu Glu Ser Asp Lys Tyr Ala Glu Arg Lys Gly Ala Ala
    1385                1390                1395

Tyr Gly Leu Ala Gly Leu Val Lys Gly Leu Gly Ile Leu Ser Leu
```

```
                1400                1405                1410
Lys Gln Gln Glu Met Met Ala Ala Leu Thr Asp Ala Ile Gln Asp
    1415                1420                1425
Lys Lys Asn Phe Arg Arg Arg Glu Gly Ala Leu Phe Ala Phe Glu
    1430                1435                1440
Met Leu Cys Thr Met Leu Gly Lys Leu Phe Glu Pro Tyr Val Val
    1445                1450                1455
His Val Leu Pro His Leu Leu Leu Cys Phe Gly Asp Gly Asn Gln
    1460                1465                1470
Tyr Val Arg Glu Ala Ala Asp Asp Cys Ala Lys Ala Val Met Ser
    1475                1480                1485
Asn Leu Ser Ala His Gly Val Lys Leu Val Leu Pro Ser Leu Leu
    1490                1495                1500
Ala Ala Leu Glu Glu Glu Ser Trp Arg Thr Lys Ala Gly Ser Val
    1505                1510                1515
Glu Leu Leu Gly Ala Met Ala Tyr Cys Ala Pro Lys Gln Leu Ser
    1520                1525                1530
Ser Cys Leu Pro Asn Ile Val Pro Lys Leu Thr Glu Val Leu Thr
    1535                1540                1545
Asp Ser His Val Lys Val Gln Lys Ala Gly Gln Gln Ala Leu Arg
    1550                1555                1560
Gln Ile Gly Ser Val Ile Arg Asn Pro Glu Ile Leu Ala Ile Ala
    1565                1570                1575
Pro Val Leu Leu Asp Ala Leu Thr Asp Pro Ser Arg Lys Thr Gln
    1580                1585                1590
Lys Cys Leu Gln Thr Leu Leu Asp Thr Lys Phe Val His Phe Ile
    1595                1600                1605
Asp Ala Pro Ser Leu Ala Leu Ile Met Pro Ile Val Gln Arg Ala
    1610                1615                1620
Phe Gln Asp Arg Ser Thr Asp Thr Arg Lys Met Ala Ala Gln Ile
    1625                1630                1635
Ile Gly Asn Met Tyr Ser Leu Thr Asp Gln Lys Asp Leu Ala Pro
    1640                1645                1650
Tyr Leu Pro Ser Val Thr Pro Gly Leu Lys Ala Ser Leu Leu Asp
    1655                1660                1665
Pro Val Pro Glu Val Arg Thr Val Ser Ala Lys Ala Leu Gly Ala
    1670                1675                1680
Met Val Lys Gly Met Gly Glu Ser Cys Phe Glu Asp Leu Leu Pro
    1685                1690                1695
Trp Leu Met Glu Thr Leu Thr Tyr Glu Gln Ser Ser Val Asp Arg
    1700                1705                1710
Ser Gly Ala Ala Gln Gly Leu Ala Glu Val Met Ala Gly Leu Gly
    1715                1720                1725
Val Glu Lys Leu Glu Lys Leu Met Pro Glu Ile Val Ala Thr Ala
    1730                1735                1740
Ser Lys Val Asp Ile Ala Pro His Val Arg Asp Gly Tyr Ile Met
    1745                1750                1755
Met Phe Asn Tyr Leu Pro Ile Thr Phe Gly Asp Lys Phe Thr Pro
    1760                1765                1770
Tyr Val Gly Pro Ile Ile Pro Cys Ile Leu Lys Ala Leu Ala Asp
    1775                1780                1785
Glu Asn Glu Phe Val Arg Asp Thr Ala Leu Arg Ala Gly Gln Arg
    1790                1795                1800
```

```
Val Ile Ser Met Tyr Ala Glu Thr Ala Ile Ala Leu Leu Leu Pro
    1805              1810                 1815

Gln Leu Glu Gln Gly Leu Phe Asp Asp Leu Trp Arg Ile Arg Phe
    1820              1825                 1830

Ser Ser Val Gln Leu Leu Gly Asp Leu Leu Phe His Ile Ser Gly
    1835              1840                 1845

Val Thr Gly Lys Met Thr Thr Glu Thr Ala Ser Glu Asp Asp Asn
    1850              1855                 1860

Phe Gly Thr Ala Gln Ser Asn Lys Ala Ile Ile Thr Ala Leu Gly
    1865              1870                 1875

Val Glu Arg Arg Asn Arg Val Leu Ala Gly Leu Tyr Met Gly Arg
    1880              1885                 1890

Ser Asp Thr Gln Leu Val Val Arg Gln Ala Ser Leu His Val Trp
    1895              1900                 1905

Lys Ile Val Val Ser Asn Thr Pro Arg Thr Leu Arg Glu Ile Leu
    1910              1915                 1920

Pro Thr Leu Phe Gly Leu Leu Leu Gly Phe Leu Ala Ser Thr Cys
    1925              1930                 1935

Ala Asp Lys Arg Thr Ile Ala Ala Arg Thr Leu Gly Asp Leu Val
    1940              1945                 1950

Arg Lys Leu Gly Glu Lys Ile Leu Pro Glu Ile Ile Pro Ile Leu
    1955              1960                 1965

Glu Glu Gly Leu Arg Ser Gln Lys Ser Asp Glu Arg Gln Gly Val
    1970              1975                 1980

Cys Ile Gly Leu Ser Glu Ile Met Lys Ser Thr Ser Arg Asp Ala
    1985              1990                 1995

Val Leu Tyr Phe Ser Glu Ser Leu Val Pro Thr Ala Arg Lys Ala
    2000              2005                 2010

Leu Cys Asp Pro Leu Glu Glu Val Arg Glu Ala Ala Ala Lys Thr
    2015              2020                 2025

Phe Glu Gln Leu His Ser Thr Ile Gly His Gln Ala Leu Glu Asp
    2030              2035                 2040

Ile Leu Pro Phe Leu Leu Lys Gln Leu Asp Asp Glu Glu Val Ser
    2045              2050                 2055

Glu Phe Ala Leu Asp Gly Leu Lys Gln Val Met Ala Ile Lys Ser
    2060              2065                 2070

Arg Val Val Leu Pro Tyr Leu Val Pro Lys Leu Thr Thr Pro Pro
    2075              2080                 2085

Val Asn Thr Arg Val Leu Ala Phe Leu Ser Ser Val Ala Gly Asp
    2090              2095                 2100

Ala Leu Thr Arg His Leu Gly Val Ile Leu Pro Ala Val Met Leu
    2105              2110                 2115

Ala Leu Lys Glu Lys Leu Gly Thr Pro Asp Glu Gln Leu Glu Met
    2120              2125                 2130

Ala Asn Cys Gln Ala Val Ile Leu Ser Val Glu Asp Asp Thr Gly
    2135              2140                 2145

His Arg Ile Ile Ile Glu Tyr Leu Leu Glu Ala Thr Arg Ser Pro
    2150              2155                 2160

Glu Val Gly Met Arg Gln Ala Ala Ala Ile Ile Leu Asn Ile Tyr
    2165              2170                 2175

Cys Ser Arg Ser Lys Ala Asp Tyr Thr Ser His Leu Arg Ser Leu
    2180              2185                 2190
```

-continued

```
Val Ser Gly Leu Ile Arg Leu Phe Asn Asp Ser Ser Pro Val Val
2195                2200                2205

Leu Glu Glu Ser Trp Asp Ala Leu Asn Ala Ile Thr Lys Lys Leu
2210                2215                2220

Asp Ala Gly Asn Gln Leu Ala Leu Ile Glu Glu Leu His Lys Glu
2225                2230                2235

Ile Arg Leu Ile Gly Asn Glu Ser Lys Gly Glu His Val Pro Gly
2240                2245                2250

Phe Cys Leu Pro Lys Lys Gly Val Thr Ser Ile Leu Pro Val Leu
2255                2260                2265

Arg Glu Gly Val Leu Thr Gly Ser Pro Glu Gln Lys Glu Glu Ala
2270                2275                2280

Ala Lys Ala Leu Gly Leu Val Ile Arg Leu Thr Ser Ala Asp Ala
2285                2290                2295

Leu Arg Pro Ser Val Val Ser Ile Thr Gly Pro Leu Ile Arg Ile
2300                2305                2310

Leu Gly Asp Arg Phe Ser Trp Asn Val Lys Ala Ala Leu Leu Glu
2315                2320                2325

Thr Leu Ser Leu Leu Leu Ala Lys Val Gly Ile Ala Leu Lys Pro
2330                2335                2340

Phe Leu Pro Gln Leu Gln Thr Thr Phe Thr Lys Ala Leu Gln Asp
2345                2350                2355

Ser Asn Arg Gly Val Arg Leu Lys Ala Ala Asp Ala Leu Gly Lys
2360                2365                2370

Leu Ile Ser Ile His Ile Lys Val Asp Pro Leu Phe Thr Glu Leu
2375                2380                2385

Leu Asn Gly Ile Arg Ala Met Glu Asp Pro Gly Val Arg Asp Thr
2390                2395                2400

Met Leu Gln Ala Leu Arg Phe Val Ile Gln Gly Ala Gly Ala Lys
2405                2410                2415

Val Asp Ala Val Ile Arg Lys Asn Ile Val Ser Leu Leu Leu Ser
2420                2425                2430

Met Leu Gly His Asp Glu Asp Asn Thr Arg Ile Ser Ser Ala Gly
2435                2440                2445

Cys Leu Gly Glu Leu Cys Ala Phe Leu Thr Glu Glu Glu Leu Ser
2450                2455                2460

Ala Val Leu Gln Gln Cys Leu Leu Ala Asp Val Ser Gly Ile Asp
2465                2470                2475

Trp Met Val Arg His Gly Arg Ser Leu Ala Leu Ser Val Ala Val
2480                2485                2490

Asn Val Ala Pro Gly Arg Leu Cys Ala Gly Arg Tyr Ser Ser Asp
2495                2500                2505

Val Gln Glu Met Ile Leu Ser Ser Ala Thr Ala Asp Arg Ile Pro
2510                2515                2520

Ile Ala Val Ser Gly Val Arg Gly Met Gly Phe Leu Met Arg His
2525                2530                2535

His Ile Glu Thr Gly Gly Gly Gln Leu Pro Ala Lys Leu Ser Ser
2540                2545                2550

Leu Phe Val Lys Cys Leu Gln Asn Pro Ser Ser Asp Ile Arg Leu
2555                2560                2565

Val Ala Glu Lys Met Ile Trp Trp Ala Asn Lys Asp Pro Leu Pro
2570                2575                2580

Pro Leu Asp Pro Gln Ala Ile Lys Pro Ile Leu Lys Ala Leu Leu
```

```
                     2585                2590                2595
Asp Asn Thr Lys Asp Lys Asn Thr Val Val Arg Ala Tyr Ser Asp
              2600                2605                2610
Gln Ala Ile Val Asn Leu Leu Lys Met Arg Gln Gly Glu Glu Val
              2615                2620                2625
Phe Gln Ser Leu Ser Lys Ile Leu Asp Val Ala Ser Leu Glu Val
              2630                2635                2640
Leu Asn Glu Val Asn Arg Arg Ser Leu Lys Lys Leu Ala Ser Gln
              2645                2650                2655
Ala Asp Ser Thr Glu Gln Val Asp Asp Thr Ile Leu Thr
              2660                2665                2670

<210> SEQ ID NO 6
<211> LENGTH: 1357
<212> TYPE: PRT
<213> ORGANISM: Homo sapiens

<400> SEQUENCE: 6

Met Gln Thr Leu Gly Ser Phe Phe Gly Ser Leu Pro Gly Phe Ser Ser
1               5                   10                  15
Ala Arg Asn Leu Val Ala Asn Ala His Ser Ser Ala Arg Ala Arg Pro
            20                  25                  30
Ala Ala Asp Pro Thr Gly Ala Pro Ala Ala Glu Ala Ala Gln Pro Gln
        35                  40                  45
Ala Gln Val Ala Ala His Pro Glu Gln Thr Ala Pro Trp Thr Glu Lys
    50                  55                  60
Glu Leu Gln Pro Ser Glu Lys Gln Met Val Ser Gly Ala Lys Asp Leu
65                  70                  75                  80
Val Cys Ser Lys Met Ser Arg Ala Lys Asp Ala Val Ser Ser Gly Val
                85                  90                  95
Ala Ser Val Val Asp Val Ala Lys Gly Val Gln Gly Gly Leu Asp
            100                 105                 110
Thr Thr Arg Ser Ala Leu Thr Gly Thr Lys Glu Val Ser Ser Gly
        115                 120                 125
Val Thr Gly Ala Met Asp Met Ala Lys Gly Ala Val Gln Gly Gly Leu
    130                 135                 140
Asp Thr Ser Lys Ala Val Leu Thr Gly Thr Lys Asp Thr Val Ser Thr
145                 150                 155                 160
Gly Leu Thr Gly Ala Val Asn Val Ala Lys Gly Thr Val Gln Ala Gly
                165                 170                 175
Val Asp Thr Thr Lys Thr Val Leu Thr Gly Thr Lys Asp Thr Val Thr
            180                 185                 190
Thr Gly Val Met Gly Ala Val Asn Leu Ala Lys Gly Thr Val Gln Thr
        195                 200                 205
Gly Val Glu Thr Ser Lys Ala Val Leu Thr Gly Thr Lys Asp Ala Val
    210                 215                 220
Ser Thr Gly Leu Thr Gly Ala Val Asn Val Ala Arg Gly Ser Ile Gln
225                 230                 235                 240
Thr Gly Val Asp Thr Ser Lys Thr Val Leu Thr Gly Thr Lys Asp Thr
                245                 250                 255
Val Cys Ser Gly Val Thr Gly Ala Met Asn Val Ala Lys Gly Thr Ile
            260                 265                 270
Gln Thr Gly Val Asp Ser Lys Thr Val Leu Thr Gly Thr Lys Asp
        275                 280                 285
```

-continued

```
Thr Val Cys Ser Gly Val Thr Gly Ala Met Asn Val Ala Lys Gly Thr
    290                 295                 300
Ile Gln Thr Gly Val Asp Thr Ser Lys Thr Val Leu Thr Gly Thr Lys
305                 310                 315                 320
Asp Thr Val Cys Ser Gly Val Thr Gly Ala Met Asn Val Ala Lys Gly
                325                 330                 335
Thr Ile Gln Thr Gly Val Asp Thr Thr Lys Thr Val Leu Thr Gly Thr
            340                 345                 350
Lys Asn Thr Val Cys Ser Gly Val Thr Gly Ala Val Asn Leu Ala Lys
        355                 360                 365
Glu Ala Ile Gln Gly Gly Leu Asp Thr Thr Lys Ser Met Val Met Gly
    370                 375                 380
Thr Lys Asp Thr Met Ser Thr Gly Leu Thr Gly Ala Ala Asn Val Ala
385                 390                 395                 400
Lys Gly Ala Met Gln Thr Gly Leu Asn Thr Thr Gln Asn Ile Ala Thr
                405                 410                 415
Gly Thr Lys Asp Thr Val Cys Ser Gly Val Thr Gly Ala Met Asn Leu
            420                 425                 430
Ala Arg Gly Thr Ile Gln Thr Gly Val Asp Thr Thr Lys Ile Val Leu
        435                 440                 445
Thr Gly Thr Lys Asp Thr Val Cys Ser Gly Val Thr Gly Ala Ala Asn
    450                 455                 460
Val Ala Lys Gly Ala Val Gln Gly Gly Leu Asp Thr Thr Lys Ser Val
465                 470                 475                 480
Leu Thr Gly Thr Lys Asp Ala Val Ser Thr Gly Leu Thr Gly Ala Val
                485                 490                 495
Asn Val Ala Lys Gly Thr Val Gln Thr Gly Val Asp Thr Thr Lys Thr
            500                 505                 510
Val Leu Thr Gly Thr Lys Asp Thr Val Cys Ser Gly Val Thr Ser Ala
        515                 520                 525
Val Asn Val Ala Lys Gly Ala Val Gln Gly Gly Leu Asp Thr Thr Lys
    530                 535                 540
Ser Val Val Ile Gly Thr Lys Asp Thr Met Ser Thr Gly Leu Thr Gly
545                 550                 555                 560
Ala Ala Asn Val Ala Lys Gly Ala Val Gln Thr Gly Val Asp Thr Ala
                565                 570                 575
Lys Thr Val Leu Thr Gly Thr Lys Asp Thr Val Thr Gly Leu Val
            580                 585                 590
Gly Ala Val Asn Val Ala Lys Gly Thr Val Gln Thr Gly Met Asp Thr
        595                 600                 605
Thr Lys Thr Val Leu Thr Gly Thr Lys Asp Thr Ile Tyr Ser Gly Val
    610                 615                 620
Thr Ser Ala Val Asn Val Ala Lys Gly Ala Val Gln Thr Gly Leu Lys
625                 630                 635                 640
Thr Thr Gln Asn Ile Ala Thr Gly Thr Lys Asn Thr Phe Gly Ser Gly
                645                 650                 655
Val Thr Ser Ala Val Asn Val Ala Lys Gly Ala Ala Gln Thr Gly Val
            660                 665                 670
Asp Thr Ala Lys Thr Val Leu Thr Gly Thr Lys Asp Thr Val Thr Thr
        675                 680                 685
Gly Leu Met Gly Ala Val Asn Val Ala Lys Gly Thr Val Gln Thr Ser
    690                 695                 700
Val Asp Thr Thr Lys Thr Val Leu Thr Gly Thr Lys Asp Thr Val Cys
```

-continued

```
            705                 710                 715                 720
Ser Gly Val Thr Gly Ala Ala Asn Val Ala Lys Gly Ala Ile Gln Gly
                725                 730                 735

Gly Leu Asp Thr Thr Lys Ser Val Leu Thr Gly Thr Lys Asp Ala Val
                740                 745                 750

Ser Thr Gly Leu Thr Gly Ala Val Lys Leu Ala Lys Gly Thr Val Gln
                755                 760                 765

Thr Gly Met Asp Thr Thr Lys Thr Val Leu Thr Gly Thr Lys Asp Ala
                770                 775                 780

Val Cys Ser Gly Val Thr Gly Ala Ala Asn Val Ala Lys Gly Ala Val
785                 790                 795                 800

Gln Met Gly Val Asp Thr Ala Lys Thr Val Leu Thr Gly Thr Lys Asp
                805                 810                 815

Thr Val Cys Ser Gly Val Thr Gly Ala Ala Asn Val Ala Lys Gly Ala
                820                 825                 830

Val Gln Thr Gly Leu Lys Thr Thr Gln Asn Ile Ala Thr Gly Thr Lys
                835                 840                 845

Asn Thr Leu Gly Ser Gly Val Thr Gly Ala Ala Lys Val Ala Lys Gly
850                 855                 860

Ala Val Gln Gly Gly Leu Asp Thr Thr Lys Ser Val Leu Thr Gly Thr
865                 870                 875                 880

Lys Asp Ala Val Ser Thr Gly Leu Thr Gly Ala Val Asn Leu Ala Lys
                885                 890                 895

Gly Thr Val Gln Thr Gly Val Asp Thr Ser Lys Thr Val Leu Thr Gly
                900                 905                 910

Thr Lys Asp Thr Val Cys Ser Gly Val Thr Gly Ala Val Asn Val Ala
                915                 920                 925

Lys Gly Thr Val Gln Thr Gly Val Asp Thr Ala Lys Thr Val Leu Ser
930                 935                 940

Gly Ala Lys Asp Ala Val Thr Thr Gly Val Thr Gly Ala Val Asn Val
945                 950                 955                 960

Ala Lys Gly Thr Val Gln Thr Gly Val Asp Ala Ser Lys Ala Val Leu
                965                 970                 975

Met Gly Thr Lys Asp Thr Val Phe Ser Gly Val Thr Gly Ala Met Ser
                980                 985                 990

Met Ala Lys Gly Ala Val Gln Gly Gly Leu Asp Thr Thr Lys Thr Val
                995                 1000                1005

Leu Thr Gly Thr Lys Asp Ala Val Ser Ala Gly Leu Met Gly Ser
                1010                1015                1020

Gly Asn Val Ala Thr Gly Ala Thr His Thr Gly Leu Ser Thr Phe
        1025                1030                1035

Gln Asn Trp Leu Pro Ser Thr Pro Ala Thr Ser Trp Gly Gly Leu
        1040                1045                1050

Thr Ser Ser Arg Thr Thr Asp Asn Gly Gly Glu Gln Thr Ala Leu
        1055                1060                1065

Ser Pro Gln Glu Ala Pro Phe Ser Gly Ile Ser Thr Pro Pro Asp
        1070                1075                1080

Val Leu Ser Val Gly Pro Glu Pro Ala Trp Glu Ala Ala Ala Thr
        1085                1090                1095

Thr Lys Gly Leu Ala Thr Asp Val Ala Thr Phe Thr Gln Gly Ala
        1100                1105                1110

Ala Pro Gly Arg Glu Asp Thr Gly Leu Leu Ala Thr Thr His Gly
        1115                1120                1125
```

```
Pro Glu Glu Ala Pro Arg Leu Ala Met Leu Gln Asn Glu Leu Glu
    1130                1135                1140

Gly Leu Gly Asp Ile Phe His Pro Met Asn Ala Glu Gln Ala
    1145                1150                1155

Gln Leu Ala Ala Ser Gln Pro Gly Pro Lys Val Leu Ser Ala Glu
    1160                1165                1170

Gln Gly Ser Tyr Phe Val Arg Leu Gly Asp Leu Gly Pro Ser Phe
    1175                1180                1185

Arg Gln Arg Ala Phe Glu His Ala Val Ser His Leu Gln His Gly
    1190                1195                1200

Gln Phe Gln Ala Arg Asp Thr Leu Ala Gln Leu Gln Asp Cys Phe
    1205                1210                1215

Arg Leu Ile Glu Lys Ala Gln Gln Ala Pro Glu Gly Gln Pro Arg
    1220                1225                1230

Leu Asp Gln Gly Ser Gly Ala Ser Ala Glu Asp Ala Ala Val Gln
    1235                1240                1245

Glu Glu Arg Asp Ala Gly Val Leu Ser Arg Val Cys Gly Leu Leu
    1250                1255                1260

Arg Gln Leu His Thr Ala Tyr Ser Gly Leu Val Ser Ser Leu Gln
    1265                1270                1275

Gly Leu Pro Ala Glu Leu Gln Gln Pro Val Gly Arg Ala Arg His
    1280                1285                1290

Ser Leu Cys Glu Leu Tyr Gly Ile Val Ala Ser Ala Gly Ser Val
    1295                1300                1305

Glu Glu Leu Pro Ala Glu Arg Leu Val Gln Ser Arg Glu Gly Val
    1310                1315                1320

His Gln Ala Trp Gln Gly Leu Glu Gln Leu Leu Glu Gly Leu Gln
    1325                1330                1335

His Asn Pro Pro Leu Ser Trp Leu Val Gly Pro Phe Ala Leu Pro
    1340                1345                1350

Ala Gly Gly Gln
    1355

<210> SEQ ID NO 7
<211> LENGTH: 117
<212> TYPE: PRT
<213> ORGANISM: Homo sapiens

<400> SEQUENCE: 7

Met Ala Thr Tyr Ser Leu Ala Asn Glu Arg Leu Arg Ala Leu Glu Asp
1               5                   10                  15

Ile Glu Arg Glu Ile Gly Ala Ile Leu Gln Asn Ala Gly Thr Val Ile
                20                  25                  30

Leu Glu Leu Ser Lys Glu Lys Thr Asn Glu Arg Leu Leu Asp Arg Gln
            35                  40                  45

Ala Ala Ala Phe Thr Ala Ser Val Gln His Val Glu Ala Glu Leu Ser
        50                  55                  60

Ala Gln Ile Arg Tyr Leu Thr Gln Val Ala Thr Gly Gln Pro His Glu
65                  70                  75                  80

Gly Ser Ser Tyr Ser Ser Arg Lys Asp Cys Gln Met Ala Leu Lys Arg
                85                  90                  95

Val Asp Tyr Ala Arg Leu Lys Leu Ser Asp Val Ala Arg Thr Cys Glu
                100                 105                 110

Gln Met Leu Glu Asn
```

-continued

115

<210> SEQ ID NO 8
<211> LENGTH: 706
<212> TYPE: PRT
<213> ORGANISM: Homo sapiens

<400> SEQUENCE: 8

```
Met Ala Gly Ile Arg Val Thr Lys Val Asp Trp Gln Arg Ser Arg Asn
1               5                   10                  15

Gly Ala Ala His His Thr Gln Glu Tyr Pro Cys Pro Glu Leu Val Val
            20                  25                  30

Arg Arg Gly Gln Ser Phe Ser Leu Thr Leu Glu Leu Ser Arg Ala Leu
        35                  40                  45

Asp Cys Glu Glu Ile Leu Ile Phe Thr Met Glu Thr Gly Pro Arg Ala
50                  55                  60

Ser Glu Ala Leu His Thr Lys Ala Val Phe Gln Thr Ser Glu Leu Glu
65                  70                  75                  80

Arg Gly Glu Gly Trp Thr Ala Ala Arg Glu Ala Gln Met Glu Lys Thr
                85                  90                  95

Leu Thr Val Ser Leu Ala Ser Pro Pro Ser Ala Val Ile Gly Arg Tyr
            100                 105                 110

Leu Leu Ser Ile Arg Leu Ser Ser His Arg Lys His Ser Asn Arg Arg
        115                 120                 125

Leu Gly Glu Phe Val Leu Leu Phe Asn Pro Trp Cys Ala Glu Asp Asp
130                 135                 140

Val Phe Leu Ala Ser Glu Glu Arg Gln Glu Tyr Val Leu Ser Asp
145                 150                 155                 160

Ser Gly Ile Ile Phe Arg Gly Val Glu Lys His Ile Arg Ala Gln Gly
                165                 170                 175

Trp Asn Tyr Gly Gln Phe Glu Glu Asp Ile Leu Asn Ile Cys Leu Ser
            180                 185                 190

Ile Leu Asp Arg Ser Pro Gly His Gln Asn Asn Pro Ala Thr Asp Val
        195                 200                 205

Ser Cys Arg His Asn Pro Ile Tyr Val Thr Arg Val Ile Ser Ala Met
210                 215                 220

Val Asn Ser Asn Asn Asp Arg Gly Val Val Gln Gly Gln Trp Gln Gly
225                 230                 235                 240

Lys Tyr Gly Gly Gly Thr Ser Pro Leu His Trp Arg Gly Ser Val Ala
                245                 250                 255

Ile Leu Gln Lys Trp Leu Lys Gly Arg Tyr Lys Pro Val Lys Tyr Gly
            260                 265                 270

Gln Cys Trp Val Phe Ala Gly Val Leu Cys Thr Val Leu Arg Cys Leu
        275                 280                 285

Gly Ile Ala Thr Arg Val Val Ser Asn Phe Asn Ser Ala His Asp Thr
290                 295                 300

Asp Gln Asn Leu Ser Val Asp Lys Tyr Val Asp Ser Phe Gly Arg Thr
305                 310                 315                 320

Leu Glu Asp Leu Thr Glu Asp Ser Met Trp Asn Phe His Val Trp Asn
                325                 330                 335

Glu Ser Trp Phe Ala Arg Gln Asp Leu Gly Pro Ser Tyr Asn Gly Trp
            340                 345                 350

Gln Val Leu Asp Ala Thr Pro Gln Glu Glu Ser Glu Gly Val Phe Arg
        355                 360                 365
```

Cys Gly Pro Ala Ser Val Thr Ala Ile Arg Glu Gly Asp Val His Leu
370                 375                 380

Ala His Asp Gly Pro Phe Val Phe Ala Glu Val Asn Ala Asp Tyr Ile
385                 390                 395                 400

Thr Trp Leu Trp His Glu Asp Glu Ser Arg Glu Arg Val Tyr Ser Asn
                405                 410                 415

Thr Lys Lys Ile Gly Arg Cys Ile Ser Thr Lys Ala Val Gly Ser Asp
                420                 425                 430

Ser Arg Val Asp Ile Thr Asp Leu Tyr Lys Tyr Pro Glu Gly Ser Arg
            435                 440                 445

Lys Glu Arg Gln Val Tyr Ser Lys Ala Val Asn Arg Leu Phe Gly Val
450                 455                 460

Glu Ala Ser Gly Arg Arg Ile Trp Ile Arg Arg Ala Gly Gly Arg Cys
465                 470                 475                 480

Leu Trp Arg Asp Asp Leu Leu Glu Pro Ala Thr Lys Pro Ser Ile Ala
                485                 490                 495

Gly Lys Phe Lys Val Leu Glu Pro Pro Met Leu Gly His Asp Leu Arg
                500                 505                 510

Leu Ala Leu Cys Leu Ala Asn Leu Thr Ser Arg Ala Gln Arg Val Arg
            515                 520                 525

Val Asn Leu Ser Gly Ala Thr Ile Leu Tyr Thr Arg Lys Pro Val Ala
530                 535                 540

Glu Ile Leu His Glu Ser His Ala Val Arg Leu Gly Pro Gln Glu Glu
545                 550                 555                 560

Lys Arg Ile Pro Ile Thr Ile Ser Tyr Ser Lys Tyr Lys Glu Asp Leu
                565                 570                 575

Thr Glu Asp Lys Lys Ile Leu Leu Ala Ala Met Cys Leu Val Thr Lys
                580                 585                 590

Gly Glu Lys Leu Leu Val Glu Lys Asp Ile Thr Leu Glu Asp Phe Ile
            595                 600                 605

Thr Ile Lys Val Leu Gly Pro Ala Met Val Gly Val Ala Val Thr Val
610                 615                 620

Glu Val Thr Val Val Asn Pro Leu Ile Glu Arg Val Lys Asp Cys Ala
625                 630                 635                 640

Leu Met Val Glu Gly Ser Gly Leu Leu Gln Glu Gln Leu Ser Ile Asp
                645                 650                 655

Val Pro Thr Leu Glu Pro Gln Glu Arg Ala Ser Val Gln Phe Asp Ile
            660                 665                 670

Thr Pro Ser Lys Ser Gly Pro Arg Gln Leu Gln Val Asp Leu Val Ser
            675                 680                 685

Pro His Phe Pro Asp Ile Lys Gly Phe Val Ile Val His Val Ala Thr
690                 695                 700

Ala Lys
705

<210> SEQ ID NO 9
<211> LENGTH: 234
<212> TYPE: PRT
<213> ORGANISM: Homo sapiens

<400> SEQUENCE: 9

Met Arg Ser Gly Glu Pro Ala Cys Thr Met Asp Gln Ala Arg Gly Leu
1               5                   10                  15

Asp Asp Ala Ala Ala Arg Gly Gly Gln Cys Pro Gly Leu Gly Pro Ala
                20                  25                  30

```
Pro Thr Pro Thr Pro Pro Gly Arg Leu Gly Ala Pro Tyr Ser Glu Ala
            35                  40                  45

Trp Gly Tyr Phe His Leu Ala Pro Gly Arg Pro Gly His Pro Ser Gly
 50                  55                  60

His Trp Ala Thr Cys Arg Leu Cys Gly Glu Gln Val Gly Arg Gly Pro
 65                  70                  75                  80

Gly Phe His Ala Gly Thr Ser Ala Leu Trp Arg His Leu Arg Ser Ala
                85                  90                  95

His Arg Arg Glu Leu Glu Ser Ser Gly Ala Gly Ser Ser Pro Pro Ala
                100                 105                 110

Ala Pro Cys Pro Pro Pro Gly Pro Ala Ala Pro Glu Gly Asp
                115                 120                 125

Trp Ala Arg Leu Leu Glu Gln Met Gly Ala Leu Ala Val Arg Gly Ser
130                 135                 140

Arg Arg Glu Arg Glu Leu Glu Arg Arg Glu Leu Ala Val Glu Gln Gly
145                 150                 155                 160

Glu Arg Ala Leu Glu Arg Arg Arg Ala Leu Gln Glu Glu Glu Arg
                165                 170                 175

Ala Ala Ala Gln Ala Arg Arg Glu Leu Gln Ala Glu Arg Glu Ala Leu
                180                 185                 190

Gln Ala Arg Leu Arg Asp Val Ser Arg Arg Glu Gly Ala Leu Gly Trp
                195                 200                 205

Ala Pro Ala Ala Pro Pro Leu Lys Asp Asp Pro Glu Gly Asp Arg
210                 215                 220

Asp Gly Cys Val Ile Thr Lys Val Leu Leu
225                 230

<210> SEQ ID NO 10
<211> LENGTH: 872
<212> TYPE: PRT
<213> ORGANISM: Homo sapiens

<400> SEQUENCE: 10

Met Gly Ser Leu Leu Ala Leu Leu Ala Leu Leu Leu Leu Trp Gly Ala
 1               5                  10                  15

Val Ala Glu Gly Pro Ala Lys Lys Val Leu Thr Leu Glu Gly Asp Leu
                20                  25                  30

Val Leu Gly Gly Leu Phe Pro Val His Gln Lys Gly Gly Pro Ala Glu
                35                  40                  45

Asp Cys Gly Pro Val Asn Glu His Arg Gly Ile Gln Arg Leu Glu Ala
 50                  55                  60

Met Leu Phe Ala Leu Asp Arg Ile Asn Arg Asp Pro His Leu Leu Pro
 65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
                100                 105                 110

Gly Ala Asp Gly Ser Arg His Ile Cys Pro Asp Gly Ser Tyr Ala Thr
                115                 120                 125

His Gly Asp Ala Pro Thr Ala Ile Thr Gly Val Ile Gly Gly Ser Tyr
                130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
```

-continued

```
            165                 170                 175
Arg Tyr Asp Tyr Phe Ala Arg Thr Val Pro Asp Phe Phe Gln Ala
                180                 185                 190
Lys Ala Met Ala Glu Ile Leu Arg Phe Phe Asn Trp Thr Tyr Val Ser
                195                 200                 205
Thr Val Ala Ser Glu Gly Asp Tyr Gly Glu Thr Gly Ile Glu Ala Phe
                210                 215                 220
Glu Leu Glu Ala Arg Ala Arg Asn Ile Cys Val Ala Thr Ser Glu Lys
225                 230                 235                 240
Val Gly Arg Ala Met Ser Arg Ala Ala Phe Glu Gly Val Val Arg Ala
                245                 250                 255
Leu Leu Gln Lys Pro Ser Ala Arg Val Ala Val Leu Phe Thr Arg Ser
                260                 265                 270
Glu Asp Ala Arg Glu Leu Leu Ala Ala Ser Gln Arg Leu Asn Ala Ser
                275                 280                 285
Phe Thr Trp Val Ala Ser Asp Gly Trp Gly Ala Leu Glu Ser Val Val
                290                 295                 300
Ala Gly Ser Glu Gly Ala Ala Glu Gly Ala Ile Thr Ile Glu Leu Ala
305                 310                 315                 320
Ser Tyr Pro Ile Ser Asp Phe Ala Ser Tyr Phe Gln Ser Leu Asp Pro
                325                 330                 335
Trp Asn Asn Ser Arg Asn Pro Trp Phe Arg Glu Phe Trp Glu Gln Arg
                340                 345                 350
Phe Arg Cys Ser Phe Arg Gln Arg Asp Cys Ala Ala His Ser Leu Arg
                355                 360                 365
Ala Val Pro Phe Glu Gln Glu Ser Lys Ile Met Phe Val Val Asn Ala
                370                 375                 380
Val Tyr Ala Met Ala His Ala Leu His Asn Met His Arg Ala Leu Cys
385                 390                 395                 400
Pro Asn Thr Thr Arg Leu Cys Asp Ala Met Arg Pro Val Asn Gly Arg
                405                 410                 415
Arg Leu Tyr Lys Asp Phe Val Leu Asn Val Lys Phe Asp Ala Pro Phe
                420                 425                 430
Arg Pro Ala Asp Thr His Asn Glu Val Arg Phe Asp Arg Phe Gly Asp
                435                 440                 445
Gly Ile Gly Arg Tyr Asn Ile Phe Thr Tyr Leu Arg Ala Gly Ser Gly
                450                 455                 460
Arg Tyr Arg Tyr Gln Lys Val Gly Tyr Trp Ala Glu Gly Leu Thr Leu
465                 470                 475                 480
Asp Thr Ser Leu Ile Pro Trp Ala Ser Pro Ser Ala Gly Pro Leu Pro
                485                 490                 495
Ala Ser Arg Cys Ser Glu Pro Cys Leu Gln Asn Glu Val Lys Ser Val
                500                 505                 510
Gln Pro Gly Glu Val Cys Cys Trp Leu Cys Ile Pro Cys Gln Pro Tyr
                515                 520                 525
Glu Tyr Arg Leu Asp Glu Phe Thr Cys Ala Asp Cys Gly Leu Gly Tyr
                530                 535                 540
Trp Pro Asn Ala Ser Leu Thr Gly Cys Phe Glu Leu Pro Gln Glu Tyr
545                 550                 555                 560
Ile Arg Trp Gly Asp Ala Trp Ala Val Gly Pro Val Thr Ile Ala Cys
                565                 570                 575
Leu Gly Ala Leu Ala Thr Leu Phe Val Leu Gly Val Phe Val Arg His
                580                 585                 590
```

-continued

Asn Ala Thr Pro Val Lys Ala Ser Gly Arg Glu Leu Cys Tyr Ile
            595                 600                 605

Leu Leu Gly Gly Val Phe Leu Cys Tyr Cys Met Thr Phe Ile Phe Ile
610                 615                 620

Ala Lys Pro Ser Thr Ala Val Cys Thr Leu Arg Arg Leu Gly Leu Gly
625                 630                 635                 640

Thr Ala Phe Ser Val Cys Tyr Ser Ala Leu Leu Thr Lys Thr Asn Arg
                645                 650                 655

Ile Ala Arg Ile Phe Gly Gly Ala Arg Glu Gly Ala Gln Arg Pro Arg
            660                 665                 670

Phe Ile Ser Pro Ala Ser Gln Val Ala Ile Cys Leu Ala Leu Ile Ser
            675                 680                 685

Gly Gln Leu Leu Ile Val Val Ala Trp Leu Val Val Glu Ala Pro Gly
            690                 695                 700

Thr Gly Lys Glu Thr Ala Pro Glu Arg Arg Glu Val Val Thr Leu Arg
705                 710                 715                 720

Cys Asn His Arg Asp Ala Ser Met Leu Gly Ser Leu Ala Tyr Asn Val
                725                 730                 735

Leu Leu Ile Ala Leu Cys Thr Leu Tyr Ala Phe Lys Thr Arg Lys Cys
            740                 745                 750

Pro Glu Asn Phe Asn Glu Ala Lys Phe Ile Gly Phe Thr Met Tyr Thr
            755                 760                 765

Thr Cys Ile Ile Trp Leu Ala Phe Leu Pro Ile Phe Tyr Val Thr Ser
            770                 775                 780

Ser Asp Tyr Arg Val Gln Thr Thr Thr Met Cys Val Ser Val Ser Leu
785                 790                 795                 800

Ser Gly Ser Val Val Leu Gly Cys Leu Phe Ala Pro Lys Leu His Ile
                805                 810                 815

Ile Leu Phe Gln Pro Gln Lys Asn Val Val Ser His Arg Ala Pro Thr
            820                 825                 830

Ser Arg Phe Gly Ser Ala Ala Ala Arg Ala Ser Ser Ser Leu Gly Gln
            835                 840                 845

Gly Ser Gly Ser Gln Phe Val Pro Thr Val Cys Asn Gly Arg Glu Val
            850                 855                 860

Val Asp Ser Thr Thr Ser Ser Leu
865                 870

<210> SEQ ID NO 11
<211> LENGTH: 611
<212> TYPE: PRT
<213> ORGANISM: Mus musculus

<400> SEQUENCE: 11

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
        35                  40                  45

Ala Val Asn Arg Val Ile Pro Thr Asn Val Pro Glu Leu Thr Phe Gln
    50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln

```
                        85                  90                  95
Ile Arg Gly Ala Val Asp Leu Ser Leu Tyr Pro Arg Glu Gly Val
                100                 105                 110
Ser Ser Arg Glu Leu Val Lys Lys Val Ser Asp Val Ile Trp Asn Ser
            115                 120                 125
Leu Ser Arg Ser Tyr Phe Lys Asp Arg Ala His Ile Gln Ser Leu Phe
        130                 135                 140
Ser Phe Ile Thr Gly Thr Lys Leu Asp Ser Ser Gly Val Ala Phe Ala
145                 150                 155                 160
Val Val Gly Ala Cys Gln Ala Leu Gly Leu Arg Asp Val His Leu Ala
                165                 170                 175
Leu Ser Glu Asp His Ala Trp Val Val Phe Gly Pro Asn Gly Glu Gln
            180                 185                 190
Thr Ala Glu Val Thr Trp His Gly Lys Gly Asn Glu Asp Arg Arg Gly
        195                 200                 205
Gln Thr Val Asn Ala Gly Val Ala Glu Arg Ser Trp Leu Tyr Leu Lys
    210                 215                 220
Gly Ser Tyr Met Arg Cys Asp Arg Lys Met Glu Val Ala Phe Met Val
225                 230                 235                 240
Cys Ala Ile Asn Pro Ser Ile Asp Leu His Thr Asp Ser Leu Glu Leu
                245                 250                 255
Leu Gln Leu Gln Gln Lys Leu Leu Trp Leu Leu Tyr Asp Leu Gly His
            260                 265                 270
Leu Glu Arg Tyr Pro Met Ala Leu Gly Asn Leu Ala Asp Leu Glu Glu
        275                 280                 285
Leu Glu Pro Thr Pro Gly Arg Pro Asp Pro Leu Thr Leu Tyr His Lys
    290                 295                 300
Gly Ile Ala Ser Ala Lys Thr Tyr Tyr Gln Asp Glu His Ile Tyr Pro
305                 310                 315                 320
Tyr Met Tyr Leu Ala Gly Tyr His Cys Arg Asn Arg Asn Val Arg Glu
                325                 330                 335
Ala Leu Gln Ala Trp Ala Asp Thr Ala Thr Val Ile Gln Asp Tyr Asn
            340                 345                 350
Tyr Cys Arg Glu Asp Glu Glu Ile Tyr Lys Glu Phe Phe Glu Val Ala
        355                 360                 365
Asn Asp Val Ile Pro Asn Leu Leu Lys Glu Ala Ala Ser Leu Leu Glu
    370                 375                 380
Thr Gly Glu Glu Arg Thr Gly Glu Gln Ala Gln Gly Thr Gln Gly Gln
385                 390                 395                 400
Gly Ser Ala Leu Gln Asp Pro Glu Cys Phe Ala His Leu Leu Arg Phe
                405                 410                 415
Tyr Asp Gly Ile Cys Lys Trp Glu Glu Gly Ser Pro Thr Pro Val Leu
            420                 425                 430
His Val Gly Trp Ala Thr Phe Leu Val Gln Ser Leu Gly Arg Phe Glu
        435                 440                 445
Gly Gln Val Arg Gln Lys Val His Ile Val Ser Arg Glu Ala Glu Ala
    450                 455                 460
Ala Glu Ala Glu Glu Pro Trp Gly Asp Glu Ala Arg Glu Gly Arg Arg
465                 470                 475                 480
Arg Gly Pro Arg Arg Glu Ser Lys Pro Glu Glu Pro Pro Pro Lys
                485                 490                 495
Lys Pro Ala Leu Asp Lys Gly Pro Gly Ser Gly Gln Ser Ala Gly Ser
            500                 505                 510
```

Gly Pro Pro Arg Lys Thr Ser Gly Thr Val Pro Gly Thr Thr Arg Gly
            515                 520                 525

Gly Gln Glu Val Gly Asn Ala Ala Gln Ala Pro Ala Pro Ala Ala Ser
        530                 535                 540

Pro Pro Pro Glu Gly Pro Val Leu Thr Phe Gln Ser Glu Lys Met Lys
545                 550                 555                 560

Gly Met Lys Glu Leu Leu Val Ala Thr Lys Ile Asn Ser Ser Ala Ile
                565                 570                 575

Lys Leu Gln Leu Thr Ala Gln Ser Gln Val Gln Met Lys Lys Gln Lys
            580                 585                 590

Val Ser Thr Pro Ser Asp Tyr Thr Leu Ser Phe Leu Lys Arg Gln Arg
            595                 600                 605

Lys Gly Leu
        610

<210> SEQ ID NO 12
<211> LENGTH: 2430
<212> TYPE: PRT
<213> ORGANISM: Mus musculus

<400> SEQUENCE: 12

Met Asp Thr Gly Asp Thr Ala Leu Gly Gln Lys Ala Thr Ser Arg Ser
1               5                   10                  15

Gly Glu Thr Asp Ser Val Ser Gly Arg Trp Arg Gln Glu Gln Ser Ala
            20                  25                  30

Val Leu Lys Met Ser Thr Phe Ser Ser Gln Glu Gly Pro Arg Gln Pro
        35                  40                  45

Gln Ile Asp Pro Glu Gln Ile Gly Asn Ala Ala Ser Ala Gln Leu Phe
    50                  55                  60

Gly Ser Gly Lys Leu Ala Ser Pro Gly Glu Gly Leu His Gln Val Thr
65                  70                  75                  80

Glu Lys Gln Tyr Pro Pro His Arg Pro Ser Pro Tyr Pro Cys Gln His
                85                  90                  95

Ser Leu Ser Phe Pro Gln His Ser Leu Ser Gln Gly Met Thr His Ser
            100                 105                 110

His Lys Pro His Gln Ser Leu Glu Gly Pro Pro Trp Leu Phe Pro Gly
        115                 120                 125

Pro Leu Pro Ser Val Ala Ser Glu Asp Leu Phe Pro Phe Pro Met His
    130                 135                 140

Gly His Ser Gly Gly Tyr Pro Arg Lys Lys Ile Ser Asn Leu Asn Pro
145                 150                 155                 160

Ala Tyr Ser Gln Tyr Ser Gln Lys Ser Ile Glu Gln Ala Glu Asp Ala
                165                 170                 175

His Lys Lys Glu His Lys Pro Lys Lys Pro Gly Lys Tyr Ile Cys Pro
            180                 185                 190

Tyr Cys Ser Arg Ala Cys Ala Lys Pro Ser Val Leu Lys Lys His Ile
        195                 200                 205

Arg Ser His Thr Gly Glu Arg Pro Tyr Pro Cys Ile Pro Cys Gly Phe
    210                 215                 220

Ser Phe Lys Thr Lys Ser Asn Leu Tyr Lys His Arg Lys Ser His Ala
225                 230                 235                 240

His Ala Ile Lys Ala Gly Leu Val Pro Phe Thr Glu Ser Ser Val Ser
                245                 250                 255

Lys Leu Asp Leu Glu Ala Gly Phe Ile Asp Val Glu Ala Glu Ile His

```
                260                 265                 270
Ser Asp Gly Glu Gln Ser Thr Asp Thr Asp Glu Glu Ser Ser Leu Phe
            275                 280                 285
Ala Glu Ala Ser Asp Lys Val Ser Pro Gly Pro Val Pro Leu Asp
        290                 295                 300
Ile Ala Ser Arg Gly Tyr His Gly Ser Leu Glu Glu Ser Leu Gly
305                 310                 315                 320
Gly Pro Met Lys Val Pro Ile Leu Ile Pro Lys Ser Gly Ile Pro
                325                 330                 335
Leu Ala Ser Glu Gly Ser Gln Tyr Leu Ser Ser Glu Met Leu Pro Asn
            340                 345                 350
Pro Ser Leu Asn Ala Lys Ala Asp Asp Ser His Thr Val Lys Gln Lys
        355                 360                 365
Leu Ala Leu Arg Leu Ser Glu Lys Lys Gly Gln Asp Ser Glu Pro Ser
        370                 375                 380
Leu Asn Leu Leu Ser Pro His Ser Lys Gly Ser Thr Asp Ser Gly Tyr
385                 390                 395                 400
Phe Ser Arg Ser Glu Ser Ala Glu Gln Gln Ile Ser Pro Pro Asn Thr
                405                 410                 415
Asn Ala Lys Ser Tyr Glu Glu Ile Ile Phe Gly Lys Tyr Cys Arg Leu
            420                 425                 430
Ser Pro Arg Asn Thr Leu Ser Val Thr Pro Thr Gly Gln Glu Arg Thr
        435                 440                 445
Ala Met Gly Arg Arg Gly Ile Met Glu Pro Leu Pro His Leu Asn Thr
        450                 455                 460
Arg Leu Glu Val Lys Met Phe Glu Asp Pro Ile Ser Gln Leu Asn Pro
465                 470                 475                 480
Ser Lys Gly Glu Met Asp Pro Gly Gln Ile Asn Met Leu Lys Thr Thr
                485                 490                 495
Lys Phe Asn Ser Glu Cys Arg Gln Pro Gln Ala Ile Pro Ser Ser Val
            500                 505                 510
Arg Asn Glu Gly Lys Pro Tyr Pro Gly Asn Phe Leu Gly Ser Asn Pro
        515                 520                 525
Met Leu Leu Glu Ala Pro Val Asp Ser Ser Pro Leu Ile Arg Ser Asn
        530                 535                 540
Ser Met Pro Thr Ser Ser Ala Thr Asn Leu Ser Val Pro Pro Ser Leu
545                 550                 555                 560
Arg Gly Ser His Ser Phe Asp Glu Arg Met Thr Gly Ser Asp Val
                565                 570                 575
Phe Tyr Pro Gly Thr Val Gly Ile Pro Pro Gln Arg Met Leu Arg Arg
            580                 585                 590
Gln Ala Ala Phe Glu Leu Pro Ser Val Gln Glu Gly His Met Glu Ser
        595                 600                 605
Glu His Pro Ala Arg Val Ser Lys Gly Leu Ala Ser Pro Ser Leu Lys
        610                 615                 620
Glu Lys Lys Leu Leu Pro Gly Asp Arg Pro Gly Tyr Asp Tyr Asp Val
625                 630                 635                 640
Cys Arg Lys Pro Tyr Lys Lys Trp Glu Asp Ser Glu Thr Leu Lys Gln
                645                 650                 655
Ser Tyr Leu Gly Ser Phe Lys Gln Gly Gly Glu Tyr Phe Met Asp Pro
            660                 665                 670
Ser Val Pro Val Gln Gly Val Pro Thr Met Phe Gly Thr Cys Glu
        675                 680                 685
```

```
Asn Arg Lys Arg Arg Lys Glu Lys Ser Val Gly Asp Glu Glu Asp Val
    690             695                 700
Pro Met Ile Cys Gly Gly Met Gly Asn Ala Pro Val Gly Met Met Ser
705             710                 715                 720
Ser Glu Tyr Asp Pro Lys Leu Gln Asp Gly Gly Arg Ser Gly Phe Ala
            725                 730                 735
Met Thr Ala His Glu Ser Leu Ala His Gly His Ser Asp Arg Leu Asp
                740                 745                 750
Pro Ala Arg Pro Gln Leu Pro Ser Arg Ser Pro Ser Leu Gly Ser Glu
        755                 760                 765
Asp Leu Pro Leu Ala Ala Asp Pro Asp Lys Met Thr Asp Leu Gly Lys
    770                 775                 780
Lys Pro Pro Gly Asn Val Ile Ser Val Ile Gln His Thr Asn Ser Leu
785             790                 795                 800
Ser Arg Pro Asn Ser Phe Glu Arg Ser Glu Ser Thr Glu Met Val Ala
            805                 810                 815
Cys Pro Gln Asp Lys Thr Pro Ser Pro Ala Glu Thr Cys Asp Ser Glu
                820                 825                 830
Val Leu Glu Ala Pro Val Ser Pro Glu Trp Ala Pro Pro Gly Asp Gly
        835                 840                 845
Gly Glu Ser Gly Ser Lys Pro Thr Pro Ser Gln Gln Val Pro Gln His
    850                 855                 860
Ser Tyr His Ala Gln Pro Arg Leu Val Arg Gln His Asn Ile Gln Val
865             870                 875                 880
Pro Glu Ile Arg Val Thr Glu Glu Pro Asp Lys Pro Glu Lys Glu Lys
            885                 890                 895
Glu Ala Pro Thr Lys Glu Pro Glu Lys Pro Val Glu Glu Phe Gln Trp
                900                 905                 910
Pro Gln Arg Ser Glu Thr Leu Ser Gln Leu Pro Ala Glu Lys Leu Pro
        915                 920                 925
Pro Lys Lys Lys Arg Leu Arg Leu Ala Asp Leu Glu His Ser Ser Gly
    930                 935                 940
Glu Ser Ser Phe Glu Ser Thr Gly Thr Gly Leu Ser Arg Ser Pro Ser
945             950                 955                 960
Gln Glu Ser Asn Leu Ser His Ser Ser Ser Phe Ser Met Ser Phe Asp
            965                 970                 975
Arg Glu Glu Thr Val Lys Leu Thr Ala Pro Lys Gln Asp Glu Ser
                980                 985                 990
Gly Lys His Ser Glu Phe Leu Thr Val Pro Ala Gly Ser Tyr Ser Leu
        995                 1000                1005
Ser Val Pro Gly His His His Gln Lys Glu Met Arg Arg Cys Ser
    1010            1015                1020
Ser Glu Gln Met Pro Cys Pro His Pro Thr Glu Val Pro Glu Ile
    1025            1030                1035
Arg Ser Lys Ser Phe Asp Tyr Gly Asn Leu Ser His Ala Pro Val
    1040            1045                1050
Ala Gly Thr Ser Pro Ser Thr Leu Ser Pro Ser Arg Glu Arg Lys
    1055            1060                1065
Lys Cys Phe Leu Val Arg Gln Ala Ser Phe Ser Gly Ser Pro Glu
    1070            1075                1080
Ile Ala Gln Gly Glu Ala Gly Val Asp Pro Ser Val Lys Gln Glu
    1085            1090                1095
```

```
His Met Glu His Leu His Ala Gly Leu Arg Ala Ala Trp Ser Ser
    1100                1105                1110

Val Leu Pro Pro Leu Pro Gly Asp Asp Pro Gly Lys Gln Val Gly
    1115                1120                1125

Thr Cys Gly Pro Leu Ser Ser Gly Pro Pro Leu His Leu Thr Gln
    1130                1135                1140

Gln Gln Ile Met His Met Asp Ser Gln Glu Ser Leu Arg Asn Pro
    1145                1150                1155

Leu Ile Gln Pro Thr Ser Tyr Met Thr Ser Lys His Leu Pro Glu
    1160                1165                1170

Gln Pro His Leu Phe Pro His Gln Asp Ala Val Pro Phe Ser Pro
    1175                1180                1185

Ile Gln Asn Ala Leu Phe Gln Phe Gln Tyr Pro Thr Val Cys Met
    1190                1195                1200

Val His Leu Pro Ala Gln Gln Pro Pro Trp Trp Gln Thr His Phe
    1205                1210                1215

Pro His Pro Phe Ala Pro His Pro Gln Asn Ser Tyr Ser Lys Pro
    1220                1225                1230

Pro Phe Gln Ala Asp Leu His Ser Ser Tyr Pro Leu Glu His Val
    1235                1240                1245

Ala Glu His Thr Gly Lys Lys Ser Ala Asp Tyr Pro His Ala Lys
    1250                1255                1260

Glu Gln Thr Tyr Pro Cys Tyr Ser Gly Thr Ser Gly Leu His Ser
    1265                1270                1275

Lys Asn Leu Pro Leu Lys Phe Pro Ser Asp Pro Gly Ser Lys Ser
    1280                1285                1290

Thr Glu Thr Pro Thr Glu Gln Leu Leu Arg Glu Asp Phe Ala Ser
    1295                1300                1305

Glu Asn Ala Gly Pro Leu Gln Ser Leu Pro Gly Thr Val Val Pro
    1310                1315                1320

Val Arg Ile Gln Thr His Val Pro Ser Tyr Gly Ser Val Met Tyr
    1325                1330                1335

Thr Ser Ile Ser Gln Ile Leu Gly Gln Asn Ser Pro Ala Ile Val
    1340                1345                1350

Ile Cys Lys Val Asp Glu Asn Met Thr Gln Arg Thr Leu Val Thr
    1355                1360                1365

Asn Ala Ala Met Gln Gly Ile Gly Leu Asn Ile Ala Gln Val Leu
    1370                1375                1380

Gly Gln His Thr Gly Leu Glu Lys Tyr Pro Leu Trp Lys Val Pro
    1385                1390                1395

Gln Thr Leu Pro Leu Gly Leu Glu Ser Ser Ile Pro Leu Cys Leu
    1400                1405                1410

Pro Ser Thr Ser Asp Asn Ala Ala Ser Leu Gly Ser Lys Arg
    1415                1420                1425

Met Leu Ser Pro Ala Ser Ser Leu Glu Leu Phe Met Glu Thr Lys
    1430                1435                1440

Gln Gln Lys Arg Val Lys Glu Glu Lys Met Tyr Gly Gln Ile Val
    1445                1450                1455

Glu Glu Leu Ser Ala Val Glu Leu Thr Asn Ser Asp Ile Lys Lys
    1460                1465                1470

Gly Leu Ser Arg Pro Gln Lys Pro Gln Leu Val Arg Gln Gly Cys
    1475                1480                1485

Ala Ser Glu Pro Lys Asp Gly Cys Phe Gln Ser Arg Ser Ser Ser
```

```
              1490                1495                1500

Phe  Ser  Ser  Leu  Ser  Pro  Ser  Ser  Gln  Asp  His  Pro  Ser  Ala
            1505                1510                1515

Ser  Gly  Pro  Phe  Pro  Pro  Asn  Arg  Glu  Ile  Leu  Pro  Gly  Ser  Arg
            1520                1525                1530

Ala  Pro  Pro  Arg  Arg  Lys  Phe  Ser  Gly  Pro  Ser  Glu  Ser  Arg  Glu
            1535                1540                1545

Ser  Ser  Asp  Glu  Leu  Asp  Met  Asp  Glu  Thr  Ser  Ser  Asp  Met  Ser
            1550                1555                1560

Met  Ser  Pro  Gln  Ser  Ser  Ala  Leu  Pro  Thr  Gly  Gly  Gly  Gln  Gln
            1565                1570                1575

Glu  Glu  Glu  Gly  Lys  Ala  Arg  Lys  Leu  Pro  Val  Ser  Met  Leu  Val
            1580                1585                1590

His  Met  Ala  Ser  Gly  Pro  Gly  Gly  Asn  Val  Ala  Asn  Ser  Thr  Leu
            1595                1600                1605

Leu  Phe  Thr  Asp  Val  Ala  Asp  Phe  Gln  Gln  Ile  Leu  Gln  Phe  Pro
            1610                1615                1620

Ser  Leu  Arg  Thr  Thr  Thr  Thr  Val  Ser  Trp  Cys  Phe  Leu  Asn  Tyr
            1625                1630                1635

Thr  Lys  Pro  Ser  Phe  Val  Gln  Gln  Ala  Thr  Phe  Lys  Ser  Ser  Val
            1640                1645                1650

Tyr  Ala  Ser  Trp  Cys  Ile  Ser  Ser  Cys  Asn  Pro  Asn  Pro  Ser  Gly
            1655                1660                1665

Leu  Asn  Thr  Lys  Thr  Thr  Leu  Ala  Leu  Leu  Arg  Ser  Lys  Gln  Lys
            1670                1675                1680

Ile  Thr  Ala  Glu  Ile  Tyr  Thr  Leu  Ala  Ala  Met  His  Arg  Pro  Gly
            1685                1690                1695

Ala  Gly  Lys  Leu  Thr  Ser  Ser  Ser  Val  Trp  Lys  Gln  Phe  Ala  Gln
            1700                1705                1710

Met  Lys  Pro  Asp  Ala  Pro  Phe  Leu  Phe  Gly  Asn  Lys  Leu  Glu  Arg
            1715                1720                1725

Lys  Leu  Ala  Gly  Asn  Val  Leu  Lys  Glu  Arg  Gly  Lys  Gly  Glu  Ile
            1730                1735                1740

His  Gly  Asp  Lys  Asp  Leu  Gly  Ser  Lys  Gln  Thr  Glu  Pro  Ile  Arg
            1745                1750                1755

Ile  Lys  Ile  Phe  Glu  Gly  Gly  Tyr  Lys  Ser  Asn  Glu  Asp  Tyr  Val
            1760                1765                1770

Tyr  Val  Arg  Gly  Arg  Gly  Arg  Gly  Lys  Tyr  Ile  Cys  Glu  Glu  Cys
            1775                1780                1785

Gly  Ile  Arg  Cys  Lys  Lys  Pro  Ser  Met  Leu  Lys  Lys  His  Ile  Arg
            1790                1795                1800

Thr  His  Thr  Asp  Val  Arg  Pro  Tyr  Val  Cys  Lys  Leu  Cys  Asn  Phe
            1805                1810                1815

Ala  Phe  Lys  Thr  Lys  Gly  Asn  Leu  Thr  Lys  His  Met  Lys  Ser  Lys
            1820                1825                1830

Ala  His  Met  Lys  Lys  Cys  Leu  Glu  Leu  Gly  Val  Ser  Met  Thr  Ser
            1835                1840                1845

Val  Asp  Asp  Thr  Glu  Thr  Glu  Glu  Ala  Glu  Asn  Met  Glu  Glu  Leu
            1850                1855                1860

His  Lys  Thr  Ser  Glu  Lys  His  Ser  Met  Ser  Gly  Ile  Ser  Thr  Asp
            1865                1870                1875

His  Gln  Phe  Ser  Asp  Ala  Glu  Glu  Ser  Asp  Gly  Glu  Asp  Gly  Asp
            1880                1885                1890
```

```
Asp Asn Asp Asp Asp Glu Asp Asp Asp Phe Asp Asp Gln
    1895                1900            1905

Gly Asp Leu Thr Pro Lys Thr Arg Ser Arg Ser Thr Ser Pro Gln
    1910            1915            1920

Pro Pro Arg Phe Ser Ser Leu Pro Val Asn Val Gly Ala Val Ala
    1925            1930            1935

His Gly Val Pro Ser Asp Ser Ser Leu Gly His Ser Ser Leu Ile
    1940            1945            1950

Ser Tyr Leu Val Thr Leu Pro Ser Ile Gln Val Thr Gln Leu Met
    1955            1960            1965

Thr Pro Ser Asp Ser Cys Asp Asp Thr Gln Met Thr Glu Tyr Gln
    1970            1975            1980

Arg Leu Phe Gln Ser Lys Ser Thr Asp Ser Glu Pro Asp Lys Asp
    1985            1990            1995

Arg Leu Asp Ile Pro Ser Ser Met Asp Glu Glu Ala Met Leu Ser
    2000            2005            2010

Ser Glu Pro Ser Ser Ser Pro Arg Asp Phe Ser Pro Ser Ser Tyr
    2015            2020            2025

Arg Ser Ser Pro Gly Tyr Asp Ser Ser Pro Cys Arg Asp Asn Ser
    2030            2035            2040

Pro Lys Arg Tyr Leu Ile Pro Lys Gly Asp Leu Ser Pro Arg Arg
    2045            2050            2055

His Leu Ser Pro Arg Arg Asp Leu Ser Pro Met Arg His Leu Ser
    2060            2065            2070

Pro Arg Lys Glu Ala Ala Leu Arg Arg Glu Met Ser Gln Gly Asp
    2075            2080            2085

Ala Ser Pro Arg Arg His Leu Ser Pro Arg Arg Pro Leu Ser Pro
    2090            2095            2100

Gly Lys Asp Ile Thr Ala Arg Arg Asp Leu Ser Pro Arg Arg Glu
    2105            2110            2115

Arg Arg Tyr Met Thr Thr Ile Arg Ala Pro Ser Pro Arg Arg Ala
    2120            2125            2130

Leu Tyr Pro Asn Pro Pro Leu Ser Met Gly Gln Tyr Leu Gln Thr
    2135            2140            2145

Glu Pro Ile Val Leu Gly Pro Pro Asn Leu Arg Arg Gly Ile Pro
    2150            2155            2160

Gln Val Pro Tyr Phe Ser Leu Tyr Gly Asp Gln Glu Gly Ala Tyr
    2165            2170            2175

Glu His His Gly Ser Ser Leu Phe Pro Glu Gly Pro Thr Asp Tyr
    2180            2185            2190

Val Phe Ser His Leu Pro Leu His Ser Gln Gln Gln Val Arg Ala
    2195            2200            2205

Pro Ile Pro Met Val Pro Val Gly Gly Ile Gln Met Val His Ser
    2210            2215            2220

Leu Pro Pro Ala Leu Ser Gly Leu His Pro Pro Thr Leu Pro
    2225            2230            2235

Leu Pro Thr Glu Gly Ser Glu Glu Lys Lys Gly Ala Pro Gly Glu
    2240            2245            2250

Ala Phe Ala Lys Asp Pro Tyr Ile Leu Ser Arg Arg His Glu Lys
    2255            2260            2265

Gln Ala Pro Gln Val Leu Gln Ser Ser Gly Leu Pro Ser Ser Pro
    2270            2275            2280
```

```
Ser Ser Pro Arg Leu Leu Met Lys Gln Ser Thr Ser Glu Asp Ser
    2285                2290                2295

Leu Asn Ser Thr Glu Arg Glu Gln Glu Asn Ile Gln Thr Cys
    2300                2305                2310

Thr Lys Ala Ile Ala Ser Leu Arg Ile Ala Thr Glu Glu Ala Ala
    2315                2320                2325

Leu Leu Gly Ala Asp Pro Pro Thr Trp Val Gln Glu Ser Pro Gln
    2330                2335                2340

Lys Pro Leu Glu Ser Ala His Val Ser Ile Arg His Phe Gly Gly
    2345                2350                2355

Pro Glu Pro Gly Gln Pro Cys Thr Ser Ala Ala His Pro Asp Leu
    2360                2365                2370

His Asp Gly Glu Lys Asp Thr Phe Gly Thr Ser Gln Thr Ala Val
    2375                2380                2385

Ala His Pro Thr Phe Tyr Ser Lys Ser Ser Val Asp Glu Lys Arg
    2390                2395                2400

Val Asp Phe Gln Ser Ser Lys Glu Leu Ser Leu Ser Thr Glu Glu
    2405                2410                2415

Gly Asn Glu Pro Ser Pro Glu Lys Asn Gln Leu His
    2420                2425                2430

<210> SEQ ID NO 13
<211> LENGTH: 342
<212> TYPE: PRT
<213> ORGANISM: Mus musculus

<400> SEQUENCE: 13

Met Ser Arg Val Leu Val Gly Ala Gly Leu Thr Gly Ser Leu Cys
1               5                   10                  15

Ala Ala Leu Leu Arg Lys Glu Ile Thr Ala Pro Leu Tyr Leu Gly Leu
                20                  25                  30

Trp Asp Lys Gly Gly Asp Ile Gly Gly Arg Met Ile Thr Ala Ser Ser
                35                  40                  45

Pro His Asn Pro Arg Cys Thr Ala Asp Leu Gly Ala Gln Tyr Ile Thr
    50                  55                  60

Cys Ser Pro His Tyr Val Lys Glu His Gln Asn Phe Tyr Glu Glu Leu
65                  70                  75                  80

Leu Ala His Gly Ile Leu Lys Pro Leu Thr Ser Pro Ile Glu Gly Met
                85                  90                  95

Lys Gly Lys Glu Gly Asp Cys Asn Phe Val Ala Pro Gln Gly Phe Ser
                100                 105                 110

Ser Val Ile Lys Tyr Tyr Leu Lys Lys Ser Gly Ala Glu Val Ser Leu
                115                 120                 125

Lys His Cys Val Thr Gln Ile His Leu Lys Asp Asn Lys Trp Glu Val
                130                 135                 140

Ser Thr Asp Thr Gly Ser Ala Glu Gln Phe Asp Leu Val Ile Leu Thr
145                 150                 155                 160

Met Pro Ala Pro Gln Ile Leu Glu Leu Gln Gly Asp Ile Val Asn Leu
                165                 170                 175

Ile Ser Glu Arg Gln Arg Glu Gln Leu Lys Ser Val Tyr Ser Ser
                180                 185                 190

Arg Tyr Ala Leu Gly Leu Phe Tyr Glu Val Gly Met Lys Ile Gly Val
                195                 200                 205

Pro Trp Ser Cys Arg Tyr Leu Ser Ser His Pro Cys Ile Cys Phe Ile
                210                 215                 220
```

-continued

```
Ser Ile Asp Asn Lys Lys Arg Asn Ile Glu Ser Ser Glu Cys Gly Pro
225                 230                 235                 240

Ser Val Val Ile Gln Thr Thr Val Pro Phe Gly Val Gln His Leu Glu
                245                 250                 255

Ala Ser Glu Ala Asp Val Gln Lys Leu Met Ile Gln Gln Leu Glu Thr
            260                 265                 270

Ile Leu Pro Gly Leu Pro Gln Pro Val Ala Thr Ile Cys His Lys Trp
        275                 280                 285

Thr Tyr Ser Gln Val Thr Ser Ser Val Ser Asp Arg Pro Gly Gln Met
    290                 295                 300

Thr Leu His Leu Lys Pro Phe Leu Val Cys Gly Gly Asp Gly Phe Thr
305                 310                 315                 320

His Ser Asn Phe Asn Gly Cys Ile Ser Ser Ala Leu Ser Val Met Lys
                325                 330                 335

Val Leu Lys Arg Tyr Ile
            340

<210> SEQ ID NO 14
<211> LENGTH: 563
<212> TYPE: PRT
<213> ORGANISM: Mus musculus

<400> SEQUENCE: 14

Met Thr Asp Glu Gly Asp Leu Ala Gln Glu Asp Thr Ala Lys Asp Glu
1               5                   10                  15

Gly Asn Val Thr Glu Gly Ser Arg Met Ser Lys Leu Arg Arg Ala Arg
            20                  25                  30

Arg Lys Val Thr Lys Pro His Leu Cys Ser Met Asp Gly Glu Glu Ile
        35                  40                  45

Ala Lys Ala Asn Ser Ser Glu Met Ser Arg Asn Gln Ile Ala Asp Leu
    50                  55                  60

Ser Lys Pro Gly Ser Ala Glu Ser Trp Ser Ser His Ser Ala Lys Asp
65                  70                  75                  80

Ala Tyr His Pro Thr Pro Val Val Lys Pro Ser Leu Pro Ser Ala Leu
                85                  90                  95

Ala Gly Ala Pro Asp Ala Glu Phe Ser Pro Asn Thr Asp Pro Thr Arg
            100                 105                 110

Tyr Asn Ala Gln Ser Phe Asn Pro Pro Gln Leu Ser Ala Arg Met Lys
        115                 120                 125

His Ile Lys Gln Glu Met Ala Lys Asn His Leu Gln Phe Val Arg Phe
    130                 135                 140

Glu Ala Thr Asp Leu His Gly Val Ser Arg Ser Lys Ser Ile Pro Ala
145                 150                 155                 160

Gln Phe Phe Gln Glu Lys Val Ile His Gly Val Phe Met Pro Arg Gly
                165                 170                 175

Tyr Leu Glu Leu Met Pro Asn Pro Lys Asp Asn Glu Val Asn His Ile
            180                 185                 190

Arg Ala Thr Cys Phe Asn Ser Asp Ile Val Leu Met Pro Glu Leu Ser
        195                 200                 205

Thr Phe Arg Val Leu Pro Trp Ala Glu Arg Thr Ala Arg Val Ile Cys
    210                 215                 220

Asp Thr Phe Thr Val Thr Gly Glu Pro Leu Leu Thr Ser Pro Arg Tyr
225                 230                 235                 240

Ile Ala Lys Arg Gln Leu Arg Gln Leu Gln Asp Ala Gly Phe Cys Leu
```

```
                    245                 250                 255
Leu Ser Ala Phe Ile Tyr Asp Phe Cys Ile Phe Gly Val Pro Glu Val
            260                 265                 270

Ile Asn Ser Lys Thr Ile Ser Phe Pro Ala Ser Thr Leu Leu Ser Asn
            275                 280                 285

His Asp Gln Pro Phe Met Gln Glu Leu Val Glu Gly Leu Tyr Gln Thr
            290                 295                 300

Gly Ala Asn Val Glu Ser Phe Ser Ser Thr Arg Pro Gly Gln Met
305                 310                 315                 320

Glu Ile Cys Phe Leu Pro Glu Phe Gly Ile Ser Ser Ala Asp Asn Ala
                325                 330                 335

Phe Thr Leu Arg Thr Gly Leu Gln Glu Val Ala Arg Arg Tyr Asn Tyr
                340                 345                 350

Ile Ala Ser Leu Val Ile Glu Thr Gly Phe Cys Asn Ser Gly Ile Leu
                355                 360                 365

Ser His Ser Ile Trp Asp Val Gly Gly Lys Thr Asn Met Phe Cys Ser
            370                 375                 380

Gly Ser Gly Val Glu Arg Leu Thr Leu Thr Gly Lys Lys Trp Leu Ala
385                 390                 395                 400

Gly Leu Leu Lys His Ser Ala Ala Leu Ser Cys Leu Met Ala Pro Ala
                405                 410                 415

Val Asn Cys Arg Lys Arg Tyr Cys Lys Asp Ser Arg Asp Leu Lys Asp
                420                 425                 430

Ser Val Pro Thr Thr Trp Gly Tyr Asn Asp Asn Ser Cys Ala Leu Asn
                435                 440                 445

Ile Lys Cys His Gly Glu Lys Gly Thr Gln Ile Glu Asn Lys Leu Gly
            450                 455                 460

Ser Ala Thr Ala Asn Pro Tyr Leu Val Leu Ala Ala Thr Val Ala Ala
465                 470                 475                 480

Gly Leu Asp Gly Leu Gln Ser Ser Asp Gly Ala Ala Ala Gly Ser Asp
                485                 490                 495

Glu Ser Gln Asp Leu Tyr Gln Pro Glu Pro Ser Glu Ile Pro Leu Lys
                500                 505                 510

Met Glu Asp Ala Leu Ala Ala Leu Glu Gln Asp Glu Cys Leu Lys Gln
            515                 520                 525

Ala Leu Gly Glu Thr Phe Ile Arg Tyr Phe Val Ala Met Lys Lys Tyr
                530                 535                 540

Glu Leu Glu Asn Glu Glu Thr Asp Ala Glu Gly Asn Lys Phe Leu Glu
545                 550                 555                 560

Tyr Phe Ile

<210> SEQ ID NO 15
<211> LENGTH: 2671
<212> TYPE: PRT
<213> ORGANISM: Mus musculus

<400> SEQUENCE: 15

Met Ala Ala Asp Thr Gln Val Ser Glu Thr Leu Lys Arg Phe Ala Val
1               5                   10                  15

Lys Val Thr Thr Ala Ser Val Lys Glu Arg Arg Glu Ile Leu Ser Glu
            20                  25                  30

Leu Gly Arg Cys Ile Ala Gly Lys Asp Leu Pro Glu Gly Ala Val Lys
            35                  40                  45

Gly Leu Cys Lys Leu Phe Cys Leu Thr Leu His Arg Tyr Arg Asp Ala
```

```
            50                  55                  60
Ala Ser Arg Arg Ala Leu Gln Ala Ala Ile Gln Gln Leu Ala Glu Ala
 65                  70                  75                  80

Gln Pro Glu Ala Thr Ala Lys Asn Leu Leu His Ser Leu Gln Ser Ser
                     85                  90                  95

Gly Val Gly Ser Lys Ala Cys Val Pro Ser Lys Ser Gly Ser Ala
                100                 105                 110

Ala Leu Leu Ala Leu Thr Trp Thr Cys Leu Leu Val Arg Ile Val Phe
                115                 120                 125

Pro Leu Lys Ala Lys Arg Gln Gly Asp Ile Trp Asn Lys Leu Val Glu
130                 135                 140

Val Gln Cys Leu Leu Leu Glu Val Leu Gly Gly Ser His Lys His
145                 150                 155                 160

Ala Val Asp Gly Ala Val Lys Lys Leu Thr Lys Leu Trp Lys Glu Asn
                165                 170                 175

Pro Gly Leu Val Glu Gln Tyr Phe Ser Ala Ile Leu Ser Leu Glu Pro
                180                 185                 190

Ser Gln Asn Tyr Ala Ala Met Leu Gly Leu Leu Val Gln Phe Cys Thr
                195                 200                 205

Asn His Lys Glu Met Asp Ala Val Ser Gln His Lys Ser Thr Leu Leu
                210                 215                 220

Glu Phe Tyr Val Lys Asn Ile Leu Met Ser Lys Ala Lys Pro Pro Lys
225                 230                 235                 240

Tyr Leu Leu Asp Asn Cys Ala Pro Leu Leu Arg Phe Met Ser His Ser
                245                 250                 255

Glu Phe Lys Asp Leu Ile Leu Pro Thr Ile Gln Lys Ser Leu Leu Arg
                260                 265                 270

Ser Pro Glu Asn Val Ile Glu Thr Ile Ser Ser Leu Leu Ala Ser Val
                275                 280                 285

Thr Leu Asp Leu Ser Gln Tyr Ala Leu Asp Ile Val Lys Gly Leu Ala
                290                 295                 300

Asn Gln Leu Lys Ser Asn Ser Pro Arg Leu Met Asp Glu Ala Val Leu
305                 310                 315                 320

Ala Leu Arg Asn Leu Ala Arg Gln Cys Ser Asp Ser Ala Thr Glu
                325                 330                 335

Ala Leu Thr Lys His Leu Phe Ala Ile Leu Gly Gly Ser Glu Gly Lys
                340                 345                 350

Leu Thr Ile Ile Ala Gln Lys Met Ser Val Leu Ser Gly Ile Gly Ser
                355                 360                 365

Leu Ser His His Val Val Ser Gly Pro Ser Gly Gln Val Leu Asn Gly
                370                 375                 380

Cys Val Ala Glu Leu Phe Ile Pro Phe Leu Gln Glu Val His Glu
385                 390                 395                 400

Gly Thr Leu Val His Ala Val Ser Ile Leu Ala Leu Trp Cys Asn Arg
                405                 410                 415

Phe Thr Thr Glu Val Pro Lys Lys Leu Thr Asp Trp Phe Lys Lys Val
                420                 425                 430

Phe Ser Leu Lys Thr Ser Thr Ser Ala Val Arg His Ala Tyr Leu Gln
                435                 440                 445

Cys Met Leu Ala Ser Phe Arg Gly Asp Thr Leu Leu Gln Ala Leu Asp
                450                 455                 460

Phe Leu Pro Leu Leu Met Gln Thr Val Glu Lys Ala Ala Ser Gln Gly
465                 470                 475                 480
```

```
Thr Gln Val Pro Thr Val Thr Glu Gly Val Ala Ala Leu Leu Leu
            485                 490                 495

Ser Lys Leu Ser Val Ala Asp Ala Gln Ala Glu Ala Lys Leu Ser Gly
            500                 505                 510

Phe Trp Gln Leu Val Val Asp Glu Lys Arg Gln Thr Phe Thr Ser Glu
            515                 520                 525

Lys Phe Leu Leu Leu Ala Ser Glu Asp Ala Leu Cys Thr Val Leu Arg
            530                 535                 540

Leu Thr Glu Arg Leu Phe Leu Asp His Pro His Arg Leu Thr Asn Ser
545                 550                 555                 560

Lys Val Gln Gln Tyr Tyr Arg Val Leu Ala Val Leu Leu Ser Arg
                565                 570                 575

Thr Trp His Val Arg Arg Gln Ala Gln Gln Thr Val Arg Lys Leu Leu
            580                 585                 590

Ser Ser Leu Gly Gly Val Lys Leu Ala Asn Gly Leu Leu Asp Glu Leu
            595                 600                 605

Lys Thr Val Leu Asn Ser His Lys Val Leu Pro Leu Glu Ala Leu Val
            610                 615                 620

Thr Asp Ala Gly Glu Val Thr Glu Met Gly Lys Thr Tyr Val Pro Pro
625                 630                 635                 640

Arg Val Leu Gln Glu Ala Leu Cys Val Ile Ser Gly Val Pro Gly Leu
                645                 650                 655

Lys Gly Asp Ile Pro Ser Thr Glu Gln Leu Ala Gln Glu Met Leu Ile
                660                 665                 670

Ile Ser His His Pro Ser Leu Val Ala Val Gln Ser Gly Leu Trp Pro
                675                 680                 685

Ala Leu Leu Thr Arg Met Lys Ile Asp Pro Asp Ala Phe Ile Thr Arg
            690                 695                 700

His Leu Asp Gln Ile Ile Pro Arg Ile Thr Thr Gln Ser Pro Leu Asn
705                 710                 715                 720

Gln Ser Ser Met Asn Ala Met Gly Ser Leu Ser Val Leu Ser Pro Asp
                725                 730                 735

Arg Val Leu Pro Gln Leu Ile Ser Thr Ile Thr Ala Ser Val Gln Asn
            740                 745                 750

Pro Ala Leu Cys Leu Val Thr Arg Glu Glu Phe Ser Ile Met Gln Thr
            755                 760                 765

Pro Ala Gly Glu Leu Phe Asp Lys Ser Ile Ile Gln Ser Ala Gln Gln
            770                 775                 780

Asp Ser Ile Lys Lys Ala Asn Met Lys Arg Glu Asn Lys Ala Tyr Ser
785                 790                 795                 800

Phe Lys Glu Gln Ile Ile Glu Met Glu Leu Lys Glu Glu Ile Lys Lys
                805                 810                 815

Lys Lys Gly Ile Lys Glu Glu Val Gln Leu Thr Ser Lys Gln Lys Glu
                820                 825                 830

Met Leu Gln Ala Gln Met Asp Lys Glu Ala Gln Ile Arg Arg Arg Leu
            835                 840                 845

Gln Glu Leu Asp Gly Glu Leu Glu Ala Ala Leu Gly Leu Leu Asp Ala
            850                 855                 860

Ile Met Ala Arg Asn Pro Cys Gly Leu Ile Gln Tyr Ile Pro Val Leu
865                 870                 875                 880

Val Asp Ala Phe Leu Pro Leu Leu Lys Ser Pro Leu Ala Pro Arg
                885                 890                 895
```

```
Val Lys Gly Pro Phe Leu Ser Leu Ala Ala Cys Val Met Pro Arg
            900                 905                 910

Leu Lys Thr Leu Gly Thr Leu Val Ser His Val Thr Leu Arg Leu Leu
        915                 920                 925

Lys Pro Glu Cys Ala Leu Asp Lys Ser Trp Cys Gln Glu Glu Leu Pro
        930                 935                 940

Val Ala Val Arg Arg Ala Val Ser Leu Leu His Thr His Thr Ile Pro
945                 950                 955                 960

Ser Arg Val Gly Lys Gly Glu Pro Asp Ala Ala Pro Leu Ser Ala Pro
                965                 970                 975

Ala Phe Ser Leu Val Phe Pro Met Leu Lys Met Val Leu Thr Glu Met
            980                 985                 990

Pro Tyr His Ser Glu Glu Glu Glu Gln Met Ala Gln Ile Leu Gln
            995                 1000                1005

Ile Leu Thr Val His Ala Gln Leu Arg Ala Ser Pro Asp Thr Pro
    1010                1015                1020

Pro Glu Arg Val Asp Glu Asn Gly Pro Glu Leu Leu Pro Arg Val
    1025                1030                1035

Ala Met Leu Arg Leu Leu Thr Trp Val Ile Gly Thr Gly Ser Pro
    1040                1045                1050

Arg Leu Gln Val Leu Ala Ser Asp Thr Leu Thr Ala Leu Cys Ala
    1055                1060                1065

Ser Ser Ser Gly Glu Asp Gly Cys Ala Phe Ala Glu Gln Glu Glu
    1070                1075                1080

Val Asp Val Leu Leu Ala Ala Leu Gln Ser Pro Cys Ala Ser Val
    1085                1090                1095

Arg Glu Thr Ala Leu Arg Gly Leu Met Glu Leu Arg Leu Val Leu
    1100                1105                1110

Pro Ser Pro Asp Thr Asp Glu Lys Ser Gly Leu Ser Leu Leu Arg
    1115                1120                1125

Arg Leu Trp Val Ile Lys Phe Asp Lys Glu Asp Glu Ile Arg Lys
    1130                1135                1140

Leu Ala Glu Arg Leu Trp Ser Thr Met Gly Leu Asp Leu Gln Ser
    1145                1150                1155

Asp Leu Cys Ser Leu Leu Ile Asp Asp Val Ile Tyr His Glu Ala
    1160                1165                1170

Ala Val Arg Gln Ala Gly Ala Glu Ala Leu Ser Gln Ala Val Ala
    1175                1180                1185

Arg Tyr Gln Arg Gln Ala Ala Glu Val Met Gly Arg Leu Met Glu
    1190                1195                1200

Ile Tyr Gln Glu Lys Leu Tyr Arg Pro Pro Val Leu Asp Ala
    1205                1210                1215

Leu Gly Arg Val Ile Ser Glu Ser Pro Pro Asp Gln Trp Glu Ala
    1220                1225                1230

Arg Cys Gly Leu Ala Leu Ala Leu Asn Lys Leu Ser Gln Tyr Leu
    1235                1240                1245

Asp Ser Ser Gln Val Lys Pro Leu Phe Gln Phe Phe Val Pro Asp
    1250                1255                1260

Ala Leu Asn Asp Arg Asn Pro Asp Val Arg Lys Cys Met Leu Asp
    1265                1270                1275

Ala Ala Leu Ala Thr Leu Asn Ala His Gly Lys Glu Asn Val Asn
    1280                1285                1290

Ser Leu Leu Pro Val Phe Glu Glu Phe Leu Lys Asp Ala Pro Asn
```

```
            1295                1300                1305

Asp Ala Ser Tyr Asp Ala Val Arg Gln Ser Val Val Val Leu Met
    1310                1315                1320

Gly Ser Leu Ala Lys His Leu Asp Lys Ser Asp Pro Lys Val Lys
    1325                1330                1335

Pro Ile Val Ala Lys Leu Ile Ala Ala Leu Ser Thr Pro Ser Gln
    1340                1345                1350

Gln Val Gln Glu Ser Val Ala Ser Cys Leu Pro Pro Leu Val Pro
    1355                1360                1365

Ala Val Lys Glu Asp Ala Gly Gly Met Ile Gln Arg Leu Met Gln
    1370                1375                1380

Gln Leu Leu Glu Ser Asp Lys Tyr Ala Glu Arg Lys Gly Ala Ala
    1385                1390                1395

Tyr Gly Leu Ala Gly Leu Val Lys Gly Leu Gly Ile Leu Ser Leu
    1400                1405                1410

Lys Gln Gln Glu Met Met Ala Ala Leu Thr Asp Ala Ile Gln Asp
    1415                1420                1425

Lys Lys Asn Phe Arg Arg Arg Glu Gly Ala Leu Phe Ala Phe Glu
    1430                1435                1440

Met Leu Cys Thr Met Leu Gly Lys Leu Phe Glu Pro Tyr Val Val
    1445                1450                1455

His Val Leu Pro His Leu Leu Leu Cys Phe Gly Asp Gly Asn Gln
    1460                1465                1470

Tyr Val Arg Glu Ala Ala Asp Asp Cys Ala Lys Ala Val Met Ser
    1475                1480                1485

Asn Leu Ser Ala His Gly Val Lys Leu Val Leu Pro Ser Leu Leu
    1490                1495                1500

Ala Ala Leu Glu Glu Glu Ser Trp Arg Thr Lys Ala Gly Ser Val
    1505                1510                1515

Glu Leu Leu Gly Ala Met Ala Tyr Cys Ala Pro Lys Gln Leu Ser
    1520                1525                1530

Ser Cys Leu Pro Asn Ile Val Pro Lys Leu Thr Glu Val Leu Thr
    1535                1540                1545

Asp Ser His Val Lys Val Gln Lys Ala Gly Gln Gln Ala Leu Arg
    1550                1555                1560

Gln Ile Gly Ser Val Ile Arg Asn Pro Glu Ile Leu Ala Ile Ala
    1565                1570                1575

Pro Val Leu Leu Asp Ala Leu Thr Asp Pro Ser Arg Lys Thr Gln
    1580                1585                1590

Lys Cys Leu Gln Thr Leu Leu Asp Thr Lys Phe Val His Phe Ile
    1595                1600                1605

Asp Ala Pro Ser Leu Ala Leu Ile Met Pro Ile Val Gln Arg Ala
    1610                1615                1620

Phe Gln Asp Arg Ser Thr Asp Thr Arg Lys Met Ala Ala Gln Ile
    1625                1630                1635

Ile Gly Asn Met Tyr Ser Leu Thr Asp Gln Lys Asp Leu Ala Pro
    1640                1645                1650

Tyr Leu Pro Ser Val Thr Pro Gly Leu Lys Ala Ser Leu Leu Asp
    1655                1660                1665

Pro Val Pro Glu Val Arg Thr Val Ser Ala Lys Ala Leu Gly Ala
    1670                1675                1680

Met Val Lys Gly Met Gly Glu Ser Cys Phe Glu Asp Leu Leu Pro
    1685                1690                1695
```

-continued

Trp Leu Met Glu Thr Leu Thr Tyr Glu Gln Ser Ser Val Asp Arg
1700                1705                1710

Ser Gly Ala Ala Gln Gly Leu Ala Glu Val Met Ala Gly Leu Gly
1715                1720                1725

Val Glu Lys Leu Glu Lys Leu Met Pro Glu Ile Val Ala Thr Ala
1730                1735                1740

Ser Lys Val Asp Ile Ala Pro His Val Arg Asp Gly Tyr Ile Met
1745                1750                1755

Met Phe Asn Tyr Leu Pro Ile Thr Phe Gly Asp Lys Phe Thr Pro
1760                1765                1770

Tyr Val Gly Pro Ile Ile Pro Cys Ile Leu Lys Ala Leu Ala Asp
1775                1780                1785

Glu Asn Glu Phe Val Arg Asp Thr Ala Leu Arg Ala Gly Gln Arg
1790                1795                1800

Val Ile Ser Met Tyr Ala Glu Thr Ala Ile Ala Leu Leu Leu Pro
1805                1810                1815

Gln Leu Glu Gln Gly Leu Phe Asp Asp Leu Trp Arg Ile Arg Phe
1820                1825                1830

Ser Ser Val Gln Leu Leu Gly Asp Leu Leu Phe His Ile Ser Gly
1835                1840                1845

Val Thr Gly Lys Met Thr Thr Glu Thr Ala Ser Glu Asp Asp Asn
1850                1855                1860

Phe Gly Thr Ala Gln Ser Asn Lys Ala Ile Ile Thr Ala Leu Gly
1865                1870                1875

Val Asp Arg Arg Asn Arg Val Leu Ala Gly Leu Tyr Met Gly Arg
1880                1885                1890

Ser Asp Thr Gln Leu Val Val Arg Gln Ala Ser Leu His Val Trp
1895                1900                1905

Lys Ile Val Val Ser Asn Thr Pro Arg Thr Leu Arg Glu Ile Leu
1910                1915                1920

Pro Thr Leu Phe Gly Leu Leu Gly Phe Leu Ala Ser Thr Cys
1925                1930                1935

Ala Asp Lys Arg Thr Ile Ala Ala Arg Thr Leu Gly Asp Leu Val
1940                1945                1950

Arg Lys Leu Gly Glu Lys Ile Leu Pro Glu Ile Ile Pro Ile Leu
1955                1960                1965

Glu Glu Gly Leu Arg Ser Gln Lys Ser Asp Glu Arg Gln Gly Val
1970                1975                1980

Cys Ile Gly Leu Ser Glu Ile Met Lys Ser Thr Ser Arg Asp Ala
1985                1990                1995

Val Leu Phe Phe Ser Glu Ser Leu Val Pro Thr Ala Arg Lys Ala
2000                2005                2010

Leu Cys Asp Pro Leu Glu Glu Val Arg Glu Ala Ala Ala Lys Thr
2015                2020                2025

Phe Glu Gln Leu His Ser Thr Ile Gly His Gln Ala Leu Glu Asp
2030                2035                2040

Ile Leu Pro Phe Leu Leu Lys Gln Leu Asp Asp Glu Glu Val Ser
2045                2050                2055

Glu Phe Ala Leu Asp Gly Leu Lys Gln Val Met Ala Val Lys Ser
2060                2065                2070

Arg Val Val Leu Pro Tyr Leu Val Pro Lys Leu Thr Thr Pro Pro
2075                2080                2085

```
Val Asn Thr Arg Val Leu Ala Phe Leu Ser Ser Val Ala Gly Asp
2090                2095                2100

Ala Leu Thr Arg His Leu Gly Val Ile Leu Pro Ala Val Met Leu
2105                2110                2115

Ala Leu Lys Glu Lys Leu Gly Thr Pro Asp Glu Gln Leu Glu Met
2120                2125                2130

Ala Asn Cys Gln Ala Val Ile Leu Ser Val Glu Asp Asp Thr Gly
2135                2140                2145

His Arg Ile Ile Ile Glu Asp Leu Leu Glu Ala Thr Arg Ser Pro
2150                2155                2160

Glu Val Gly Met Arg Gln Ala Ala Ile Ile Leu Asn Met Tyr
2165                2170                2175

Cys Ser Arg Ser Lys Ala Asp Tyr Ser Ser His Leu Arg Ser Leu
2180                2185                2190

Val Ser Gly Leu Ile Arg Leu Phe Asn Asp Ser Ser Pro Val Val
2195                2200                2205

Leu Glu Glu Ser Trp Asp Ala Leu Asn Ala Ile Thr Lys Lys Leu
2210                2215                2220

Asp Ala Gly Asn Gln Leu Ala Leu Ile Glu Glu Leu His Lys Glu
2225                2230                2235

Ile Arg Phe Ile Gly Asn Glu Cys Lys Gly Glu His Val Pro Gly
2240                2245                2250

Phe Cys Leu Pro Lys Arg Gly Val Thr Ser Ile Leu Pro Val Leu
2255                2260                2265

Arg Glu Gly Val Leu Thr Gly Ser Pro Glu Gln Lys Glu Glu Ala
2270                2275                2280

Ala Lys Gly Leu Gly Leu Val Ile Arg Leu Thr Ser Ala Asp Ala
2285                2290                2295

Leu Arg Pro Ser Val Val Ser Ile Thr Gly Pro Leu Ile Arg Ile
2300                2305                2310

Leu Gly Asp Arg Phe Asn Trp Thr Val Lys Ala Ala Leu Leu Glu
2315                2320                2325

Thr Leu Ser Leu Leu Leu Gly Lys Val Gly Ile Ala Leu Lys Pro
2330                2335                2340

Phe Leu Pro Gln Leu Gln Thr Thr Phe Thr Lys Ala Leu Gln Asp
2345                2350                2355

Ser Asn Arg Gly Val Arg Leu Lys Ala Ala Asp Ala Leu Gly Lys
2360                2365                2370

Leu Ile Ser Ile His Val Lys Val Asp Pro Leu Phe Thr Glu Leu
2375                2380                2385

Leu Asn Gly Ile Arg Ala Val Glu Asp Pro Gly Ile Arg Asp Thr
2390                2395                2400

Met Leu Gln Ala Leu Arg Phe Val Ile Gln Gly Ala Gly Ser Lys
2405                2410                2415

Val Asp Ala Ala Ile Arg Lys Asn Leu Val Ser Leu Leu Leu Ser
2420                2425                2430

Met Leu Gly His Asp Glu Asp Asn Thr Arg Ile Ser Thr Ala Gly
2435                2440                2445

Cys Leu Gly Glu Leu Cys Ala Phe Leu Thr Asp Glu Glu Leu Asn
2450                2455                2460

Thr Val Leu Gln Gln Cys Leu Leu Ala Asp Val Ser Gly Ile Asp
2465                2470                2475

Trp Met Val Arg His Gly Arg Ser Leu Ala Leu Ser Val Ala Val
```

```
                    2480                2485                2490
Asn Val Ala Pro Ser Arg Leu Cys Ala Gly Arg Tyr Ser Asn Glu
    2495                2500                2505

Val Gln Asp Met Ile Leu Ser Asn Ala Val Ala Asp Arg Ile Pro
    2510                2515                2520

Ile Ala Met Ser Gly Ile Arg Gly Met Gly Phe Leu Met Lys Tyr
    2525                2530                2535

His Ile Glu Thr Gly Ser Gly Gln Leu Pro Pro Arg Leu Ser Ser
    2540                2545                2550

Leu Leu Ile Lys Cys Leu Gln Asn Pro Cys Ser Asp Ile Arg Leu
    2555                2560                2565

Val Ala Glu Lys Met Ile Trp Trp Ala Asn Lys Glu Pro Arg Pro
    2570                2575                2580

Pro Leu Glu Pro Gln Thr Ile Lys Pro Ile Leu Lys Ala Leu Leu
    2585                2590                2595

Asp Asn Thr Lys Asp Lys Asn Thr Val Val Arg Ala Tyr Ser Asp
    2600                2605                2610

Gln Ala Ile Val Asn Leu Leu Lys Met Arg Arg Gly Glu Glu Leu
    2615                2620                2625

Leu Gln Ser Leu Ser Lys Ile Leu Asp Val Ala Ser Leu Glu Ala
    2630                2635                2640

Leu Asn Glu Cys Ser Arg Arg Ser Leu Arg Lys Leu Ala Cys Gln
    2645                2650                2655

Ala Asp Ser Val Glu Gln Val Asp Asp Thr Ile Leu Thr
    2660                2665                2670

<210> SEQ ID NO 16
<211> LENGTH: 1403
<212> TYPE: PRT
<213> ORGANISM: Mus musculus

<400> SEQUENCE: 16

Met Ser Ala Ser Gly Asp Gly Thr Arg Val Pro Pro Lys Ser Lys Gly
1               5                   10                  15

Lys Thr Leu Ser Ser Phe Phe Gly Ser Leu Pro Gly Ser Ser Ala
                20                  25                  30

Arg Asn Leu Val Ser His Thr His Ser Ser Thr Ser Thr Lys Asp Leu
            35                  40                  45

Gln Thr Ala Thr Asp Pro Ser Gly Thr Pro Ala Pro Ser Ser Lys Val
        50                  55                  60

Ser Thr Asn Ser Gln Met Ala Gly Asp Ala Ala Gly Leu Leu Gln Pro
65                  70                  75                  80

Ser Glu Gln Thr Ala Gly Asp Lys Asp Met Gly Ser Phe Ser Val Thr
                85                  90                  95

Ser Ser Glu Asp Ala Phe Ser Gly Val Phe Gly Ile Met Asp Ala Ala
                100                 105                 110

Lys Gly Met Val Gln Gly Gly Leu Gly Ala Thr Gln Ser Ala Leu Val
            115                 120                 125

Gly Thr Lys Glu Ala Val Ser Gly Gly Val Met Gly Ala Val Gly Val
        130                 135                 140

Ala Lys Gly Leu Val Lys Gly Gly Leu Asp Thr Ser Lys Asn Val Leu
145                 150                 155                 160

Thr Asn Thr Lys Asp Thr Val Thr Thr Gly Val Met Gly Ala Ala Asn
                165                 170                 175
```

-continued

```
Met Ala Lys Gly Thr Val Gln Thr Gly Leu Asp Thr Thr Lys Ser Val
            180                 185                 190

Val Met Gly Thr Lys Asp Thr Val Ala Thr Gly Leu Ala Gly Ala Val
        195                 200                 205

Asn Val Ala Lys Gly Thr Ile Gln Gly Gly Leu Asp Thr Thr Lys Ser
    210                 215                 220

Val Val Met Gly Thr Lys Asp Thr Val Thr Thr Gly Leu Thr Gly Ala
225                 230                 235                 240

Val Asn Val Ala Lys Gly Val Val Gln Gly Gly Leu Asp Thr Thr Lys
                245                 250                 255

Ser Val Val Met Gly Thr Lys Asp Thr Val Thr Thr Gly Leu Thr Gly
            260                 265                 270

Ala Met Asn Val Ala Lys Gly Thr Ala Gln Met Gly Ile Asp Thr Ser
        275                 280                 285

Lys Thr Val Leu Thr Gly Thr Lys Asp Thr Val Cys Ala Gly Ala Thr
    290                 295                 300

Gly Ala Ile Asn Val Ala Lys Gly Ala Ala Gln Gly Gly Leu Asp Thr
305                 310                 315                 320

Thr Lys Ser Val Leu Ile Gly Thr Lys Asp Thr Val Thr Thr Gly Leu
                325                 330                 335

Thr Gly Ala Val Asn Val Ala Lys Gly Ala Val Gln Gly Gly Leu Asp
            340                 345                 350

Thr Thr Lys Ser Val Val Met Gly Thr Lys Asp Thr Val Thr Thr Gly
        355                 360                 365

Leu Thr Gly Ala Met Asn Val Ala Lys Gly Thr Ala Gln Met Gly Leu
    370                 375                 380

Gly Thr Ser Lys Thr Val Leu Thr Gly Thr Lys Asp Thr Val Cys Ala
385                 390                 395                 400

Gly Leu Thr Gly Ala Ile Asn Val Ala Lys Gly Ala Ala Gln Gly Gly
                405                 410                 415

Leu Asp Thr Thr Lys Ser Val Leu Met Gly Thr Lys Asp Thr Val Thr
            420                 425                 430

Thr Gly Leu Thr Gly Ala Val Asn Val Ala Lys Gly Thr Ile Gln Gly
        435                 440                 445

Gly Leu Asp Thr Thr Lys Ser Val Val Met Gly Thr Lys Asp Thr Val
    450                 455                 460

Thr Thr Gly Leu Thr Gly Ala Val Asn Val Ala Lys Gly Thr Ile Gln
465                 470                 475                 480

Gly Gly Leu Asp Thr Thr Lys Ser Val Val Met Gly Thr Lys Asp Thr
                485                 490                 495

Val Thr Thr Gly Leu Thr Gly Ala Val Asn Val Ala Lys Gly Ala Ala
            500                 505                 510

Gln Gly Gly Leu Asp Thr Thr Lys Ser Val Val Met Gly Thr Lys Asp
        515                 520                 525

Thr Val Thr Thr Gly Leu Thr Gly Ala Met Asn Val Ala Lys Gly Thr
    530                 535                 540

Ala Gln Met Gly Leu Gly Thr Ser Lys Thr Val Leu Thr Gly Thr Lys
545                 550                 555                 560

Asp Thr Val Cys Ala Gly Leu Thr Gly Ala Ile Asn Val Ala Lys Gly
                565                 570                 575

Ala Ala Gln Gly Gly Leu Asp Thr Thr Lys Ser Val Leu Met Gly Thr
            580                 585                 590

Lys Asp Thr Val Thr Thr Gly Leu Thr Gly Ala Val Asn Val Ala Lys
```

```
            595                 600                 605
Gly Thr Ile Gln Gly Gly Leu Asp Thr Thr Lys Ser Val Val Met Gly
    610                 615                 620

Thr Lys Asp Thr Val Thr Thr Gly Leu Thr Gly Ala Val Asn Val Ala
625                 630                 635                 640

Lys Gly Ala Val Gln Gly Gly Leu Asp Thr Thr Lys Ser Val Val Met
                645                 650                 655

Gly Thr Lys Asp Thr Val Thr Thr Gly Leu Thr Gly Ala Leu Asn Val
            660                 665                 670

Ala Lys Gly Thr Ala Gln Met Gly Ile Asp Thr Ser Lys Thr Val Leu
        675                 680                 685

Ile Gly Thr Lys Asp Thr Val Cys Ala Gly Ala Thr Gly Ala Ile Asn
    690                 695                 700

Met Ala Lys Gly Ala Ala Gln Gly Gly Leu Asp Thr Thr Lys Ser Val
705                 710                 715                 720

Leu Met Gly Thr Lys Asp Thr Val Thr Thr Gly Leu Thr Gly Ala Ile
                725                 730                 735

Asn Val Ala Lys Gly Ser Ala Gln Gly Gly Leu Asp Thr Thr Lys Ser
            740                 745                 750

Val Leu Ile Gly Thr Lys Asp Thr Val Thr Thr Gly Leu Thr Gly Ala
        755                 760                 765

Leu Asn Val Ala Lys Gly Thr Val Gln Thr Gly Leu Asp Thr Ser Gln
    770                 775                 780

Arg Val Leu Thr Gly Thr Lys Asp Asn Val Tyr Ala Gly Val Thr Gly
785                 790                 795                 800

Ala Val Asn Val Ala Lys Gly Thr Ile Gln Gly Gly Leu Asp Thr Thr
                805                 810                 815

Lys Ser Val Val Met Gly Thr Lys Asp Thr Val Thr Thr Gly Leu Thr
            820                 825                 830

Gly Ala Val Asn Val Ala Lys Gly Ala Val Gln Gly Gly Leu Asp Thr
        835                 840                 845

Thr Lys Ser Val Val Met Gly Thr Lys Asp Thr Val Thr Thr Gly Leu
    850                 855                 860

Thr Gly Ala Met Asn Val Ala Lys Gly Thr Ala Gln Met Gly Ile Asp
865                 870                 875                 880

Thr Ser Lys Thr Val Leu Thr Gly Thr Lys Asp Thr Val Cys Ala Gly
                885                 890                 895

Leu Thr Gly Ala Ile Asn Val Ala Lys Gly Ala Thr Gln Gly Gly Leu
            900                 905                 910

Asp Thr Thr Lys Ser Val Leu Met Gly Thr Lys Asp Thr Val Thr Thr
        915                 920                 925

Gly Leu Thr Gly Ala Ile Asn Val Ala Lys Gly Ala Gln Gly Gly
    930                 935                 940

Leu Asp Thr Thr Lys Ser Val Leu Leu Gly Thr Lys Asp Thr Val
945                 950                 955                 960

Thr Gly Leu Thr Gly Ala Ala Asn Val Ala Lys Glu Thr Val Gln Met
                965                 970                 975

Gly Leu Asp Thr Ser Lys Asn Ile Leu Met Asp Thr Lys Asp Ser Ile
            980                 985                 990

Cys Ala Gly Ala Thr Gly Ala Ile Thr Val Val Lys Gly Ala Ala Gln
        995                 1000                1005

Gly Gly Leu Asp Thr Ser Asn Ala Ala Leu Thr Gly Thr Met Asp
    1010                1015                1020
```

```
Thr Ala Lys Gly Thr Val Gln Thr Ser Leu Asp Thr Ser Lys His
1025                1030                1035

Met Leu Ile Gly Met Lys Asp Thr Val Cys Ala Gly Val Thr Ser
1040                1045                1050

Ala Met Asn Met Ala Lys Gly Ile His Lys Asn Thr Asp Thr Thr
1055                1060                1065

Arg Asp Thr Gln Ser Ser Val Leu Ala His Ser Gly Asn Val Ala
1070                1075                1080

Thr Asn Ala Ile His Thr Gly Val His Thr Val Pro Ser Ser Leu
1085                1090                1095

Ser Gly Ser His Ser Ile Ile Cys His Glu Pro Ser Ile Tyr Arg
1100                1105                1110

Ala Thr Asn His Gly Val Gly Gln Ala Ile Leu Thr Ser Thr Glu
1115                1120                1125

Ser Leu Cys Cys Glu Thr Ser Ser Phe Ser Asp Lys Tyr Gly Leu
1130                1135                1140

Gly His Val Thr Glu Pro Arg Ala Asp Thr Lys Thr Leu Val Ser
1145                1150                1155

Gly Met Ala Ser Ser Ala Cys Ala Ala Thr Arg Ser Val Glu Glu
1160                1165                1170

Cys Gly Gln Leu Ala Ala Thr Gly Phe Ala Ala Leu Pro Asp Glu
1175                1180                1185

Leu Lys Gly Leu Gly Asp Ile Phe Gln Pro Met Thr Thr Glu Glu
1190                1195                1200

Gln Ala Gln Leu Ala Val Ser Glu Ser Gly Pro Arg Val Leu Ser
1205                1210                1215

Ala Asp Arg Gly Ser Tyr Tyr Ile Arg Leu Gly Asp Leu Ala Pro
1220                1225                1230

Ser Phe Arg Gln Arg Ala Phe Glu His Ala Leu Ser His Ile Gln
1235                1240                1245

His Asn Gln Phe Gln Ala Arg Ala Ala Leu Ala Gln Leu Gln Glu
1250                1255                1260

Ala Phe Gln Met Thr Asp Met Thr Met Glu Ala Ala Cys Gly Lys
1265                1270                1275

Leu Cys Ser Asp Gln Ser Leu Asn Thr Met Val Glu Ala Val Gly
1280                1285                1290

Ser His Glu Met Arg Ala Ser Val Ala Gln Asp Arg Leu Cys Thr
1295                1300                1305

Leu Ala His Gln Leu His Ala Ala Tyr Ser Ser Leu Val Thr Ser
1310                1315                1320

Leu Gln Gly Leu Pro Glu Val Gln Gln Gln Ala Gly Gln Ala Arg
1325                1330                1335

His Ser Leu Cys Lys Leu Tyr Gly Leu Val Ser Ser Glu Ala Gly
1340                1345                1350

Ser Glu Leu Gln Thr Glu Gln Leu Ala Gln Ser Ser Ala Gly Val
1355                1360                1365

Val Glu Ala Trp Gln Gly Leu Glu Val Leu Leu Glu Lys Leu Gln
1370                1375                1380

Gln Asn Pro Pro Leu Ser Trp Leu Val Gly Pro Phe Thr Ser Met
1385                1390                1395

Pro Cys Gly Gln Leu
1400
```

```
<210> SEQ ID NO 17
<211> LENGTH: 115
<212> TYPE: PRT
<213> ORGANISM: Mus musculus

<400> SEQUENCE: 17

Met Asp Pro Gln Thr Gln Asn Thr Ser Leu Gln Arg Leu Gln Asn Val
1               5                   10                  15

Glu Asn Arg Val Val Lys Val Leu Glu Leu Ala Gly Gly Val Met Glu
            20                  25                  30

Glu Leu Ala Ser Pro Ser Gly Pro Lys Lys Glu Phe Val Asn Ser His
        35                  40                  45

Cys Arg Glu Phe Met Gln Ser Met Lys Asp Ile Gln Val Thr Leu Arg
50                  55                  60

Glu Glu Ile Lys Ser Ala Cys Glu Tyr Arg Pro Phe Glu Lys Cys Asp
65                  70                  75                  80

Tyr Asn Ala Arg Ile Ala Asn Glu Ile Cys Phe Gln Lys Leu Glu Tyr
                85                  90                  95

Val Leu Thr Gln Leu Glu Asp Leu Lys Gln Thr Ala Asp Arg Tyr Pro
            100                 105                 110

Ser Ser Asp
        115

<210> SEQ ID NO 18
<211> LENGTH: 483
<212> TYPE: PRT
<213> ORGANISM: Mus musculus

<400> SEQUENCE: 18

Met Val Asn Ser Asn Asn Asp Arg Gly Val Val Gln Gly Gln Trp Gln
1               5                   10                  15

Gly Lys Tyr Gly Gly Thr Asn Pro Leu Asn Trp Arg Gly Ser Val
            20                  25                  30

Ala Ile Leu Gln Lys Trp Phe Lys Gly Arg Tyr Lys Pro Val Lys Tyr
        35                  40                  45

Gly Gln Cys Trp Val Phe Ala Gly Val Met Cys Thr Val Leu Arg Cys
50                  55                  60

Leu Gly Ile Ala Thr Arg Val Val Ser Asn Phe Asn Ser Ala His Asp
65                  70                  75                  80

Thr Asp Gly Asn Leu Ser Val Asp Lys Tyr Val Asp Ser Tyr Gly Arg
                85                  90                  95

Thr Leu Glu Asp Leu Thr Glu Asp Ser Met Trp Asn Phe His Val Trp
            100                 105                 110

Asn Glu Ser Trp Phe Ala Arg Gln Asp Leu Gly Pro Ser Tyr Asp Gly
        115                 120                 125

Trp Gln Val Leu Asp Ala Thr Pro Gln Glu Glu Ser Glu Gly Met Phe
130                 135                 140

Arg Cys Gly Pro Ala Ser Val Thr Ala Ile Arg Glu Gly Asp Val His
145                 150                 155                 160

Leu Ala His Asp Gly Pro Phe Val Phe Ala Glu Val Asn Ala Asp Tyr
                165                 170                 175

Ile Thr Trp Leu Trp His Glu Asp Lys Arg Arg Glu Arg Val Tyr Ser
            180                 185                 190

Asp Thr Lys Lys Ile Gly Arg Cys Ile Ser Thr Lys Ala Val Gly Ser
        195                 200                 205
```

```
Asp Ser Arg Val Asp Ile Thr Gly Leu Tyr Lys Tyr Pro Glu Gly Ser
    210                 215                 220

Arg Lys Glu Arg Gln Val Tyr Ser Lys Ala Val Lys Lys Leu Leu Ser
225                 230                 235                 240

Val Glu Ala Trp Gly Arg Arg Arg Ile Arg Arg Ala Ser Val Arg
                245                 250                 255

Gly Val Trp Arg Asp Asp Leu Leu Glu Pro Val Thr Lys Pro Ser Ile
                260                 265                 270

Thr Gly Lys Phe Lys Val Leu Glu Pro Pro Val Leu Gly Gln Asp Leu
                275                 280                 285

Lys Leu Ala Leu Cys Leu Thr Asn Leu Thr Ala Arg Ala Gln Arg Val
    290                 295                 300

Arg Val Asn Val Ser Gly Ala Thr Ile Leu Tyr Thr Arg Lys Pro Val
305                 310                 315                 320

Ala Glu Ile Leu Arg Glu Ser His Thr Val Lys Leu Gly Pro Leu Glu
                325                 330                 335

Glu Lys Lys Ile Pro Val Thr Ile Ser Tyr Ser Gln Tyr Lys Gly Asp
                340                 345                 350

Leu Thr Glu Asp Lys Lys Ile Leu Leu Ala Ala Met Cys Leu Val Ser
                355                 360                 365

Lys Gly Glu Lys Leu Leu Val Glu Lys Asp Ile Thr Leu Glu Asp Phe
370                 375                 380

Ile Thr Ile Lys Val Leu Gly Pro Ala Val Gly Val Thr Val Thr
385                 390                 395                 400

Val Glu Val Leu Val Ile Asn Pro Leu Ser Glu Ser Val Lys Asp Cys
                405                 410                 415

Val Leu Met Val Glu Gly Ser Gly Leu Leu Gln Gly Gln Leu Ser Ile
                420                 425                 430

Glu Val Pro Ser Leu Gln Pro Gln Glu Lys Ala Leu Ile Gln Phe Asn
            435                 440                 445

Ile Thr Pro Ser Lys Ser Gly Pro Arg Gln Leu Gln Val Asp Leu Val
            450                 455                 460

Ser Ser Gln Phe Pro Asp Ile Lys Gly Phe Val Ile Ile His Val Ala
465                 470                 475                 480

Thr Ala Lys

<210> SEQ ID NO 19
<211> LENGTH: 228
<212> TYPE: PRT
<213> ORGANISM: Mus musculus

<400> SEQUENCE: 19

Met Lys Ser Lys Lys Pro Leu Lys Ile Thr Met Glu Asp Ser Arg Arg
1               5                   10                  15

Leu Asn Asp Pro Ala Glu Gln Gly Gly Leu Cys Pro Ala Pro Val Gly
                20                  25                  30

Pro Ser Tyr Ser Glu Ala Trp Gly Tyr Phe His Leu Asp Pro Ala Gln
                35                  40                  45

Pro Arg His Arg Met Met Ser Ala Trp Ala Thr Cys Arg Leu Cys Gly
            50                  55                  60

Leu Gln Val Gly Gly Leu Pro Asn Phe Gln Met Trp Thr Arg Ala Leu
65              70                  75                  80

Cys Gln His Leu Ser Asp Val His Leu Pro Glu Leu Lys Lys Ser Ala
                85                  90                  95
```

-continued

```
Ala Pro Ser Ser Pro Thr Thr Met Pro Cys Pro Pro Pro Ser Pro
                100                 105                 110

Thr Met Ala Ala Glu Gly Asp Trp Ala Arg Leu Leu Glu Gln Met Gly
        115                 120                 125

Glu Leu Ala Met Arg Gly Ser Gln Arg Glu Leu Glu Leu Glu Arg Arg
    130                 135                 140

Glu Ala Ala Leu Met Gln Ala Glu Leu Glu Leu Glu Arg Lys Arg Gln
145                 150                 155                 160

Ala Leu Lys Gln Glu Ala Gln Ser Val Glu Gln Glu Arg His Gln Leu
                165                 170                 175

Gln Val Glu Arg Glu Ala Leu Ser Lys Trp Ile Lys Lys Gln Ser Pro
            180                 185                 190

Gly Ala Gln Val Pro Glu Pro Pro Ser Pro Leu Pro Leu Leu Pro Lys
        195                 200                 205

Glu Asp Pro Asp Ile His Asp Asn Asn Ser Asp Asn Asp Met Val Thr
    210                 215                 220

Lys Val Leu Leu
225

<210> SEQ ID NO 20
<211> LENGTH: 872
<212> TYPE: PRT
<213> ORGANISM: Mus musculus

<400> SEQUENCE: 20

Met Glu Ser Leu Leu Arg Phe Leu Ala Leu Leu Leu Arg Gly Ala
1               5                   10                  15

Val Ala Glu Gly Pro Ala Lys Lys Val Leu Thr Leu Glu Gly Asp Leu
                20                  25                  30

Val Leu Gly Gly Leu Phe Pro Val His Gln Lys Gly Gly Pro Ala Glu
            35                  40                  45

Glu Cys Gly Pro Val Asn Glu His Arg Gly Ile Gln Arg Leu Glu Ala
        50                  55                  60

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
                100                 105                 110

Gly Ala Asp Gly Ser Arg His Ile Cys Pro Asp Gly Ser Tyr Ala Thr
            115                 120                 125

Leu Ser Asp Ala Pro Thr Ala Ile Thr Gly Val Ile Gly Gly Ser Tyr
    130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
        195                 200                 205

Thr Val Ala Ser Glu Gly Asp Tyr Gly Glu Thr Gly Ile Glu Ala Phe
    210                 215                 220

Glu Leu Glu Ala Arg Ala Arg Asn Ile Cys Val Ala Thr Ser Glu Lys
225                 230                 235                 240
```

```
Val Gly Arg Ala Met Ser Arg Ala Ala Phe Glu Val Val Arg Ala
            245                 250                 255

Leu Leu Gln Lys Pro Ser Ala Arg Val Ala Val Leu Phe Thr Arg Ser
            260                 265                 270

Glu Asp Ala Arg Glu Leu Leu Ala Ala Thr Gln Arg Leu Asn Ala Ser
            275                 280                 285

Phe Thr Trp Val Ala Ser Asp Gly Trp Gly Ala Leu Glu Ser Val Val
        290                 295                 300

Ala Gly Ser Glu Arg Ala Ala Glu Gly Ala Ile Thr Ile Glu Leu Ala
305                 310                 315                 320

Ser Tyr Pro Ile Ser Asp Phe Ala Ser Tyr Phe Gln Asn Leu Asp Pro
                325                 330                 335

Trp Asn Asn Ser Arg Asn Pro Trp Phe Arg Glu Phe Trp Glu Glu Arg
                340                 345                 350

Phe Arg Cys Ser Phe Arg Gln Arg Asp Cys Ala Ala His Ser Leu Arg
                355                 360                 365

Ala Val Pro Phe Glu Gln Glu Ser Lys Ile Met Phe Val Val Asn Ala
            370                 375                 380

Val Tyr Ala Met Ala His Ala Leu His Asn Met His Arg Ala Leu Cys
385                 390                 395                 400

Pro Asn Thr Thr Arg Leu Cys Asp Ala Met Arg Pro Val Asn Gly Arg
                405                 410                 415

Arg Leu Tyr Lys Asp Phe Val Leu Asn Val Lys Phe Asp Ala Pro Phe
            420                 425                 430

Arg Pro Ala Asp Thr Asp Asp Glu Val Arg Phe Asp Arg Phe Gly Asp
            435                 440                 445

Gly Ile Gly Arg Tyr Asn Ile Phe Thr Tyr Leu Arg Ala Gly Asn Gly
        450                 455                 460

Arg Tyr Arg Tyr Gln Lys Val Gly Tyr Trp Ala Glu Gly Leu Thr Leu
465                 470                 475                 480

Asp Thr Ser Ile Ile Pro Trp Ala Ser Pro Ser Ala Gly Thr Leu Pro
                485                 490                 495

Ala Ser Arg Cys Ser Glu Pro Cys Leu Gln Asn Glu Val Lys Ser Val
            500                 505                 510

Gln Pro Gly Glu Val Cys Cys Trp Leu Cys Ile Pro Cys Gln Pro Tyr
            515                 520                 525

Glu Tyr Arg Leu Asp Glu Phe Thr Cys Ala Asp Cys Gly Leu Gly Tyr
            530                 535                 540

Trp Pro Asn Ala Ser Leu Thr Gly Cys Phe Glu Leu Pro Gln Glu Tyr
545                 550                 555                 560

Ile Arg Trp Gly Asp Ala Trp Ala Val Gly Pro Val Thr Ile Ala Cys
                565                 570                 575

Leu Gly Ala Leu Ala Thr Leu Phe Val Leu Gly Val Phe Val Arg His
            580                 585                 590

Asn Ala Thr Pro Val Val Lys Ala Ser Gly Arg Glu Leu Cys Tyr Ile
            595                 600                 605

Leu Leu Gly Gly Val Phe Leu Cys Tyr Cys Met Thr Phe Ile Phe Ile
        610                 615                 620

Ala Lys Pro Ser Thr Ala Val Cys Thr Leu Arg Arg Leu Gly Leu Gly
625                 630                 635                 640

Thr Ala Phe Ser Val Cys Tyr Ser Ala Leu Leu Thr Lys Thr Asn Arg
                645                 650                 655
```

```
Ile Ala Arg Ile Phe Gly Gly Ala Arg Glu Gly Ala Gln Arg Pro Arg
            660                 665                 670

Phe Ile Ser Pro Ala Ser Gln Val Ala Ile Cys Leu Ala Leu Ile Ser
        675                 680                 685

Gly Gln Leu Leu Ile Val Ala Ala Trp Leu Val Val Glu Ala Pro Gly
    690                 695                 700

Ile Gly Lys Glu Thr Ala Pro Glu Arg Arg Glu Val Val Thr Leu Arg
705                 710                 715                 720

Cys Asn His Arg Asp Ala Ser Met Leu Gly Ser Leu Ala Tyr Asn Val
                725                 730                 735

Leu Leu Ile Ala Leu Cys Thr Leu Tyr Ala Phe Lys Thr Arg Lys Cys
            740                 745                 750

Pro Glu Asn Phe Asn Glu Ala Lys Phe Ile Gly Phe Thr Met Tyr Thr
        755                 760                 765

Thr Cys Ile Ile Trp Leu Ala Phe Leu Pro Ile Phe Tyr Val Thr Ser
    770                 775                 780

Ser Asp Tyr Arg Val Gln Thr Thr Thr Met Cys Val Ser Val Ser Leu
785                 790                 795                 800

Ser Gly Ser Val Val Leu Gly Cys Leu Phe Ala Pro Lys Leu His Ile
                805                 810                 815

Ile Leu Phe Gln Pro Gln Lys Asn Val Val Ser His Arg Ala Pro Thr
            820                 825                 830

Ser Arg Phe Gly Ser Ala Ala Pro Arg Ala Ser Ala Asn Leu Gly Gln
        835                 840                 845

Gly Ser Gly Ser Gln Leu Val Pro Thr Val Cys Asn Gly Arg Glu Val
    850                 855                 860

Val Asp Ser Thr Thr Ser Ser Leu
865                 870

<210> SEQ ID NO 21
<211> LENGTH: 558
<212> TYPE: PRT
<213> ORGANISM: Mus musculus

<400> SEQUENCE: 21

Asn Ala Val Thr Tyr Glu Asp Val His Val Asn Phe Thr Gln Glu Glu
1               5                   10                  15

Trp Ala Leu Leu Asp Pro Ser Gln Lys Thr Leu Tyr Lys Asp Val Met
            20                  25                  30

Leu Glu Thr Phe Arg Asn Leu Asn Ala Ile Gly Phe Asn Trp Glu Ala
        35                  40                  45

Gln Asn Ile Glu Glu Tyr Cys Gln Ser Ser Arg Arg His Arg Arg Cys
    50                  55                  60

Glu Arg Ser Gln Ser Ala Glu Lys Pro Ser Glu Tyr Thr Gln Arg Asp
65                  70                  75                  80

Lys Ala Phe Ala Leu His Asp His Ser His Ala Gln Arg His Glu Arg
                85                  90                  95

Val His Thr Glu Lys Ile Pro Ser Glu Val Ile His Cys Val Glu Asp
            100                 105                 110

Phe Leu Pro Tyr Thr Ser Leu Gln Val His Lys Arg Thr Gln Thr Gly
        115                 120                 125

Gln Lys Pro Tyr Glu Cys Asn Gln Cys Gly Lys Gly Phe Val Met Pro
    130                 135                 140

Ser Cys Leu Lys Arg His Glu Arg Phe His Thr Gly Glu Lys Pro Tyr
145                 150                 155                 160
```

Lys Cys Asn Gln Cys Asp Lys Ala Phe Ser Gln Tyr Asn Asn Leu Gln
                165                 170                 175

Thr His Arg Arg Thr His Thr Gly Glu Lys Pro Tyr Lys Cys Asn Gln
            180                 185                 190

Cys Asp Lys Ala Phe Ser Gln His Ser Thr Leu Gln Thr His Arg Arg
        195                 200                 205

Thr His Thr Gly Glu Lys Pro Phe Lys Cys Asn Gln Cys Asp Lys Ala
    210                 215                 220

Phe Ser Glu Lys Cys Ser Leu Gln Thr His Arg Arg Thr His Thr Gly
225                 230                 235                 240

Glu Lys Pro Tyr Lys Cys Asn Gln Cys Asp Lys Ala Phe Ser Gln Tyr
                245                 250                 255

Ser His Leu His Ile His Arg Arg Thr His Thr Gly Glu Lys Pro Leu
            260                 265                 270

Lys Cys Asn Glu Cys Asp Glu Thr Phe Ser Asn His Ser Asn Leu Gln
        275                 280                 285

Thr His Arg Arg Ile His Thr Gly Glu Lys Pro Tyr Lys Cys Asn Gln
    290                 295                 300

Cys Asp Lys Ala Phe Ser Gln His Ser Thr Leu Gln Asn His Arg Arg
305                 310                 315                 320

Thr His Thr Gly Glu Lys Pro Phe Lys Cys Asn Gln Cys Asp Lys Ala
                325                 330                 335

Phe Ser Arg His Ser Thr Leu Gln Thr His Arg Arg Thr His Thr Gly
            340                 345                 350

Glu Lys Pro Phe Lys Cys Asn Gln Cys Asp Lys Ala Phe Ser Gln Tyr
        355                 360                 365

Ser His Leu His Ile His Arg Arg Thr His Thr Gly Glu Lys Pro Phe
    370                 375                 380

Lys Cys Asn Gln Cys Asn Lys Ala Phe Ser Gln Tyr Ser His Leu His
385                 390                 395                 400

Ile His Arg Arg Thr His Thr Gly Glu Lys Pro Tyr Lys Cys Asn Gln
                405                 410                 415

Cys Asp Lys Thr Phe Ser Asn His Ser Thr Leu Gln Thr His Arg Arg
            420                 425                 430

Thr His Thr Gly Glu Lys Pro Tyr Lys Cys Asn Gln Cys Asp Lys Ala
        435                 440                 445

Phe Ser Arg His Ser Thr Leu Gln Thr His Arg Arg Thr His Thr Gly
    450                 455                 460

Glu Lys Pro Phe Lys Cys Asn Gln Cys Asp Lys Ala Phe Ser Gln Lys
465                 470                 475                 480

Cys Ser Leu Gln Lys His Ile Arg Ile His Thr Gly Glu Lys Leu Tyr
                485                 490                 495

Lys Cys Asn Glu Cys Asp Lys Ala Phe Ser Gln His Ser Thr Leu Gln
            500                 505                 510

Thr His Arg Arg Thr His Thr Gly Glu Lys Pro Phe Lys Phe Asn Glu
        515                 520                 525

Cys Asp Glu Gly Phe Ser His His Tyr Asn Leu Gln Ile His Glu Arg
    530                 535                 540

Arg His Thr Arg Glu Lys Pro Tyr Lys Cys Ile Gln Cys Val
545                 550                 555

<210> SEQ ID NO 22
<211> LENGTH: 311

```
<212> TYPE: PRT
<213> ORGANISM: Mus musculus

<400> SEQUENCE: 22

Met Gly Leu Glu Asn Gly Ser Leu Val Thr Glu Phe Ile Leu Leu Gly
1               5                   10                  15

Leu Thr Asn Asp Pro Asp Leu Gln Leu Pro Leu Phe Leu Leu Phe Leu
                20                  25                  30

Leu Ile Tyr Thr Thr Thr Ala Val Gly Asn Leu Ala Leu Ile Thr Leu
            35                  40                  45

Ile Ala Leu Asn Ser His Leu His Thr Pro Met Tyr Phe Phe Leu Leu
50                  55                  60

Asn Leu Ser Cys Ile Asp Leu Cys Tyr Ser Ser Val Ile Thr Pro Lys
65                  70                  75                  80

Met Leu Met Asn Phe Leu Val Arg Lys Asn Ile Ile Ser Tyr Met Gly
                85                  90                  95

Cys Met Thr Gln Leu Tyr Phe Phe Cys Phe Phe Ala Ile Cys Glu Cys
            100                 105                 110

Cys Val Leu Thr Ser Met Ala Tyr Asp Arg Tyr Val Ala Ile Cys Asn
        115                 120                 125

Pro Leu Leu Tyr Asn Ile Thr Met Ser Pro Lys Val Cys Ser Tyr Leu
130                 135                 140

Met Leu Gly Ser Tyr Ile Met Gly Phe Ser Gly Ala Met Ile His Thr
145                 150                 155                 160

Gly Cys Ile Leu Arg Leu Thr Phe Cys Asp Arg Asn Ile Ile Asn His
                165                 170                 175

Tyr Phe Cys Asp Leu Phe Pro Leu Leu Gln Leu Ser Cys Thr Ser Thr
            180                 185                 190

Tyr Ala Asn Glu Ile Glu Ile Leu Ile Val Gly Gly Lys Asp Ile Ile
        195                 200                 205

Val Pro Ser Val Ile Ile Phe Thr Ser Tyr Gly Phe Ile Leu Ser Asn
210                 215                 220

Ile Leu Gln Met Arg Ser Thr Ala Gly Met Ser Lys Ala Phe Ser Thr
225                 230                 235                 240

Cys Ser Ser His Ile Leu Ala Val Ser Leu Phe Phe Gly Ser Cys Ala
                245                 250                 255

Phe Met Tyr Leu Gln Pro Ser Ser Pro Gly Ser Met Asp Gln Gly Lys
            260                 265                 270

Val Ser Ser Val Phe Tyr Thr Ile Val Val Pro Met Met Asn Pro Leu
        275                 280                 285

Ile Tyr Ser Phe Arg Asn Lys Asp Val Lys Ile Ala Leu Arg Lys Ile
290                 295                 300

Phe Gly Lys Arg Arg Phe Ser
305                 310

<210> SEQ ID NO 23
<211> LENGTH: 20
<212> TYPE: DNA
<213> ORGANISM: Artificial sequence
<220> FEATURE:
<223> OTHER INFORMATION: gRNA sequence

<400> SEQUENCE: 23
cacgcccgag ctgtccagtt                                               20

<210> SEQ ID NO 24
```

```
<211> LENGTH: 20
<212> TYPE: DNA
<213> ORGANISM: Artificial sequence
<220> FEATURE:
<223> OTHER INFORMATION: gRNA sequence

<400> SEQUENCE: 24
tacgcactca tactgatgtt                                                    20

<210> SEQ ID NO 25
<211> LENGTH: 20
<212> TYPE: DNA
<213> ORGANISM: Artificial sequence
<220> FEATURE:
<223> OTHER INFORMATION: gRNA sequence

<400> SEQUENCE: 25
ctactcctct cgctatgctc                                                    20

<210> SEQ ID NO 26
<211> LENGTH: 20
<212> TYPE: DNA
<213> ORGANISM: Artificial sequence
<220> FEATURE:
<223> OTHER INFORMATION: gRNA sequence

<400> SEQUENCE: 26
tgcaaccgcg aaccttacc                                                     20

<210> SEQ ID NO 27
<211> LENGTH: 20
<212> TYPE: DNA
<213> ORGANISM: Artificial sequence
<220> FEATURE:
<223> OTHER INFORMATION: gRNA sequence

<400> SEQUENCE: 27
gcttgacact gcatcgatat                                                    20

<210> SEQ ID NO 28
<211> LENGTH: 20
<212> TYPE: DNA
<213> ORGANISM: Artificial sequence
<220> FEATURE:
<223> OTHER INFORMATION: gRNA sequence

<400> SEQUENCE: 28
actttcgtat acagatactg                                                    20

<210> SEQ ID NO 29
<211> LENGTH: 20
<212> TYPE: DNA
<213> ORGANISM: Artificial sequence
<220> FEATURE:
<223> OTHER INFORMATION: gRNA sequence

<400> SEQUENCE: 29
ctgcctcctt agttccgaca                                                    20

<210> SEQ ID NO 30
<211> LENGTH: 20
<212> TYPE: DNA
<213> ORGANISM: Artificial sequence
<220> FEATURE:
<223> OTHER INFORMATION: gRNA sequence

<400> SEQUENCE: 30
```

```
tttcacgctc gatatcctcc                                              20

<210> SEQ ID NO 31
<211> LENGTH: 20
<212> TYPE: DNA
<213> ORGANISM: Artificial sequence
<220> FEATURE:
<223> OTHER INFORMATION: gRNA sequence

<400> SEQUENCE: 31
catcggtggc tgggtcctcc                                              20

<210> SEQ ID NO 32
<211> LENGTH: 20
<212> TYPE: DNA
<213> ORGANISM: Artificial sequence
<220> FEATURE:
<223> OTHER INFORMATION: gRNA sequence

<400> SEQUENCE: 32
gcgcgaggcg gccctaatgc                                              20

<210> SEQ ID NO 33
<211> LENGTH: 20
<212> TYPE: DNA
<213> ORGANISM: Artificial sequence
<220> FEATURE:
<223> OTHER INFORMATION: gRNA sequence

<400> SEQUENCE: 33
gctgtatgac ctcggacatc                                              20

<210> SEQ ID NO 34
<211> LENGTH: 20
<212> TYPE: DNA
<213> ORGANISM: Artificial sequence
<220> FEATURE:
<223> OTHER INFORMATION: gRNA sequence

<400> SEQUENCE: 34
cttcaaatga gatccactgc                                              20

<210> SEQ ID NO 35
<211> LENGTH: 20
<212> TYPE: DNA
<213> ORGANISM: Artificial sequence
<220> FEATURE:
<223> OTHER INFORMATION: gRNA sequence

<400> SEQUENCE: 35
gcggcataac gccacacccg                                              20

<210> SEQ ID NO 36
<211> LENGTH: 20
<212> TYPE: DNA
<213> ORGANISM: Artificial sequence
<220> FEATURE:
<223> OTHER INFORMATION: 5' PCR primer

<400> SEQUENCE: 36
tcacagtggt ctgcctcttc                                              20

<210> SEQ ID NO 37
<211> LENGTH: 22
<212> TYPE: DNA
```

```
<213> ORGANISM: Artificial sequence
<220> FEATURE:
<223> OTHER INFORMATION: 5' PCR primer

<400> SEQUENCE: 37
tgggacttgt ttaaaggagc tt                                          22

<210> SEQ ID NO 38
<211> LENGTH: 20
<212> TYPE: DNA
<213> ORGANISM: Artificial sequence
<220> FEATURE:
<223> OTHER INFORMATION: 5' PCR primer

<400> SEQUENCE: 38
gcagagacct gaaggacagc                                             20

<210> SEQ ID NO 39
<211> LENGTH: 20
<212> TYPE: DNA
<213> ORGANISM: Artificial sequence
<220> FEATURE:
<223> OTHER INFORMATION: 5' PCR primer

<400> SEQUENCE: 39
ggcttactag ggcgtctggt                                             20

<210> SEQ ID NO 40
<211> LENGTH: 20
<212> TYPE: DNA
<213> ORGANISM: Artificial sequence
<220> FEATURE:
<223> OTHER INFORMATION: 5' PCR primer

<400> SEQUENCE: 40
gtaactggat tggcccaaga                                             20

<210> SEQ ID NO 41
<211> LENGTH: 20
<212> TYPE: DNA
<213> ORGANISM: Artificial sequence
<220> FEATURE:
<223> OTHER INFORMATION: 5' PCR primer

<400> SEQUENCE: 41
gtttgcagct cccatgactc                                             20

<210> SEQ ID NO 42
<211> LENGTH: 18
<212> TYPE: DNA
<213> ORGANISM: Artificial sequence
<220> FEATURE:
<223> OTHER INFORMATION: 5' PCR primer

<400> SEQUENCE: 42
actcagcccc gccctaag                                               18

<210> SEQ ID NO 43
<211> LENGTH: 19
<212> TYPE: DNA
<213> ORGANISM: Artificial sequence
<220> FEATURE:
<223> OTHER INFORMATION: 5' PCR primer

<400> SEQUENCE: 43
actggtttgg gggatccctt                                             19
```

<210> SEQ ID NO 44
<211> LENGTH: 18
<212> TYPE: DNA
<213> ORGANISM: Artificial sequence
<220> FEATURE:
<223> OTHER INFORMATION: 5' PCR primer

<400> SEQUENCE: 44
gagctcgccg accaccat                                                 18

<210> SEQ ID NO 45
<211> LENGTH: 20
<212> TYPE: DNA
<213> ORGANISM: Artificial sequence
<220> FEATURE:
<223> OTHER INFORMATION: 5' PCR primer

<400> SEQUENCE: 45
ttttccctct gttgcagctc                                               20

<210> SEQ ID NO 46
<211> LENGTH: 20
<212> TYPE: DNA
<213> ORGANISM: Artificial sequence
<220> FEATURE:
<223> OTHER INFORMATION: 5' PCR primer

<400> SEQUENCE: 46
tgactggatg ctttgagctg                                               20

<210> SEQ ID NO 47
<211> LENGTH: 20
<212> TYPE: DNA
<213> ORGANISM: Artificial sequence
<220> FEATURE:
<223> OTHER INFORMATION: 5' PCR primer

<400> SEQUENCE: 47
ccacgtcacc tcagctgtct                                               20

<210> SEQ ID NO 48
<211> LENGTH: 20
<212> TYPE: DNA
<213> ORGANISM: Artificial sequence
<220> FEATURE:
<223> OTHER INFORMATION: 5' PCR primer

<400> SEQUENCE: 48
caggtctgcc aagttccta                                                20

<210> SEQ ID NO 49
<211> LENGTH: 20
<212> TYPE: DNA
<213> ORGANISM: Artificial sequence
<220> FEATURE:
<223> OTHER INFORMATION: 3' PCR primer

<400> SEQUENCE: 49
tgaaaccttt ccctctccaa                                               20

<210> SEQ ID NO 50
<211> LENGTH: 22
<212> TYPE: DNA
<213> ORGANISM: Artificial sequence
<220> FEATURE:

```
<223> OTHER INFORMATION: 3' PCR primer

<400> SEQUENCE: 50
ttgcgcttct tattatcaat gg                                              22

<210> SEQ ID NO 51
<211> LENGTH: 20
<212> TYPE: DNA
<213> ORGANISM: Artificial sequence
<220> FEATURE:
<223> OTHER INFORMATION: 3' PCR primer

<400> SEQUENCE: 51
caaagggatc tcggaaggtt                                                 20

<210> SEQ ID NO 52
<211> LENGTH: 19
<212> TYPE: DNA
<213> ORGANISM: Artificial sequence
<220> FEATURE:
<223> OTHER INFORMATION: 3' PCR primer

<400> SEQUENCE: 52
actaggggct ctccccact                                                  19

<210> SEQ ID NO 53
<211> LENGTH: 21
<212> TYPE: DNA
<213> ORGANISM: Artificial sequence
<220> FEATURE:
<223> OTHER INFORMATION: 3' PCR primer

<400> SEQUENCE: 53
tgtggtaaag cttgtgtgtg g                                               21

<210> SEQ ID NO 54
<211> LENGTH: 21
<212> TYPE: DNA
<213> ORGANISM: Artificial sequence
<220> FEATURE:
<223> OTHER INFORMATION: 3' PCR primer

<400> SEQUENCE: 54
cagtgtgacc agcagtgaag a                                               21

<210> SEQ ID NO 55
<211> LENGTH: 20
<212> TYPE: DNA
<213> ORGANISM: Artificial sequence
<220> FEATURE:
<223> OTHER INFORMATION: 3' PCR primer

<400> SEQUENCE: 55
cgcacattaa caggcatttc                                                 20

<210> SEQ ID NO 56
<211> LENGTH: 20
<212> TYPE: DNA
<213> ORGANISM: Artificial sequence
<220> FEATURE:
<223> OTHER INFORMATION: 3' PCR primer

<400> SEQUENCE: 56
aacagatcaa gtggggttgg                                                 20
```

```
<210> SEQ ID NO 57
<211> LENGTH: 20
<212> TYPE: DNA
<213> ORGANISM: Artificial sequence
<220> FEATURE:
<223> OTHER INFORMATION: 3' PCR primer

<400> SEQUENCE: 57
tcagtgcttc acgctctacc                                                20

<210> SEQ ID NO 58
<211> LENGTH: 20
<212> TYPE: DNA
<213> ORGANISM: Artificial sequence
<220> FEATURE:
<223> OTHER INFORMATION: 3' PCR primer

<400> SEQUENCE: 58
aggtgaggag ggctgaagat                                                20

<210> SEQ ID NO 59
<211> LENGTH: 18
<212> TYPE: DNA
<213> ORGANISM: Artificial sequence
<220> FEATURE:
<223> OTHER INFORMATION: 3' PCR primer

<400> SEQUENCE: 59
cgccttaagg tgcagacg                                                  18

<210> SEQ ID NO 60
<211> LENGTH: 21
<212> TYPE: DNA
<213> ORGANISM: Artificial sequence
<220> FEATURE:
<223> OTHER INFORMATION: 3' PCR primer

<400> SEQUENCE: 60
agtggatagg gtgtgtgatg c                                              21

<210> SEQ ID NO 61
<211> LENGTH: 20
<212> TYPE: DNA
<213> ORGANISM: Artificial sequence
<220> FEATURE:
<223> OTHER INFORMATION: 3' PCR primer

<400> SEQUENCE: 61
ctcctagccc ttctgtggtg                                                20
```

PROTECTION OF BETA CELLS FROM IMMUNE ATTACK

This application is a Continuation of International Application PCT/US2018/019862, which was filed on Feb. 27, 2018, which claims the benefit of priority to U.S. Provisional Application No. 62/464,532, which was filed on Feb. 28, 2017, and both of which are incorporated by reference in their entirety.

BACKGROUND

Type 1 diabetes is caused by a malfunctioning immune system that targets and destroys healthy insulin-producing beta cells in the pancreas. Strategies to tame the immune attack on beta cells may ultimately help prevent type 1 diabetes before onset. However, individuals at risk of type 1 diabetes in the general population cannot yet be identified. Furthermore, immune-mediated destruction of beta cells often starts very early in life.

Consequently, a successful immune intervention would help prevent disease in some individuals but will not help patients with long-standing disease or in whom disease-onset could not be predicted in time for prevention. For these patients, a method to replace lost beta cells and restore insulin production is urgently needed and will remain essential even when successful immune therapies exist.

Two approaches have been proposed to replenish beta cell mass in patients with type 1 diabetes. Beta cells could be regenerated by stimulating the patient's own cells to cause beta cell replication or to cause other cell types (e.g. precursor cells, pancreatic ductal cells, exocrine cells, or alpha cells) to become beta cells. The advantages of this approach are that it is non-invasive and that new beta cells would be perfectly well tolerated by the patient compared to an allogenic islet transplant. The critical caveat is that newly generated beta cells will be as susceptible to autoimmune killing as the patient's original beta cells. Therefore, beta cell regeneration would only be effective in combination with a successful immune therapy that abrogates autoimmunity.

Alternatively, beta cells can be provided from external sources. Several groups have demonstrated that induced human pluripotent stem cells (hiPSCs) can be reprogrammed into beta-like cells that secrete insulin in response to glucose stimulation. hiPSCs can be derived from a patient's own blood or skin cells. Conceivably, one day clinicians may be able to use a patient's own cells to generate vast amounts of beta-like cells in the laboratory that could be transplanted back into the same individual. Alternatively, some researchers have postulated that cells could be generated that are 'universal-donor' cells and could be used to treat any patient. Regardless of the source of these newly generated beta-like cells, one key challenge will be to protect them against the autoimmune attack that underlies type 1 diabetes.

Protection against immune killing could be achieved by a physical barrier, and a number of laboratories have a long-standing interest in developing beta cell encapsulation whereby beta cells are packaged within a man-made device that keeps immune cells out. Encapsulation poses many challenges such as packaging a sufficiently large number of cells, allowing proper oxygenation of densely packed cells and preventing fibrosis around the artificial device. Furthermore, encapsulation of beta cell can cause a delay in insulin secretion and action.

Achieving protection without the need for a physical barrier would overcome all of these issues. The killing of beta cells by immune cells proceeds in two stages. First, immune cells must recognize beta cells by interacting with cell surface molecules including HLA molecules. In a second step, immune cells launch an attack to kill beta cells. This attack may come in the form of cytokines, death-receptor ligands (e.g. FasL) or cytolytic molecules (e.g. perforin and granzymes). With the advent of CRISPR/Cas technology and other highly-efficient genome editing methods, it has become possible to precisely engineer hiPSCs. This has led to the prospect of generating gene-modified beta cells with mutations that protect against immune killing.

One approach would then be to target known molecules involved in immune recognition. This strategy may seem promising, however the immune system has evolved many complementary and redundant mechanisms to identify and kill target cells. Driven by the pressures of constantly-evolving pathogens that try to evade host immunity, the immune system has become exceedingly flexible in its ability to find and destroy cells it believes to be diseased. Trying to subvert the immune system by mutating only those molecules we know to be involved in immune recognition may prove futile.

Described herein are unbiased experiments that assess a wide range of genetic modifications to find loss-of-function (LOF) mutations that protect beta cells from autoimmune destruction. These mutations provide therapeutic targets that, individually or in combination, allow genetic engineering to develop beta or beta-like cells resistant to the immune killing that underlies type 1 diabetes. Administration of these engineered beta or beta-like cells may be a novel means to promote survival of beta or beta-like cell transplants in patients with type 1 diabetes.

SUMMARY

In accordance with the description, a composition is provided comprising a human beta-like cell, wherein the beta-like cell is capable of producing insulin in response to glucose, and wherein the beta-like cell is genetically or otherwise modified to inhibit expression of one or more of menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, the genetic modification inhibits expression of menin (SEQ ID No: 1).

In some embodiments, the genetic modification inhibits expression of transcription factor HIVEP2 (SEQ ID No: 2).

In some embodiments, the genetic modification inhibits expression of renalase (SEQ ID No: 3).

In some embodiments, the genetic modification inhibits expression of lengsin (SEQ ID No: 4).

In some embodiments, the genetic modification inhibits expression of eIF-2-alpha kinase activator GCN1 (SEQ ID No: 5).

In some embodiments, the genetic modification inhibits expression of perilipin-4 (SEQ ID No: 6).

In some embodiments, the genetic modification inhibits expression of mediator of RNA polymerase II transcription subunit 11 (SEQ ID No: 7).

In some embodiments, the genetic modification inhibits expression of protein-glutamine gamma-glutamyltransferase 6 (SEQ ID No: 8).

In some embodiments, the genetic modification inhibits expression of zinc finger BED domain-containing protein 3 (SEQ ID No: 9).

In some embodiments, the genetic modification inhibits expression of metabotropic glutamate receptor 2 (SEQ ID No: 10).

In some embodiments, the beta-like cell is a pancreatic beta cell isolated from a human, non-human primate, cow, horse, pig, sheep, goat, dog, cat, or rodent.

In some embodiments, the beta-like cell is generated from a stem cell. In some embodiments, the stem cell is an adult stem cell, pluripotent stem cell, or embryonic stem cell. In some embodiments, the stem cell is a hematopoietic stem cell, bone marrow stromal stem cell, or mesenchymal stem cell.

In some embodiments, the beta-like cell is a cell that is reprogrammed or transdifferentiated. In some embodiments, the reprogrammed or transdifferentiated cell is a pancreatic alpha cell. In some embodiments, the reprogrammed or transdifferentiated cell is a pancreatic exocrine cell. In some embodiments, the reprogrammed or transdifferentiated cell is a gut or stomach cell.

In some embodiments, the genetic modification is a substitution, insertion, deletion, or excision of one or more nucleotides.

In some embodiments, the genetic modification is performed using the CRISPR/Cas9 system. In some embodiments, the guide RNA is selected from the guide RNAs in Table 2 (SEQ ID Nos: 23-35).

In some embodiments, the genetic modification is performed using zinc-finger nucleases.

In some embodiments, the genetic modification is performed using transcription activator-like effector nucleases (TALENs).

In some embodiments, the genetic modification is performed using meganucleases.

In some embodiments, the genetic modification is performed using group one intron encoded endonucleases (GIIEE).

In some embodiments, the genetic modification is within the coding region of the gene, and no gene product is expressed, or a non-functional gene product is produced.

In some embodiments, the genetic modification is not within a coding region of the gene, and no gene product is expressed or a non-functional gene product is produced.

In some embodiments, survival of the beta-like cells over 1, 2, 3, 4, 5, 6, 12, 18, 24, or 36 months is improved compared to beta-like cells without the genetic modification.

In some embodiments, proliferation of beta-like cells over 1, 2, 3, 4, 5, 6, 12, 18, 24, or 36 months is improved compared to beta-like cells without the genetic modification.

In some embodiments, a method of lowering blood glucose in a subject comprises administering any one of the compositions described herein.

In some embodiments, a method of increasing insulin secretion in response to glucose in a subject comprises administering any one of the compositions described herein.

In some embodiments, a method of treating type 1 diabetes in a subject comprises administering any one of the compositions described herein.

In some embodiments, a method of treating type 1 diabetes in a subject comprises administering an agent that genetically modifies any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, a method of preventing the death of pancreatic islet cells comprises administering any one of the compositions described herein.

In some embodiments, a method of preventing the death of pancreatic islet cells comprises administering an agent that genetically modifies any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6) mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, a method of ameliorating type 1 diabetes in a subject comprises administering any one of the compositions described herein. In some embodiments, the subject has a blood sugar level higher than 11.1 mmol/liter or 200 mg/dl.

In some embodiments, the subject is a mammal. In some embodiments, the mammal is a human.

In some embodiments, a composition is administered in combination with an additional treatment.

In some embodiments, the additional treatment is insulin. In some embodiments, the insulin is a rapid-acting, intermediate-acting, or long-acting insulin.

In some embodiments, the additional treatment is a glucagon-like peptide analog or agonist, dipeptidyl peptidase-4 inhibitor, amylin analog, biguanide, thiazolidinedione, sulfonylurea, meglitinide, alpha-glucosidase inhibitor, or sodium/glucose transporter 2 inhibitor.

In some embodiments, the beta-like cells are administered by transplant into the pancreas, liver, or fat pads via surgery, injection, or infusion.

In some embodiments, a method of treating type 1 diabetes in a subject comprises administering a composition that inhibits the function of any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, the composition inhibits the function of metabotropic glutamate receptor 2 (SEQ ID No: 10). In some embodiments, the composition is LY341495, (2S)-α-ethylglutamic acid (EGLU), or MGS-0039.

In some embodiments, a method of preventing the death of pancreatic islet cells comprises administering a composition that inhibits the function of any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, the composition inhibits the function of metabotropic glutamate receptor 2 (SEQ ID No: 10). In some embodiments, the composition is LY341495, (2S)-α-ethylglutamic acid (EGLU), or MGS-0039.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 5A shows location of primers in relation to gRNA targeting site. FIG. 5B shows design of the T7E1 assay. FIG. 5C shows editing data in NIT-1 stable cell lines.

FIG. 6A shows an overview of the assay. FIG. 6B shows results of staining for active caspase 3 at 24 hours. FIG. 6C shows a summary of cell death in different conditions. The ratios represent ratios of splenocytes to NIT-1 cells. For example, 50:1 indicates 50-times more splenocytes than NIT-1 cells, while 0:1 indicates NIT-1 cells cultured without splenocytes. $P<0.0001$ =****.

DESCRIPTION OF THE SEQUENCES

Figure 1:
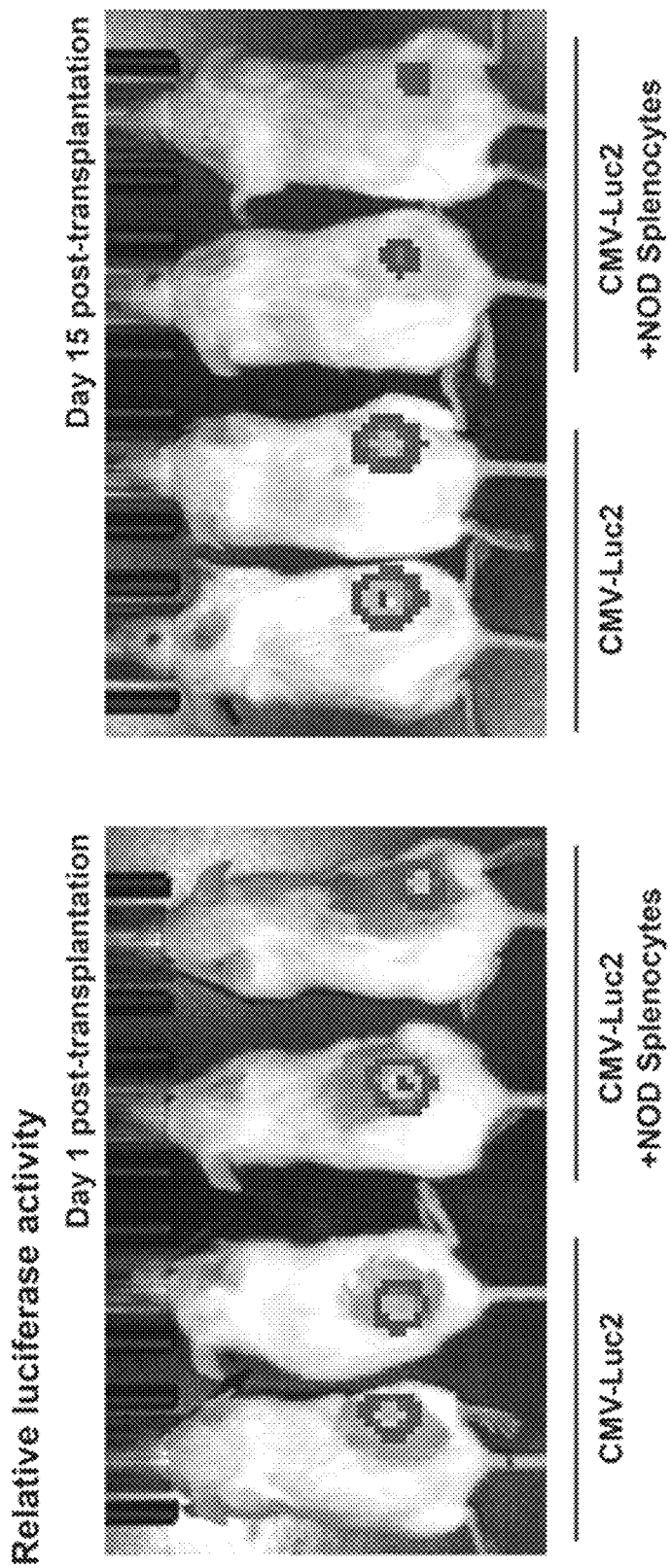
FIG. 1 shows non-invasive live imaging of CMV-Luc2 lentivirus infected NIT-1 cells in non-obese diabetic (NOD) .severe combined immune deficiency (scid) mice (NOD.scid mice). Images on left show imaging on Day 1 post-transplantation, while images on the right show imaging on Day 15 post-transplantation. One set of mice also had transfer of splenocytes from diabetic NOD mice (NOD splenocytes).

Table 1 provides a listing of certain sequences referenced herein.

TABLE 1

Description of the Sequences

| Description | Sequences | SEQ ID NO |
|---|---|---|
| Human Menin protein (MEN1 gene product) (UniprotKB-O00255) | MGLKAAQKTLFPLRSIDDVVRLFAAELGREEPDLVLLSLVLGFVE HFLAVNRVIPTNVPELTFQPSPAPDPPGGLTYFPVADLSIIAALY ARFTAQIRGAVDLSLYPREGGVSSRELVKKVSDVIWNSLSRSYFK DRAHIQSLFSFITGWSPVGTKLDSSGVAFAVVGACQALGLRDVHL ALSEDHAWVVFGPNGEQTAEVTWHGKGNEDRRGQTVNAGVAERSW LYLKGSYMRCDRKMEVAFMVCAINPSIDLHTDSLELLQLQQKLLW LLYDLGHLERYPMALGNLADLEELEPTPGRPDPLTLYHKGIASAK TYYRDEHIYPYMYLAGYHCRNRNVREALQAWADTATVIQDYNYCR EDEEIYKEFFEVANDVIPNLLKEAASLLEAGEERPGEQSQGTQSQ GSALQDPECFAHLLRFYDGICKWEEGSPTPVLHVGWATFLVQSLG RFEGQVRQKVRIVSREAEAAEAEEPWGEEAREGRRRGPRRESKPE EPPPPKKPALDKGLGTGQGAVSGPPRKPPGTVAGTARGPEGGSTA QVPAPTASPPPEGPVLTFQSEKMKGMKELLVATKINSSAIKLQLT AQSQVQMKKQKVSTPSDYTLSFLKRQRKGL | 1 |
| Human transcription factor HIVEP2 (HIVEP2 gene product) (UniProtKB-P31629) | MDTGDTALGQKATSRSGETDKASGRWRQEQSAVIKMSTFGSHEGQ RQPQIEPEQIGNTASAQLFGSGKLASPSEVVQQVAEKQYPPHRPS PYSCQHSLSFPQHSLPQGVMHSTKPHQSLEGPPWLFPGPLPSVAS EDLFPFPIHGHSGGYPRKKISSLNPAYSQYSQKSIEQAEEAHKKE HKPKKPGKYICPYCSRACAKPSVLKKHIRSHTGERPYPCIPCGFS FKTKSNLYKHRKSHAHAIKAGLVPFTESAVSKLDLEAGFIDVEAE IHSDGEQSTDTDEESSLFAEASDKMSPGPPIPLDIASRGGYHGSL EESLGGPMKVPILIIPKSGIPLPNESSQYIGPDMLPNPSLNTKAD DSHTVKQKLALRLSEKKGQDSEPSLNLLSPHSKGSTDSGYFSRSE SAEQQISPPNTNAKSYEEIIFGKYCRLSPRNALSVTTTSQERAAM GRKGIMEPLPHVNTRLDVKMFEDPVSQLIPSKGDVDPSQTSMLKS TKFNSESRQPQIIPSSIRNEGKLYPANFQGSNPVLLEAPVDSSPL IRSNSVPTSSATNLTIPPSLRGSHSFDERMTGSDDVFYPGTVGIP PQRMLRRQAAFELPSVQEGHVEVEHHGRMLKGISSSSLKEKKLSP GDRVGYDYDVCRKPYKKWEDSETPKQNYRDISCLSSLKHGGEYFM DPVVPLQGVPSMFGTICENRKRRKEKSVGDEEDIPMICSSIVSTP | 2 |

TABLE 1-continued

Description of the Sequences

| Description | Sequences | SEQ ID NO |
|---|---|---|
| | VGIMASDYDPKLQMQEGVRSGFAMAGHENLSHGHTERFDPCRPQL<br>QPGSPSLVSEESPSAIDSDKMSDLGGRKPPGNVISVIQHTNSLSR<br>PNSFERSESAELVACTQDKAPSPSETCDSEISEAPVSPEWAPPGD<br>GAESGGKPSPSQQVQQQSYHTQPRLVRQHNIQVPEIRVTEEPDKP<br>EKEKEAQSKEPEKPVEEFQWPQRSETLSQLPAEKLPPKKKRLRLA<br>DMEHSSGESSFESTGTGLSRSPSQESNLSHSSSFSMSFEREETSK<br>LSALPKQDEFGKHSEFLTVPAGSYSLSVPGHHHQKEMRRCSSEQM<br>PCPHPAEVPEVRSKSFDYGNLSHAPVSGAAASTVSPSRERKKCFL<br>VRQASFSGSPEISQGEVGMDQSVKQEQLEHLHAGLRSGWHHGPPA<br>VLPPLQQEDPGKQVAGPCPPLSSGPLHLAQPQIMHMDSQESLRNP<br>LIQPTSYMTSKHLPEQPHLFPHQETIPFSPIQNALFQFQYPTVCM<br>VHLPAQQPPWWQAHFPHPFAQHPQKSYGKPSFQTEIHSSYPLEHV<br>AEHTGKKPAEYAHTKEQTYPCYSGASGLHPKNLLPKFPSDQSSKS<br>TETPSEQVLQEDFASANAGSLQSLPGTVVPVRIQTHVPSYGSVMY<br>TSISQILGQNSPAIVICKVDENMIQRTLVINAAMQGIGFNIAQVL<br>GQHAGLEKYPIWKAPQTLPLGLESSIPLCLPSTSDSVATLGGSKR<br>MLSPASSLELFMETKQQKRVKEEKMYGQIVEELSAVELTNSDIKK<br>DLSRPQKPQLVRQGCASEPKDGLQSGSSSFSSLSPSSSQDYPSVS<br>PSSREPFLPSKEMLSGSRAPLPGQKSSGPSESKESSDELDIDETA<br>SDMSMSPQSSSLPAGDGQLEEEGKGHKRPVGMLVRMASAPSGNVA<br>DSTLLLTDMADFQQILQFPSLRTTTTVSWCFLNYTKPNYVQQATF<br>KSSVYASWCISSCNPNPSGLNTKTTLALLRSKQKITAEIYTLAAM<br>HRPGTGKLTSSSAWKQFTQMKPDASFLFGSKLERKLVGNILKERG<br>KGDIHGDKDIGSKQTEPIRIKIFEGGYKSNEDYVYVRGRGRGKYI<br>CEECGIRCKKPSMLKKHIRTHTDVRPYVCKLCNFAFKTKGNLTKH<br>MKSKAHMKKCLELGVSMTSVDDTETEEEAENLEDLHKAAEKHSMSS<br>ISTDHQFSDAEESDGEDGDDNDDDDEDEDDFDDQGDLTPKTRSRS<br>TSPQPPRFSSLPVNVGAVPHGVPSDSSLGHSSLISYLVTLPSIRV<br>TQLMTPSDSCEDTQMTEYQRLFQSKSTDSEPDKDRLDIPSCMDEE<br>CMLPSEPSSSPRDFSPSSHHSSPGYDSSPCRDNSPKRYLIPKGDL<br>SPRRHLSPRRDLSPMRHLSPRKEAALRREMSQRDVSPRRHLSPRR<br>PVSPGKDITARRDLSPRRERRYMTTIRAPSPRRALYHNPPLSMGQ<br>YLQAEPIVLGPPNLRRGLPQVPYFSLYGDQEGAYEHPGSSLFPEG<br>PNDYVFSHLPLHSQQQVRAPIPMVPVGGIQMVHSMPPALSSLHPS<br>PTLPLPMEGFEEKKGASGESFSKDPYVLSKQHEKRGPHALQSSGP<br>PSTPSSPRLLMKQSTSEDSLNATEREQEENIQTCTKAIASLRIAT<br>EEAALLGPDQPARVQEPHQNPLGSAHVSIRHFSRPEPGQPCTSAT<br>HPDLHDGEKDNFGTSQTPLAHSTFYSKSCVDDKQLDFHSSKELSS<br>STEESKDPSSEKSQLH | |
| Human renalase protein (RNLS gene product) (UniProtKB-Q5VYX0) | MAQVLIVGAGMTGSLCAALLRRQTSGPLYLAVWDKAEDSGGRMIT<br>ACSPHNPQCTADLGAQYITCTPHYAKKHQRFYDELLAYGVLRPLS<br>SPIEGMVMKEGDCNFVAPQGISSIIKHYLKESGAEVYFRHRVTQI<br>NLRDDKWEVSKQTGSPEQFDLIVLTMPVPEILQLQGDITTLISEC<br>QRQQLEAVSYSSRYALGLFYEAGTKIDVPWAGQYITSNPCIRPVS<br>IDNKKRNIESSEIGPSLVIHTTVPFGVTYLEHSIEDVQELVFQQL<br>ENILPGLPQPIATKCQKWRHSQVTNAAANCPGQMTLHHKPFLACG<br>GDGFTQSNFDGCITSALCVLEALKNYI | 3 |
| Human lengsin (LGSN gene product) (UniProtKB-Q5TDP6) | MNNEEDLLQEDSTRDEGNETEANSMNTLRRTRKKVTKPYVCSTEV<br>GETDMSNSNDCMRDSSQILTPPQLSSRMKHIRQAMAKNRLQFVRF<br>EATDLHGVSRSKTIPAHFFQEKVSHGVCMPRGYLEVIPNPKDNEM<br>NNIRATCFNSDIVLMPELSTFRVLPWADRTARVICDTFTVTGEPL<br>LTSPRYIAKRQLSHLQASGFSLLSAFIYDFCIFGVPEILNSKIIS<br>FPALTFLNNHDQPFMQELVDGLYHTGANVESFSSSTRPGQMEISF<br>LPEFGISSADNAFTLRTGVKEVARKYNYIASFFIETGFCDSGILS<br>HSLWDVDRKKNMFCSTSGTEQLTITGKKWLAGLLKHSAALSCLMA<br>PSVSCRKRYSKDRKDLKKSVPTTWGYNDNSCIFNIKCHGEKGTRI<br>ENKLGSATANPYLVLAATVAAGLDGLHSSNEVLAGPDESTDFYQV<br>EPSEIPLKLEDALVALEEDQCLRQALGETFIRYFVAMKKYELENE<br>EIAAERNKFLEYFI | 4 |
| Human eIF-2-alpha kinase activator GCN1 (GCN1 gene product) (UniProtKB-Q92616) | MAADTQVSETLKRFAGKVTTASVKERREILSELGKCVAGKDLPEG<br>AVKGLCKLFCLTLHRYRDAASRRALQAAIQQLAEAQPEATAKNLL<br>HSLQSSGIGSKAGVPSKSSGSAALLALTWTCLLVRIVFPSRAKRQ<br>GDIWNKLVEVQCLLLLEVLGGSHKHAVDGAVKKLTKLWKENPGLV<br>EQYLSAILSLEPNQNYAGMLGLLVQFCTSHKEMDVVSQHKSALLD<br>FYMKNILMSKVKPPKYLLDSCAPLLRYLSHSEFKDLILPTIQKSL<br>LRSPENVIETISSLLASVTLDLSQYAMDIVKGLAGHLKSNSPRLM<br>DEAVLALRNLARQCSDSSAMESLTKHLFAILGGSEGKLTVVAQKM<br>SVLSGIGSVSHHVVSGPSSQVLNGIVAELFIPFLQQEVHEGTLVH<br>AVSVLALWCNRFTMEVPKKLTEWFKKAFSLKTSTSAVRHAYLQCM<br>LASYRGDTLLQALDLLPLLIQTVEKAASQSTQVPTITEGVAAALL<br>LLKLSVADSQAEAKLSSFWQLIVDEKKQVFTSEKFLVMASEDALC | 5 |

TABLE 1-continued

Description of the Sequences

| Description | Sequences | SEQ ID NO |
|---|---|---|
| | TVLHLTERLFLDHPHRLTGNKVQQYHRALVAVLLSRTWHVRRQAQ QTVRKLLSSLGGFKLAHGLLEELKTVLSSHKVLPLEALVTDAGEV TEAGKAYVPPRVLQEALCVISGVPGLKGDVTDTEQLAQEMLIISH HPSLVAVQSGLWPALLARMKIDPEAFITRHLDQIIPRMTTQSPLN QSSMNAMGSLSVLSPDRVLPQLISTITASVQNPALRLVTREEFAI MQTPAGELYDKSIIQSAQQDSIKKANMKRENKAYSFKEQIIELEL KEEIKKKKGIKEEVQLTSKQKEMLQAQLDREAQVRRRLQELDGEL EAALGLLDIILAKNPSGLTQYIPVLVDSFLPLLKSPLAAPRIKNP FLSLAACVMPSRLKALGTLVSHVTLRLLKPECVLDKSWCQEELSV AVKRAVMLLHTHTITSRVGKGEPGAAPLSAPAFSLVFPFLKMVLT EMPHHSEEEEEWMAQILQILTVQAQLRASPNTPPGRVDENGPELL PRVAMLRLLTWVIGTGSPRLQVLASDTLTTLCASSSGDDGCAFAE QEEVDVLLCALQSPCASVRETVLRGLMELHMVLPAPDTDEKNGLN LLRRLWVVKFDKEEEIRKLAERLWSMMGLDLQPDLCSLLIDDVIY HEAAVRQAGAEALSQAVARYQRQAAEVMGRLMEIYQEKLYRPPPV LDALGRVISESPPDQWEARCGLALALNKLSQYLDSSQVKPLFQFF VPDALNDRHPDVRKCMLDAALATLNTHGKENVNSLLPVFEEFLKN APNDASYDAVRQSVVVLMGSLAKHLDKSDPKVKPIVAKLIAALST PSQQVQESVASCLPPLVPAIKEDAGGMIQRLMQQLLESDKYAERK GAAYGLAGLVKGLGILSLKQQEMMAALTDAIQDKKNFRRREGALF AFEMLCTMLGKLFEPYVVHVLPHLLLCFGDGNQYVREAADDCAKA VMSNLSAHGVKLVLPSLLAALEEESWRTKAGSVELLGAMAYCAPK QLSSCLPNIVPKLTEVLTDSHVKVQKAGQQALRQIGSVIRNPEIL AIAPVLLDALTDPSRKTQKCLQTLLDTKFVHFIDAPSLALIMPIV QRAFQDRSTDTRKMAAQIIGNMYSLTDQKDLAPYLPSVTPGLKAS LLDPVPEVRTVSAKALGAMVKGMGESCFEDLLPWLMETLTYEQSS VDRSGAAQGLAEVMAGLGVEKLEKLMPEIVATASKVDIAPHVRDG YIMMFNYLPITFGDKFTPYVGPIIPCILKALADENEFVRDTALRA GQRVISMYAETAIALLLPQLEQGLFDDLWRIRFSSVQLLGDLLFH ISGVIGKMITETASEDDNFGTAQSNKAIITALGVERRNRVLAGLY MGRSDTQLVVRQASLHVWKIVVSNTPRTLREILPTLFGLLLGFLA STCADKRTIAARTLGDLVRKLGEKILPEIIPILEEGLRSQKSDER QGVCIGLSEIMKSTSRDAVLYFSESLVPTARKALCDPLEEVREAA AKTFEQLHSTIGHQALEDILPFLLKQLDDEEVSEFALDGLKQVMA IKSRVVLPYLVPKLTTPPVNTRVLAFLSSVAGDALTRHLGVILPA VMLALKEKLGTPDEQLEMANCQAVILSVEDDIGHRIIIEYLLEAT RSPEVGMRQAAAIILNIYCSRSKADYTSHLRSLVSGLIRLFNDSS PVVLEESWDALNAITKKLDAGNQLALIEELHKEIRLIGNESKGEH VPGFCLPKKGVISILPVLREGVLIGSPEQKEEAAKALGLVIRLTS ADALRPSVVSITGPLIRILGDRFSWNVKAALLETLSLLLAKVGIA LKPFLPQLQTTFTKALQDSNRGVRLKAADALGKLISIHIKVDPLF TELLNGIRAMEDPGVRDTMLQALRPVIQGAGAKVDAVIRKNIVSL LLSMLGHDEDNTRISSAGCLGELCAFLTEEELSAVLQQCLLADVS GIDWMVRHGRSLALSVAVNVAPGRLCAGRYSSDVQEMILSSATAD RIPIAVSGVRGMGFLMRHHIETGGGQLPAKLSSLPVKCLQNPSSD IRLVAEKMIWWANKDPLPPLDPQAIKPILKALLDNIKDKNIVVRA YSDQAIVNLLKMRQGEEVFQSLSKILDVASLEVLNEVNRRSLKKL ASQADSTEQVDDTILT | |
| Human perilipin-4 (PLIN4 gene product) (UniProtKB-Q96Q06) | MQTLGSFFGSLPGFSSARNLVANAHSSARARPAADPTGAPAAEAA QPQAQVAAHPEQTAPWTEKELQPSEKQMVSGAKDLVCSKMSRAKD AVSSGVASVVDVAKGVVQGGLDTTRSALIGTKEVVSSGVTGAMDM AKGAVQGGLDTSKAVLTGTKDTVSTGLTGAVNVAKGTVQAGVDTT KTVLIGTKDIVITGVMGAVNLAKGIVQTGVETSKAVLIGTKDAVS TGLTGAVNVARGSIQTGVDTSKTVLTGTKDTVCSGVTGAMNVAKG TIQTGVDTSKTVLTGTKDTVCSGVTGAMNVAKGTIQTGVDTSKTV LTGTKDTVCSGVTGAMNVAKGTIQTGVDTTKTVLTGTKNTVCSGV TGAVNLAKEAIQGGLDTIKSMVMGTKDIMSTGLIGAANVAKGAMQ TGLNTTQNIATGTKDTVCSGVTGAMNLARGTIQTGVDTTKIVLTG TKDTVCSGVTGAANVAKGAVQGGLDTTKSVLTGTKDAVSTGLTGA VNVAKGTVQTGVDTTKTVLTGTKDTVCSGVTSAVNVAKGAVQGGL DTTKSVVIGTKDTMSTGLTGAANVAKGAVQTGVDTAKTVLTGTKD TVTTGLVGAVNVAKGTVQTGMDTTKTVLTGTKDTIYSGVTSAVNV AKGAVQTGLKTTQNIATGTKNTFGSGVTSAVNVAKGAAQTGVDTA KTVLTGTKDTVTTGLMGAVNVAKGTVQTSVDTTKTVLTGTKDTVC SGVTGAANVAKGAIQGGLDTTKSVLTGTKDAVSTGLTGAVKLAKG TVQTGMDTTKTVLTGTKDAVCSGVTGAANVAKGAVQMGVDTAKTV LTGTKDTVCSGVTGAANVAKGAVQTGLKTTQNIATGTKNTLGSGV TGAAKVAKGAVQGGLDTIKSVLIGTKDAVSTGLIGAVNLAKGIVQ TGVDTSKTVLTGTKDTVCSGVTGAVNVAKGTVQTGVDTAKTVLSG AKDAVTTGVTGAVNVAKGTVQTGVDASKAVLMGTKDTVFSGVTGA MSMAKGAVQGGLDTTKTVLTGTKDAVSAGLMGSGNVATGATHTGL STFQNWLPSTPATSWGGLTSSRTTDNGGEQTALSPQEAPFSGIST PPDVLSVGPEPAWEAAATTKGLATDVATFTQGAAPGREDTGLLAT | 6 |

TABLE 1-continued

Description of the Sequences

| Description | Sequences | SEQ ID NO |
|---|---|---|
| | THGPEEAPRLAMLQNELEGLGDIFHPMNAEEQAQLAASQPGPKVL SAEQGSYFVRLGDLGPSFRQRAFEHAVSHLQHGQFQARDTLAQLQ DCFRLIEKAQQAPEGQPRLDQGSGASAEDAAVQEERDAGVLSRVC GLLRQLHTAYSGLVSSLQGLPAELQQPVGRARHSLCELYGIVASA GSVEELPAERLVQSREGVHQAWQGLEQLLEGLQHNPPLSWLVGPF ALPAGGQ | |
| Human mediator of RNA polymerase II transcription subunit 11 (MED11 gene product) (UniProtKB-Q9P086) | MATYSLANERLRALEDIEREIGAILQNAGTVILELSKEKTNERLL DRQAAAFTASVQHVEAELSAQIRYLTQVATGQPHEGSSYSSRKDC QMALKRVDYARLKLSDVARTCEQMLEN | 7 |
| Human protein-glutamine gamma-glutamyl-transferase (6TGM3L gene product) (UniProtKB-O95932) | MAGIRVTKVDWQRSRNGAAHHTQEYPCPELVVRRGQSFSLTLELS RALDCEEILIFTMETGPRASEALHTKAVFQTSELERGEGWTAARE AQMEKTLTVSLASPPSAVIGRYLLSIRLSSHRKHSNRRLGEFVLL FNPWCAEDDVFLASEEERQEYVLSDSGIIFRGVEKHIRAQGWNYG QFEEDILNICLSILDRSPGHQNNPATDVSCRHNPIYVTRVISAMV NSNNDRGVVQGQWQGKYGGGTSPLHWRGSVAILQKWLKGRYKPVK YGQCWVFAGVLCTVLRCLGIATRVVSNFNSAHDTDQNLSVDKYVD SFGRTLEDLTEDSMWNFHVWNESWFARQDLGPSYNGWQVLDATPQ EESEGVFRCGPASVTAIREGDVHLAHDGPFVFAEVNADYITWLWH EDESRERVYSNTKKIGRCISTKAVGSDSRVDITDLYKYPEGSRKE RQVYSKAVNRLFGVEASGRRIWIRRAGGRCLWRDDLLEPATKPSI AGKFKVLEPPMLGHDLRLALCLANLTSRAQRVRVNLSGATILYTR KPVAEILHESHAVRLGPQEEKRIPITISYSKYKEDLTEDKKILLA AMCLVTKGEKLLVEKDITLEDFITIKVLGPAMVGVAVTVEVTVVN PLIERVKDCALMVEGSGLLQEQLSIDVPTLEPQERASVQFDITPS KSGPRQLQVDLVSPHFPDIKGFVIVHVATAK | 8 |
| Human zinc finger BED domain-containing protein 3 (ZBED3 gene product) (UniProtKB-Q96IU2) | MRSGEPACTMDQARGLDDAAARGGQCPGLGPAPTPTPPGRLGAPY SEAWGYFHLAPGRPGHPSGHWATCRLCGEQVGRGPGFHAGTSALW RHLRSAHRRELESSGAGSSPPAAPCPPPPGPAAAPEGDWARLLEQ MGALAVRGSRRERELERRELAVEQGERALERRRRALQEEERAAAQ ARRELQAEREALQARLRDVSRREGALGWAPAAPPPLKDDPEGDRD GCVITKVLL | 9 |
| Human metabotropic glutamate receptor 2 (GRM2 gene product) (UniProtKB-Q14416) | MGSLLALLALLLLWGAVAEGPAKKVLTLEGDLVLGGLFPVHQKGG PAEDCGPVNEHRGIQRLEAMLFALDRINRDPHLLPGVRLGAHILD SCSKDTHALEQALDFVRASLSRGADGSRHICPDGSYATHGDAPTA ITGVIGGSYSDVSIQVANLLRLFQIPQISYASTSAKLSDKSRYDY FARTVPPDFFQAKAMAEILRFFNWTYVSTVASEGDYGETGIEAFE LEARARNICVATSEKVGRAMSRAAFEGVVRALLQKPSARVAVLFT RSEDARELLAASQRLNASFTWVASDGWGALESVVAGSEGAAEGAI TIELASYPISDFASYFQSLDPWNNSRNPWFREFWEQRFRCSFRQR DCAAHSLRAVPFEQESKIMFVVNAVYAMAHALHNMHRALCPNTTR LCDAMRPVNGRRLYKDFVLNVKFDAPFRPADTHNEVRFDRFGDGI GRYNIFTYLRAGSGRYRYQKVGYWAEGLILDTSLIPWASPSAGPL PASRCSEPCLQNEVKSVQPGEVCCWLCIPCQPYEYRLDEFTCADC GLGYWPNASLTGCFELPQEYIRWGDAWAVGPVTIACLGALATLFV LGVFVRHNATPVVKASGRELCYILLGGVFLCYCMTFIFIAKPSTA VCTLRRLGLGTAFSVCYSALLTKTNRIARIFGGAREGAQRPRFIS PASQVAICLALISGQLLIVVAWLVVEAPGTGKETAPERREVVTLR CNHRDASMLGSLAYNVLLIALCTLYAFKTRKCPENFNEAKFIGFT MYTTCIIWLAFLPIFYVTSSDYRVQTTTMCVSVSLSGSVVLGCLF APKLHIILFQPQKNVVSHRAPTSRFGSAAARASSSLGQGSGSQFV PTVCNGREVVDSTTSSL | 10 |
| Mouse menin (UniProtKB-O88559) | MGLKAAQKTLFPLRSIDDVVRLFAAELGREEPDLVLLSLVLGFVE HFLAVNRVIPTNVPELTFQPSPAPDPPGGLTYFPVADLSIIAALY ARFTAQIRGAVDLSLYPREGGVSSRELVKKVSDVIWNSLSRSYFK DRAHIQSLFSFITGTKLDSSGVAFAVVGACQALGLRDVHLALSED HAWVFGPNGEQTAEVTWHGKGNEDRRGQTVNAGVAERSWLYLKG SYMRCDRKMEVAFMVCAINPSIDLHTDSLELLQLQQKLLWLLYDL | 11 |

TABLE 1-continued

Description of the Sequences

| Description | Sequences | SEQ ID NO |
|---|---|---|
| | GHLERYPMALGNLADLEELEPTPGRPDPLTLYHKGIASAKTYYQD EHIYPYMYLAGYHCRNRNVREALQAWADTATVIQDYNYCREDEEI YKEFFEVANDVIPNLLKEAASLLETGEERTGEQAQGTQGQGSALQ DPECFAHLLRFYDGICKWEEGSPTPVLHVGWATFLVQSLGRFEGQ VRQKVHIVSREAEAAEAEEPWGDEAREGRRRGPRRESKPEEPPPP KKPALDKGPGSGQSAGSGPPRKTSGTVPGTTRGGQEVGNAAQAPA PAASPPPEGPVLTFQSEKMKGMKELLVATKINSSAIKLQLTAQSQ VQMKKQKVSTPSDYTLSFLKRQRKGL | |
| Mouse transcription factor Hivep2 (UniProtKB-Q3UHF7) | MDTGDTALGQKATSRSGETDSVSGRWRQEQSAVLKMSTFSSQEGP RQPQIDPEQIGNAASAQLFGSGKLASPGEGLHQVTEKQYPPHRPS PYPCQHSLSFPQHSLSQGMTHSHKPHQSLEGPPWLFPGPLPSVAS EDLFPFPMHGHSGGYPRKKISNLNPAYSQYSQKSIEQAEDAHKKE HKPKKPGKYICPYCSRACAKPSVLKKHIRSHTGERPYPCIPCGFS FKIKSNLYKHRKSHAHAIKAGLVPFTESSVSKLDLEAGFIDVEAE IHSDGEQSTDIDEESSLFAEASDKVSPGPPVPLDIASRGGYHGSL EESLGGPMKVPILIIPKSGIPLASEGSQYLSSEMLPNPSLNAKAD DSHTVKQKLALRLSEKKGQDSEPSLNLLSPHSKGSTDSGYFSRSE SAEQQISPPNTNAKSYEEIIFGKYCRLSPRNTLSVTPTGQRERTAM GRRGIMEPLPHLNTRLEVKMFEDPISQLNPSKGEMDPGQINMLKT TKFNSECRQPQAIPSSVRNEGKPYPGNFLGSNPMLLEAPVDSSPL IRSNSMPTSSATNLSVPPSLRGSHSFDERMTGSDDVFYPGTVGIP PQRMLRRQAAFELPSVQEGHMESEHPARVSKGLASPSLKEKKLLP GDRPGYDYDVCRKPYKKWEDSETLKQSYLGSFKQGGEYFMDPSVP VQGVPTMFGTTCENRKRRKEKSVGDEEDVPMICGGMGNAPVGMMS SEYDPKLQDGGRSGFAMTAHESLAHGHSDRLDPARPQLPSRSPSL GSEDLPLAADPDKMTDLGKKPPGNVISVIQHTNSLSRPNSFERSE STEMVACPQDKTPSPAETCDSEVLEAPVSPEWAPPGDGGESGSKP TPSQQVPQHSYHAQPRLVRQHNIQVPEIRVTEEPDKPEKEKEAPT KEPEKPVEEFQWPQRSETLSQLPAEKLPPKKKRLRLADLEHSSGE SSFESTGTGLSRSPSQESNLSHSSSFSMSFDREETVKLTAPPKQD ESGKHSEFLTVPAGSYSLSVPGHHHQKEMRRCSSEQMPCPHPTEV PEIRSKSFDYGNLSHAPVAGTSPSTLSPSRERKKCFLVRQASFSG SPEIAQGEAGVDPSVKQEHMEHLHAGLRAAWSSVLPPLPGDDPGK QVGTCGPLSSGPPLHLTQQQIMHMDSQESLRNPLIQPTSYMTSKH LPEQPHLFPHQDAVPFSPIQNALFQFQYPTVCMVHLPAQQPPWWQ THFPHPFAPHPQNSYKPPFQADLHSSYPLEHVAEHTGKKSADYP HAKEQTYPCYSGTSGLHSKNLPLKFPSDPGSKSTETPTEQLLRED FASENAGPLQSLPGTVVPVRIQTHVPSYGSVMYTSISQILGQNSP AIVICKVDENMIQRTLVINAAMQGIGLNIAQVLGQHTGLEKYPLW KVPQTLPLGLESSIPLCLPSTSDNAASLGGSKRMLSPASSLELFM ETKQQKRVKEEKMYGQIVEELSAVELTNSDIKKGLSRPQKPQLVR QGCASEPKDGCFQSRSSSFSSLSPSSSQDHPSASGPFPPNREILP GSRAPPRRKFSGPSESRESSDELDMDETSSDMSMSPQSSALPTGG GQQEEEGKARKLPVSMLVHMASGPGGNVANSTLLFTDVADFQQIL QFPSLRTTTTVSWCFLNYTKPSFVQQATFKSSVYASWCISSCNPN PSGLNTKTTLALLRSKQKITAEIYTLAAMHRPGAGKLTSSSVWKQ FAQMKPDAPFLFGNKLERKLAGNVLKERGKGEIHGDKDLGSKQTE PIRIKIFEGGYKSNEDYVYVRGRGRGKYICEECGIRCKKPSMLKK HIRTHTDVRPYVCKLCNFAFKTKGNLTKHMKSKAHMKKCLELGVS MTSVDDTETEEAENMEELHKTSEKHSMSGISTDHQFSDAEESDGE DGDDNDDDDEDDDDFDDQGDLTPKTRSRSTSPQPPRFSSLPVNVG AVAHGVPSDSSLGHSSLISYLVTLPSIQVTQLMTPSDSCDDTQMT EYQRLFQSKSTDSEPDKDRLDIPSSMDEEAMLSSEPSSSPRDFSP SSYRSSPGYDSSPCRDNSPKRYLIPKGDLSPRRHLSPRRDLSPMR HLSPRKEAALRREMSQGDASPRRHLSPRRPLSPGKDITARRDLSP RRERRYMTTIRAPSPRRALYPNPPLSMGQYLQTEPIVLGPPNLRR GIPQVPYFSLYGDQEGAYEHHGSSLFPEGPTDYVFSHLPLHSQQQ VRAPIPMVPVGGIQMVHSLPPALSGLHPPPTLPLPTEGSEEKKGA PGEAFAKDPYILSRRHEKQAPQVLQSSGLPSSPSSPRLLMKQSTS EDSLNSTEREQEENIQTCTKAIASLRIATEEAALLGADPPTWVQE SPQKPLESAHVSIRHFGGPEPGQPCTSAAHPDLHDGEKDTFGTSQ TAVAHPTFYSKSSVDEKRVDFQSSKELSLSTEEGNEPSPEKNQLH | 12 |
| Mouse renalase (UniProtKB-A7RDN6) | MSRVLVVGAGLTGSLCAALLRKEITAPLYLGLWDKGGDIGGRMIT ASSPHNPRCTADLGAQYITCSPHYVKEHQNFYEELLAHGILKPLT SPIEGMKGKEGDCNFVAPQGFSSVIKYYLKKSGAEVSLKHCVTQI HLKDNKWEVSTDTGSAEQFDLVILTMPAPQILELQGDIVNLISER QREQLKSVSYSSRYALGLFYEVGMKIGVPWSCRYLSSHPCICFIS IDNKKRNIESSECGPSVVIQTTVPFGVQHLEASEADVQKLMIQQL ETILPGLPQPVATICHKWTYSQVTSSVSDRPGQMTLHLKPFLVCG GDGFTHSNFNGCISSALSVMKVLKRYI | 13 |

TABLE 1-continued

Description of the Sequences

| Description | Sequences | SEQ ID NO |
|---|---|---|
| Mouse lengsin (UniProtKB-Q8CIX8) | MIDEGDLAQEDTAKDEGNVIEGSRMSKLRRARRKVIKPHLCSMDG EEIAKANSSEMSRNQIADLSKPGSAESWSSHSAKDAYHPTPVVKP SLPSALAGAPDAEFSPNTDPTRYNAQSFNPPQLSARMKHIKQEMA KNHLQFVRFEATDLHGVSRSKSIPAQFFQEKVIHGVFMPRGYLEL MPNPKDNEVNHIRATCFNSDIVLMPELSTFRVLPWAERTARVICD TFTVTGEPLLTSPRYIAKRQLRQLQDAGFCLLSAFIYDFCIFGVP EVINSKTISFPASTLLSNHDQPFMQELVEGLYQTGANVESFSSST RPGQMEICFLPEFGISSADNAFTLRTGLQEVARRYNYIASLVIET GFCNSGILSHSIWDVGGKTNMFCSGSGVERLTLTGKKWLAGLLKH SAALSCLMAPAVNCRKRYCKDSRDLKDSVPTTWGYNDNSCALNIK CHGEKGTQIENKLGSATANPYLVLAATVAAGLDGLQSSDGAAAGS DESQDLYQPEPSEIPLKMEDALAALEQDECLKQALGETFIRYFVA MKKYELENEETDAEGNKFLEYFI | 14 |
| Mouse eIF-2-alpha kinase activator GCN1 (Gcn1l1) | MAADTQVSETLKRFAVKVTTASVKERREILSELGRCIAGKDLPEG AVKGLCKLFCLTLHRYRDAASRRALQAAIQQLAEAQPEATAKNLL HSLQSSGVGSKACVPSKSSGSAALLALTWTCLLVRIVFPLKAKRQ GDIWNKLVEVQCLLLLEVLGGSHKHAVDGAVKKLTKLWKENPGLV EQYFSAILSLEPSQNYAAMLGLLVQFCTNHKEMDAVSQHKSTLLE FYVKNILMSKAKPPKYLLDNCAPLLRFMSHSEFKDLILPTIQKSL LRSPENVIETISSLLASVTLDLSQYALDIVKGLANQLKSNSPRLM DEAVLALRNLARQCSDSSATEALTKHLFAILGGSEGKLTIIAQKM SVLSGIGSLSHHVVSGPSGQVLNGCVAELFIPFLQQEVHEGTLVH AVSILALWCNRFTTEVPKKLTDWFKKVFSLKTSTSAVRHAYLQCM LASFRGDTLLQALDFLPLLMQTVEKAASQGTQVPTVTEGVAAALL LSKLSVADAQAEAKLSGFWQLVVDEKRQTFTSEKFLLLASEDALC TVLRLTERLFLDHPHRLTNSKVQQYYRVLVAVLLSRTWHVRRQAQ QTVRKLLSSLGGVKLANGLLDELKTVLNSHKVLPLEALVTDAGEV TEMGKTYVPPRVLQEALCVISGVPGLKGDIPSTEQLAQEMLIISH HPSLVAVQSGLWPALLTRMKIDPDAFITRHLDQIIPRITTQSPLN QSSMNAMGSLSVLSPDRVLPQLISTITASVQNPALCLVTREEFSI MQTPAGELFDKSIIQSAQQDSIKKANMKRENKAYSFKEQIIEMEL KEEIKKKKGIKEEVQLTSKQKEMLQAQMDKEAQIRRRLQELDGEL EAALGLLDAIMARNPCGLIQYIPVLVDAFLPLLKSPLAAPRVKGP FLSLAACVMPPRLKTLGTLVSHVTLRLLKPECALDKSWCQEELPV AVRRAVSLLHTHTIPSRVGKGEPDAAPLSAPAFSLVFPMLKMVLT EMPYHSEEEEEQMAQILQILTVHAQLRASPDTPPERVDENGPELL PRVAMLRLLTWVIGIGSPRLQVLASDTLTALCASSSGEDGCAFAE QEEVDVLLAALQSPCASVRETALRGLMELRLVLPSPDTDEKSGLS LLRRLWVIKFDKEDEIRKLAERLWSTMGLDLQSDLCSLLIDDVIY HEAAVRQAGAEALSQAVARYQRQAAEVMGRLMEIYQEKLYRPPPV LDALGRVISESPPDQWEARCGLALALNKLSQYLDSSQVKPLFQFF VPDALNDRNPDVRKCMLDAALATLNAHGKENVNSLLPVFEEFLKD APNDASYDAVRQSVVVLMGSLAKHLDKSDPKVKPIVAKLIAALST PSQQVQESVASCLPPLVPAVKEDAGGMIQRLMQQLLESDKYAERK GAAYGLAGLVKGLGILSLKQQEMMAALTDAIQDKKNFRRREGALF AFEMLCTMLGKLFEPYVVHVLPHLLLCFGDGNQYVREAADDCAKA VMSNLSAHGVKLVLPSLLAALEEESWRTKAGSVELLGAMAYCAPK QLSSCLPNIVPKLTEVLTDSHVKVQKAGGQALRQIGSVIRNPEIL AIAPVLLDALTDPSRKTQKCLQTLLDDTKFVHFIDAPSLALIMPIV QRAFQDRSTDTRKMAAQIIGNMYSLTDQKDLAPYLPSVTPGLKAS LLDPVPEVRTVSAKALGAMVKGMGESCFEDLLPWLMETLTYEQSS VDRSGAAQGLAEVMAGLGVEKLEKLMPEIVATASKVDIAPHVRDG YIMMFNYLPITFGDKFTPYVGPIIPCILKALADENEFVRDTALRA GQRVISMYAETAIALLLPQLEQGLFDDLWRIRFSSVQLLGDLLFH ISGVTGKMTTETASEDDNFGTAQSNKAIITALGVDRRNRVLAGLY MGRSDTQLVVRQASLHVWKIVVSNTPRTLREILPTLFGLLLGFLA STCADKRTIAARTLGDLVRKLGEKILPEIIPILEEGLRSQKSDER QGVCIGLSEIMKSTSRDAVLFFSESLVPTARKALCDPLEEVREAA AKTFEQLHSTIGHQALEDILPFLLKQLDDEEVSEFALDGLKQVMA VKSRVVLPYLVPKLTTPPVNTRVLAFLSSVAGDALTRHLGVILPA VMLALKEKLGTPDEQLEMANCQAVILSVEDDTGHRIIIEDLLEAT RSPEVGMRQAAAIILNMYCSRSKADYSSHLRSLVSGLIRLFNDSS PVVLEESWDALNAITKKLDAGNQLALIEELHKEIRFIGNECKGEH VPGFCLPKRGVTSILPVLREGVLTGSPEQKEEAAKGLGLVIRLTS ADALRPSVVSITGPLIRILGDRFNWTVKAALLETLSLLLGKVGIA LKPFLPQLQTTFTKALQDSNRGVRLKAADALGKLISIHVKVDPLF TELLNGIRAVEDPGIRDTMLQALRFVIQGAGSKVDAAIRKNLVSL LLSMLGHDEDNTRISTAGCLGELCAFLTDEELNTVLQQCLLADVS | 15 |

TABLE 1-continued

Description of the Sequences

| Description | Sequences | SEQ ID NO |
|---|---|---|
| | GIDWMVRHGRSLALSVAVNVAPSRLCAGRYSNEVQDMILSNAVAD RIPIAMSGIRGMGFLMKYHIETGSGQLPPRLSSLLIKCLQNPCSD IRLVAEKMIWWANKEPRPPLEPQTIKPILKALLDNTKDKNTVVRA YSDQAIVNLLKMRRGEELLQSLSKILDVASLEALNECSRRSLRKL ACQADSVEQVDDTILT | |
| Mouse perilipin 4 (UniProtKB-O88492) | MSASGDGTRVPPKSKGKTLSSFFGSLPGFSSARNLVSHTHSSTST KDLQTATDPSGTPAPSSKVSTNSQMAGDAAGLLQPSEQTAGDKDM GSFSVTSSEDAFSGVFGIMDAAKGMVQGGLGATQSALVGTKEAVS GGVMGAVGVAKGLVKGGLDTSKNVLTNTKDTVTTGVMGAANMAKG TVQTGLDTTKSVVMGTKDTVATGLAGAVNVAKGTIQGGLDTTKSV VMGTKDTVTTGLTGAVNVAKGVVQGGLDTTKSVVMGTKDTVTTGL TGAMNVAKGTAQMGIDTSKTVLTGTKDTVCAGATGAINVAKGAAQ GGLDTTKSVLIGTKDTVTTGLTGAVNVAKGAVQGGLDTTKSVVMG TKDTVTTGLTGAMNVAKGTAQMGLGTSKTVLTGTKDTVCAGLTGA INVAKGAAQGGLDTTKSVLMGTKDTVTTGLTGAVNVAKGTIQGGL DTTKSVVMGTKDTVTTGLTGAVNVAKGTIQGGLDTTKSVVMGTKD TVITGLTGAVNVAKGAAQGGLDTTKSVVMGTKDTVITGLTGAMNV AKGTAQMGLGTSKTVLTGTKDTVCAGLTGAINVAKGAAQGGLDTT KSVLMGTKDTVITGLIGAVNVAKGTIQGGLDTTKSVVMGTKDTVT TGLTGAVNVAKGAVQGGLDTTKSVVMGTKDTVTTGLTGALNVAKG TAQMGIDTSKTVLIGTKDTVCAGATGAINMAKGAAQGGLDTTKSV LMGTKDTVTTGLTGAINVAKGSAQGGLDTTKSVLIGTKDTVTTGL TGALNVAKGTVQTGLDTSQRVLTGTKDNVYAGVTGAVNVAKGTIQ GGLDTTKSVVMGTKDTVTTGLTGAVNVAKGAVQGGLDTTKSVVMG TKDTVTTGLTGAMNVAKGTAQMGIDTSKTVLTGTKDTVCAGLTGA INVAKGATQGGLDTTKSVLMGTKDTVTTGLTGAINVAKGAAQGGL DTTKSVLLGTKDTVTTGLTGAANVAKETVQMGLDTSKNILMDTKD SICAGATGAITVVKGAAQGGLDTSNAALTGTMDTAKGTVQTSLDT SKHMLIGMKDTVCAGVTSAMNMAKGIHKNTDTTRDTQSSVLAHSG NVATNAIHTGVHTVPSSLSGSHSIICHEPSIYRATNHGVGQAILT STESLCCETSSFSDKYGLGHVTEPRADTKTLVSGMASSACAATRS VEECGQLAATGFAALPDELKGLGDIFQPMTTEEQAQLAVSESGPR VLSADRGSYYIRLGDLAPSFRQRAFEHALSHIQHNQFQARAALAQ LQEAFQMTDMTMEAACGKLCSDQSLNTMVEAVGSHEMRASVAQDR LCTLAHQLHAAYSSLVTSLQGLPEVQQQAGQARHSLCKLYGLVSS EAGSELQTEQLAQSSAGVVEAWQGLEVLLEKLQQNPPLSWLVGPF TSMPCGQL | 16 |
| Mouse mediator of RNA polymerase II transcription subunit 11 (UniProtKB-Q6ID77) | MDPQTQNTSLQRLQNVENRVVKVLELAGGVMEELASPSGPKKEFV NSHCREFMQSMKDIQVTLREEIKSACEYRPFEKCDYNARIANEIC FQKLEYVLTQLEDLKQTADRYPSSD | 17 |
| Mouse protein-glutamine gamma-glutamyl-transferase 6 (UniProtKB-Q14CG3) | MVNSNNDRGVVQGQWQGKYGGGTNPLNWRGSVAILQKWFKGRYKP VKYGQCWVFAGVMCTVLRCLGIATRVVSNFNSAHDTDGNLSVDKY VDSYGRTLEDLTEDSMWNFHVWNESWFARQDLGPSYDGWQVLDAT PQEESEGMFRCGPASVTAIREGDVHLAHDGPFVFAEVNADYITWL WHEDKRRERVYSDTKKIGRCISTKAVGSDSRVDITGLYKYPEGSR KERQVYSKAVKKLLSVEAWGRRRRIRRASVRGVWRDDLLEPVTKP SITGKFKVLEPPVLGQDLKLALCLTNLTARAQRVRVNVSGATILY TRKPVAEILRESHTVKLGPLEEKKIPVTISYSQYKGDLTEDKKIL LAAMCLVSKGEKLLVEKDITLEDFITIKVLGPAVVGVTVTVEVLV INPLSESVKDCVLMVEGSGLLQGQLSIEVPSLQPQEKALIQFNIT PSKSGPRQLQVDLVSSQFPDIKGFVIIHVATAK | 18 |
| Mouse zinc finger BED domain-containing protein 3 (UniProtKB-Q9D0L1) | MKSKKPLKITMEDSRRLNDPAEQGGLCPAPVGPSYSEAWGYFHLD PAQPRHRMMSAWATCRLCGLQVGGLPNFQMWTRALCQHLSDVHLP ELKKSAAPSSPTTMPCPPPPSPTMAAEGDWARLLEQMGELAMRGS QRELELERREAALMQAELELERKRQALKQEAQSVEQERHQLQVER EALSKWIKKQSPGAQVPEPPSPLPLLPKEDPDIHDNNSDNDMVTK VLL | 19 |

TABLE 1-continued

Description of the Sequences

| Description | Sequences | SEQ ID NO |
|---|---|---|
| Mouse metabotropic receptor 2 (UniProtKB-Q14BI2) | MESLLRFLALLLLRGAVAEGPAKKVLTLEGDLVLGGLFPVHQKGG PAEECGPVNEHRGIQRLEAMLFALDRINRDPHLLPGVRLGAHILD SCSKDTHALEQALDFVRASLSRGADGSRHICPDGSYATLSDAPTA ITGVIGGSYSDVSIQVANLLRLFQIPQISYASTSAKLSDKSRYDY FARTVPPDFFQAKAMAEILRFFNWTYVSTVASEGDYGETGIEAFE LEARARNICVATSEKVGRAMSRAAFEGVVRALLQKPSARVAVLFT RSEDARELLAATQRLNASFTWVASDGWGALESVVAGSERAAEGAI TIELASYPISDFASYFQNLDPWNNSRNPWFREFWEERFRCSFRQR DCAAHSLRAVPFEQESKIMFVVNAVYAMAHALHNMHRALCPNTTR LCDAMRPVNGRRLYKDFVLNVKFDAPFRPADTDDEVRFDRFGDGI GRYNIFTYLRAGNGRYRYQKVGYWAEGLTLDTSIIPWASPSAGTL PASRCSEPCLQNEVKSVQPGEVCCWLCIPCQPYEYRLDEFTCADC GLGYWPNASLTGCFELPQEYIRWGDAWAVGPVTIACLGALATLFV LGVFVRHNATPVVKASGRELCYILLGGVFLCYCMTFIFIAKPSTA VCTLRRLGLGTAFSVCYSALLTKTNRIARIFGGAREGAQRPRFIS PASQVAICLALISGQLLIVAAWLVVEAPGIGKETAPERREVVTLR CNHRDASMLGSLAYNVLLIALCTLYAFKTRKCPENFNEAKFIGFT MYTTCIIWLAFLPIFYVTSSDYRVQTTTMCVSVSLSGSVVLGCLF APKLHIILFQPQKNVVSHRAPTSRFGSAAPRASANLGQGSGSQLV PTVCNGREVVDSTTSSL | 20 |
| Mouse Gm3604 protein (Gm3604 gene product) (UniProtKB-D3YUB7) | NAVTYEDVHVNFTQEEWALLDPSQKTLYKDVMLETFRNLNAIGFN WEAQNIEEYCQSSRRHRRCERSQSAEKPSEYTQRDKAFALHDHSH AQRHERVHTEKIPSEVIHCVEDFLPYTSLQVHKRTQTGQKPYECN QCGKGFVMPSCLKRHERFHTGEKPYKCNQCDKAFSQYNNLQTHRR THTGEKPYKCNQCDKAFSQHSTLQTHRRTHTGEKPFKCNQCDKAF SEKCSLQTHRRTHTGEKPYKCNQCDKAFSQYSHLHIHRRTHTGEK PLKCNECDETFSNHSNLQTHRRIHTGEKPYKCNQCDKAFSQHSTL QNHRRTHTGEKPFKCNQCDKAFSRHSTLQTHRRTHTGEKPFKCNQ CDKAFSQYSHLHIHRRTHTGEKPFKCNQCNKAFSQYSHLHIHRRT HTGEKPYKCNQCDKTFSNHSTLQTHRRTHTGEKPYKCNQCDKAFS RHSTLQTHRRTHTGEKPFKCNQCDKAFSQKCSLQKHIRIHTGEKL YKCNECDKAFSQHSTLQTHRRTHTGEKPFKFNECDEGFSHHYNLQ IHERRHTREKPYKCIQCV | 21 |
| Mouse olfactory receptor (Olfr911-ps1 gene product) (UniProtKB-A0A140T8K0) | MGLENGSLVTEFILLGLTNDPDLQLPLFLLFLLIYTTTAVGNLAL ITLIALNSHLHTPMYFFLLNLSCIDLCYSSVITPKMLMNFLVRKN IISYMGCMTQLYFFCFFAICECCVLTSMAYDRYVAICNPLLYNIT MSPKVCSYLMLGSYIMGFSGAMIHTGCILRLTFCDRNIINHYFCD LFPLLQLSCTSTYANEIEILIVGGKDIIVPSVIIFTSYGFILSNI LQMRSTAGMSKAFSTCSSHILAVSLFFGSCAFMYLQPSSPGSMDQ GKVSSVFYTIVVPMMNPLIYSFRNKDVKIALRKIFGKRRFS | 22 |

DESCRIPTION OF THE EMBODIMENTS

I. Definitions

In addition to definitions included in this sub-section, further definitions of terms are interspersed throughout the text.

In this invention, "a" or "an" means "at least one" or "one or more," etc., unless clearly indicated otherwise by context. The term "or" means "and/or" unless stated otherwise. In the case of a multiple-dependent claim, however, use of the term "or" refers back to more than one preceding claim in the alternative only.

"Autoimmune" or "autoimmune attack," as used herein, refers to an attack by the subject's immune system against cells that are part of the subject. As such, an autoimmune disease is an abnormal immune response to a normal body part. In the case of type 1 diabetes, the autoimmune attack is predominantly against the beta cells of the pancreas that normally secrete insulin in a glucose-dependent manner.

As used herein, "beta-like cell" refers to any cell that secretes insulin in response to glucose. Thus, a pancreatic beta cell is a "beta-like cell." Beta-like cells may be derived from cells that do not normally produce insulin in response to glucose. For example, a beta-like cell may be a stem cell that is induced to differentiate into a "beta-like cell" that produces insulin in a glucose-responsive manner. (see F W Pagliuca et al., Cell 159:428-439 (2014); E Kroon et al., Nature Biotech 26(4):443-452 (2008); and A Rezania et al., Nature Biotech 32(11): 1121-1133 (2014). Likewise, a "beta-like cell" may also be a pancreatic exocrine cell (see Q Zhou et al., Nature 455:627-633 (2008)), pancreatic alpha cell (see Li et al, Cell 168:86-100 (2017), or gut cell (see Ariyachet C et al., Cell Stem Cell 18(3):410-21 (2016)) that is induced to produce insulin in response to glucose. The term "beta-like cells" also includes cells that become glucose responsive insulin secretors after transplantation into a subject.

The term "genetically modified" or to "genetically modify," as used herein, describes any method that reduces the expression or function of one or more protein in a cell from the baseline or unmodified state. Examples of means to genetically modify cells include decreasing expression of a protein, inhibiting expression of a protein, silencing expression of a protein, eliminating expression of a protein, reducing function of a protein, inhibiting proper confirmation of a protein, or any other means to change expression or function of a protein.

The term "inhibit expression of a gene" or "inhibiting expression of a gene," as used herein refers to causing a decrease in expression of a protein product of the gene.

The term "silence a gene" or "silencing a gene," as used herein refers to causing a lack of expression of the protein product of the gene.

The term "treatment," as used herein, covers any administration or application of a therapeutic for disease in a subject, and includes inhibiting the disease, arresting its development, relieving one or more symptoms of the disease, or preventing reoccurrence of one or more symptoms of the disease. For example, treatment of diabetes type 1 subjects may comprise alleviating hyperglycemia as compared to a time point prior to administration or reducing the subject's need for exogenous insulin administration.

II. Compositions

In some embodiments, compositions are provided comprising modified beta-like cells. In general, the modifications allow the beta-like cell to survive when implanted into an animal model of type 1 diabetes, or when implanted into a human with type 1 diabetes. The modifications generally allow the beta-like cell to survive autoimmune attack.

In some embodiments, the genetic modification comprises any modification that results in a reduced expression of the following proteins: menin (SEQ ID No: 1), transcription factor HIVEP2 (SEQ ID No: 2), renalase (SEQ ID No: 3), lengsin (SEQ ID No: 4), eIF-2-alpha kinase activator GCN1 (SEQ ID No: 5), perilipin-4 (SEQ ID No: 6), mediator of RNA polymerase II transcription subunit 11 (SEQ ID No: 7), protein-glutamine gamma-glutamyltransferase 6 (SEQ ID No: 8), zinc finger BED domain-containing protein 3 (SEQ ID No: 9), and metabotropic glutamate receptor 2 (SEQ ID No: 10).

A. Types of Beta Cells to be Genetically Modified

1. Beta Cells Themselves

Beta cells of pancreas are the cells that normally can secrete insulin. These beta cells of the pancreas are located in pancreatic islets, also known as the islets of Langerhans.

In some embodiments, the genetically-modified beta-like cell is a beta cell of the pancreas. In some embodiments, the genetically-modified beta-like cell is a beta cell that has been genetically modified ex vivo, and reintroduced into the same or different individual from which it was isolated. When introduced into the same subject from which it was isolated it is an autologous genetically-modified beta-like cell. When introduced into a different subject from which it was isolated it is a heterologous genetically-modified beta-like cell.

2. Cells Induced to Have a Phenotype of a Beta-Like Cell

In some embodiments, the beta-like cell is a cell that does not normally produce insulin in response to glucose, but is induced or designed to have a phenotype of a beta-like cell, i.e., induced or designed to produce insulin in response to glucose. Beta-like cells include "designer beta cells," which have been described as using synthetic pathways to produce insulin (see M Xie et al., *Science* 354(6317):1296-1301 (2016)).

a) Stem Cells

Any stem cell capable of differentiating into a beta-like cell may be genetically modified according to the invention. In some embodiments, the beta-like cell may be differentiated from a hematopoietic stem cell, bone marrow stromal stem cell, or mesenchymal stem cell.

Beta-like cells capable of secreting insulin in response to glucose can be generated from pluripotent stem cells (PSCs) (see FW Pagliuca et al., *Cell* 159:428-439 (2014)) or embryonic stem cells (ESCs) (see E Kroon et al., *Nature Biotech* 26(4):443-452 (2008) and A Rezania et al., *Nature Biotech* 32(11): 1121-1133 (2014)).

In some embodiments, the stem cell may be an embryonic stem cell. In some embodiments, the embryonic stem cell is taken from a blastocyst. In some embodiments, the embryonic stem cell may be derived from an embryo fertilized in vitro and donated. In some embodiments, the embryonic stem cell undergoes directed differentiation.

In some embodiments, the stem cell may be an adult stem cell. An adult stem cells may also be referred to as a "somatic" stem cell. In some embodiments, the adult stem cell is an undifferentiated cell found among differentiated cells in a tissue or organ.

In some embodiments, the stem cell is an induced pluripotent stem cell (iPSC).

In some embodiments, the stem cells may be from bone marrow, adipose tissue, or blood. In some embodiments, the cells may be from umbilical cord blood.

In some embodiments, stem cells undergo directed differentiation into beta-like cells. In some embodiments, the directed differentiation is based upon treatment of stem cells with modulators. In some embodiments, the directed differentiation is based on culture conditions.

In some embodiments, beta-like cells are generated from human PSCs (hPSCs) in vitro. In some embodiments, beta-like cells are generated from hPSCs using directed differentiation. In some embodiments, beta-like cells are generated from hPSCs using a multi-step protocol. In some embodiments, beta-like cells are generated from hPSCs using sequential modulation of multiple signaling pathways. In some embodiments, beta-like cells are generated from hPSCs using a three-dimensional cell culture system.

In some embodiments, beta-like cells are generated from human ESCs (hESCs) in vitro. In some embodiments, beta-like cells are generated from hESCs using directed differentiation. In some embodiments, beta-like cells are generated from hPSCs using a multi-step protocol. In some embodiments, beta-like cells are generated from hESCs using sequential modulation of multiple signaling pathways. In some embodiments, beta-like cells are generated from hESCs using a planar cell culture and air-liquid interface at different stages of differentiation.

b) Non-Stem Cells

In some embodiments, beta-like cells are produced from non-stem cells. In some embodiments, beta-like cells are produced from differentiated non-beta cells. In some embodiments, beta-like cells are produced from reprogramming or transdifferentiation of differentiated non-beta cells.

In some embodiments, the beta-like cell is a reprogrammed non-beta cell. In some embodiments, the beta-like cell is a transdifferentiated non-beta cell.

As all cells of the body contain the full genome, any type of cell could be induced into a beta-like cell based on principles of reprogramming and transdifferentiation. Thus, the invention is not limited by the original phenotype of the beta-like cell.

Pancreatic exocrine cells can be reprogrammed into beta-like cells that secrete insulin (see Q Zhou et al., *Nature* 455:627-633 (2008)).

In some embodiments, a pancreatic exocrine cell is reprogrammed into a beta-like cell. In some embodiments, the pancreatic exocrine cell is differentiated into a beta-like cell based on re-expression of transcription factors. In some embodiments, these transcription factors are Ngn3, Pdx1, and Mafa.

Pancreatic alpha cells can be transdifferentiated into beta-like cells. The anti-malarial drug, artemisin, inhibits the master regulatory transcription factor Arx (Aristaless related homeobox) and enhances gamma-amino butyric acid (GABA) receptor signaling, leading to impaired pancreatic alpha cell identity and transdifferentiation of alpha cells into a beta-like cell phenotype (see Li et al, *Cell* 168:86-100 (2017) and Ben-Othman N et al., *Cell* 168(1-2):73-85 (2017)).

In some embodiments, the beta-like cell is a transdifferentiated cell. In some embodiments, an alpha cell is transdifferentiated into a beta-like cell. In some embodiments, the transdifferentiation into a beta-like cell is due to inhibition of Arx. In some embodiments, the transdifferentiation into a beta-like cell is due to enhancement of GABA receptor signaling.

Stomach tissue can be reprogrammed into beta-like cells (see Ariyachet C et al., *Cell Stem Cell* 18(3):410-21 (2016)). In some embodiments, a gut or stomach cell is reprogrammed into a beta-like cell. In some embodiments, the reprogramming is based on expression of beta cell reprogramming factors. In some embodiments, cells of the antral stomach are reprogrammed into beta-like cells. In some embodiments, these cells of the antral stomach are antral endocrine cells. In some embodiments, reprogrammed antral endocrine cells can be assembled into a mini-organ of beta-like cells.

B. Types of Genetic Modification to the Beta-Like Cells

In some embodiments, genetic modification inhibits or reduces expression of a protein, thus leading to improved survival and/or proliferation of transplanted beta-like cells. In some embodiments, genetic modification silences expression of a gene, thus leading to improved survival and/or proliferation of transplanted beta-like cells.

In some embodiments, silencing of a gene or inhibiting expression of a protein is due to editing that removes all or a portion of the target gene, or all or a portion of a region of DNA that regulates the target gene. In some embodiments, editing that removes a portion of the target gene, or the DNA controlling its regulation, results in silencing the gene or inhibiting expression of the gene product.

A variety of methods of gene editing would be known to one skilled in the art, and this invention is not limited by the particular mechanism used for editing.

a) CRISPR/Cas9

The clustered regularly interspaced short palindromic repeats (CRISPR)/Cas9 system is a prokaryotic immune system that confers resistance to foreign gene elements.

In some embodiments, the CRISPR/Cas9 system is used to genetically modify beta-like cells. In some embodiments, a synthetic guide RNA (gRNA) is used to direct the CRISPR/Cas9 system to a specific sequence within the genome of the beta-like cell to perform gene editing.

b) Zinc-Finger Nucleases

Zinc-finger nucleases are artificial restriction enzymes generated by fusing a zinc finger DNA-binding domain to a DNA-cleavage domain.

In some embodiments, a zinc-finger nuclease is used to genetically modify beta-like cells. In some embodiments, the zinc-finger nuclease targets to a specific sequence within the genome of the beta-like cell to perform gene editing.

c) Transcription Activator-Like Effector Nuclease (TALEN)

Transcription Activator-Like Effector Nucleases (TALEN) are Restriction enzymes engineered to cut specific sequences of DNA. TALEN are generated by fusion of a TAL effector DNA-binding domain to a nuclease.

In some embodiments, a TALEN is used to genetically modify beta-like cells. In some embodiments, the TALEN targets to a specific sequence within the genome of the beta-like cell to perform gene editing.

d) Meganuclease

Meganucleases are endodeoxyribonucleases with a large recognition site that often will only occur rarely within a genome. Modified meganucleases can have a targeted recognition site.

In some embodiments, a meganuclease is used to genetically modify beta-like cells. In some embodiments, the meganuclease targets to a specific sequence within the genome of the beta-like cell to perform gene editing.

e) Group One Intron Encoded Endonuclease (GIIEE)

In some embodiments, a GIIEE is used to genetically modify beta-like cells.

In some embodiments, the meganuclease or GIIEE is I-SceI, I-Cre, I-AniI, I-CeuI, I-ChuI, I-CpaI, I-CpaII, I-DmoI, H-DreI, I-HmuI, I-HmuII, I-LlaI, I-MsoI, PI-PfuI, PI-PkoII, I-PorI, I-PpoI, PI-PspI, I-ScaI, PI-SceI, I-SceII, I-SecIII, I-SceIV, I-SceV, I-SceVI, I-SceVII, I-Ssp6803I, I-TevI, I-TevII, I-TevIII, PI-TliI, PI-TliII, I-Tsp061I, or I-VdI141I.

In some embodiments, gene modifications silence a gene or inhibit expression of a gene that promotes beta-like cell death. In some embodiments, gene modifications silence a gene or inhibit expression of a gene, thereby promoting beta-like cell survival or proliferation.

In some embodiments, the gene encoding human menin (SEQ ID No: 1), transcription factor HIVEP2 (SEQ ID No: 2), renalase (SEQ ID No: 3), lengsin (SEQ ID No: 4), eIF-2-alpha kinase activator GCN1 (SEQ ID No: 5), perilipin-4 (SEQ ID No: 6), mediator of RNA polymerase II transcription subunit 11 (SEQ ID No: 7), protein-glutamine gamma-glutamyltransferase 6 (SEQ ID No: 8), zinc finger BED domain-containing protein 3 (SEQ ID No: 9), or metabotropic glutamate receptor 2 (SEQ ID No: 10) is silenced or its expression is inhibited. In some embodiments, more than one gene encoding these proteins is inhibited or silenced. The term "gene encoding" includes any DNA encoding the amino acid or functional equivalents thereof. In some embodiments, the functional equivalent is a mutated or variated protein, wherein the protein has same or similar function. The term "gene encoding" further includes all isoforms, splice variants, and mature and immature forms of the protein. In some embodiments, inhibiting or silencing a protein includes inhibiting expression, function, structure, or any other property of a protein needed to perform its normal role in the body.

In some embodiments, a genetic modification is introduced into an exon, intron, promoter, or other region of the Men 1 (Gene ID No: 4221), HIVEP2 (Gene ID No: 3097), RNLS (Gene ID No: 55328), LGSN (Gene ID No: 51557), GCN1 (Gene ID No: 10985), PLIN4 (Gene ID No: 729359), MED11 (Gene ID No: 400569), TGM6 (Gene ID No: 343641), ZBED3 (Gene ID No: 84327), or GRM2 (Gene ID No: 2912), and the gene is silenced or its expression is inhibited by introduction of the genetic modification. In some embodiments, more than one of these genes is silenced or its expression is inhibited. In some embodiments, the genetic modification introduced is a deletion, substitution, or insertion of one or more nucleotides.

C. Non-Cellular Agents to Modify Function of a Protein Promoting Beta-Like Cell Death The function of human menin (SEQ ID No: 1), transcription factor HIVEP2 (SEQ ID No: 2), renalase (SEQ ID No: 3), lengsin (SEQ ID No: 4), eIF-2-alpha kinase activator GCN1 (SEQ ID No: 5), perilipin-4 (SEQ ID No: 6), mediator of RNA polymerase II transcription subunit 11 (SEQ ID No: 7), protein-glutamine gamma-glutamyltransferase 6 (SEQ ID No: 8), zinc finger BED domain-containing protein 3 (SEQ ID No: 9), or metabotropic glutamate receptor 2 (SEQ ID No: 10) can also be inhibited by post-translational means. Any means of post-translational modulation may be used, including inhibiting binding of ligand, inhibiting function of an enzyme protein, allosteric modulation, or increasing degradation of the protein.

In some embodiments, small molecules can be used to inhibit the function of human menin (SEQ ID No: 1), transcription factor HIVEP2 (SEQ ID No: 2), renalase (SEQ ID No: 3), lengsin (SEQ ID No: 4), eIF-2-alpha kinase activator GCN1 (SEQ ID No: 5), perilipin-4 (SEQ ID No: 6), mediator of RNA polymerase II transcription subunit 11 (SEQ ID No: 7), protein-glutamine gamma-glutamyltransferase 6 (SEQ ID No: 8), zinc finger BED domain-containing protein 3 (SEQ ID No: 9), or metabotropic glutamate receptor 2 (SEQ ID No: 10). In some embodiments, the function of the target protein is inhibited without an effect on the expression level of the protein.

Renalase (SEQ ID No: 3) and protein-glutamine gamma-glutamyltransferase 6 (SEQ ID No: 8) are enzymes. In some embodiments, enzyme inhibitors of renalase or protein-glutamine gamma-glutamyltransferase 6 inhibit the function of the enzymes. In some embodiments, inhibition of renalase or protein-glutamine gamma-glutamyltransferase 6 promotes survival and/or proliferation of beta-like cells.

Inhibitors of menin have been described (see Grembecka J et al., *Nature Chemical Biology* 8:277-284 (2012)). In some embodiments, an inhibitor of menin promotes survival and/or proliferation of beta-like cells.

Metabotropic glutamate receptor 2 (mGluR2) inhibitors or negative allosteric modulators have been described (see Podkowa K et al., *Psychopharmacology (Berl)* 233(15-16): 2901-14 (2016)). In some embodiments, an inhibitor or negative allosteric modulator of mGluR2 promotes survival and/or proliferation of beta-like cells. In some embodiments, LY341495 is the inhibitor or negative allosteric modulator of mGluR2. In some embodiments, (2S)-α-ethylglutamic acid (EGLU) is the inhibitor or negative allosteric modulator of mGluR2. In some embodiments, MGS-0039 is the inhibitor or negative allosteric modulator of mGluR2.

III. Methods of Treatment

In each embodiment of the invention, the subject treated is a mammal. In one embodiment, the mammal is a human, non-human primate, cow, horse, pig, sheep, goat, dog, cat, or rodent. In embodiment, the subject is a human subject.

Glucose levels in the blood are normally tightly regulated to maintain an appropriate source of energy for cells of the body. Dysregulation of blood sugar must be ameliorated to maintain health and longevity, and therapies that are fast acting are especially desired. Such fast acting therapies allow subjects to monitor blood glucose in real time and immediately self-medicate themselves to bring glucose levels within normal limits. Dosing with exogenous insulin is one example of a fast-acting glucose modulator that has allowed subjects with diabetes to maintain relatively normal lifestyles. Described herein is a non-insulin fast-acting compound that regulates blood glucose levels in real-time.

Insulin and glucagon are principal hormones that regulate blood glucose levels. In response to an increase in blood glucose, such as after a meal, insulin is released from beta cells of the pancreas. Insulin regulates the metabolism of carbohydrates and fats by promoting uptake of glucose from the blood into fat and skeletal muscle. Insulin also promotes fat storage and inhibits the release of glucose by the liver. Regulation of insulin levels is a primary means for the body to regulate glucose in the blood.

When glucose levels in the blood are decreased, insulin is no longer released and instead glucagon is released from the alpha cells of the pancreas. Glucagon causes the liver to convert stored glycogen into glucose and to release this glucose into the bloodstream. Thus, insulin and glucagon work in concert to regulate blood glucose levels.

In one embodiment, treatment of diabetes mellitus is to administer a composition to a subject to lower blood glucose.

Hyperglycemia refers to an increased level of glucose in the blood. Hyperglycemia can be associated with high levels of sugar in the urine, frequent urination, and increased thirst. Diabetes mellitus refers to a medical state of hyperglycemia.

The American Diabetes Association (ADA) suggests that fasting plasma glucose (FPG) levels of 100 mg/dL to 125 mg/dL or HbA1c levels of 5.7% to 6.4% may be considered hyperglycemia and may indicate that a subject is at high risk of developing diabetes mellitus (i.e. prediabetes, see ADA Guidelines 2015).

The ADA states that a diagnosis of diabetes mellitus may be made in a number of ways. A diagnosis of diabetes mellitus can be made in a subject displaying an HbA1c level of ≥6.5%, an FPG levels of ≥126 mg/dL, a 2-hour plasma glucose of ≥200 mg/dL during an OGTT, or a random plasma glucose level ≥200 mg/dL in a subject with classic symptoms of hyperglycemia.

Diabetes mellitus can be broken into Type 1 and Type 2. Type 1 diabetes mellitus (previously known as insulin-dependent diabetes or juvenile diabetes) is an autoimmune disease characterized by destruction of the insulin-producing beta cells of the pancreas. Classic symptoms of Type 1 diabetes mellitus are frequent urination, increased thirst, increased hunger, and weight loss. Subjects with Type 1 diabetes mellitus are dependent on administration of insulin for survival.

Type 2 diabetes mellitus is a metabolic disease characterized by a relative decrease in insulin levels and/or a phenotype of insulin resistance. Insulin resistance refers to when cells of the body no longer respond appropriately to insulin. The risk of Type 2 diabetes mellitus is increased in individuals who are obese or who have a sedentary lifestyle.

In the absence of regulation of glucose levels in subjects with diabetes, a range of serious complications may be seen. These include atherosclerosis, kidney disease, stroke, nerve damage, and blindness.

A method of treating diabetes mellitus comprising administering a composition is encompassed. In one embodiment, the method comprises lowering blood glucose levels in the diabetic subject to below about 200 mg/dL, 150 mg/dL, 100 mg/dL, or about 125 mg/dL.

In some embodiments, treatment of diabetes is increasing insulin levels in the subject after administering a composition.

In some embodiments, administering a composition causes a decrease in blood glucose levels such that levels are less than 200 mg/dL.

In some embodiments, the subject treated with a composition has Type 1 diabetes mellitus. In some embodiments, the diabetic subject treated has a relative decrease in insulin levels. In some embodiments, the subject treated has decreased beta cell mass. In some embodiments, the decrease in beta cell mass in a subject is due to an autoimmune disease.

In some embodiments, the subject treated has diabetes mellitus based on diagnosis criteria of the American Diabetes Association. In some embodiments, the subject with diabetes mellitus has an HbA1c level of ≥6.5%. In some embodiments, the subject with diabetes mellitus has an FPG levels of ≥126 mg/dL. In some embodiments, the subject with diabetes mellitus has a 2-hour plasma glucose of >200 mg/dL during an OGTT. In some embodiments, the subject with diabetes mellitus has a random plasma glucose level ≥200 mg/dL or 11.1 mmol/L. In some embodiments, the subject with diabetes mellitus has a random plasma glucose level ≥200 mg/dL or 11.1 mmol/L with classic symptoms of hyperglycemia.

A. Treatment with Genetically Modified Beta-Like Cells

In some embodiments, a method of treating type 1 diabetes, improving glucose tolerance, lowering blood glucose, and increasing insulin secretion in response to glucose is encompassed comprising administering a composition comprising a human beta-like cell, wherein the beta-like cell is capable of producing insulin in response to glucose, and wherein the beta-like cell is genetically modified to inhibit expression of one or more of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, the method comprises administering an agent that genetically modifies any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10) to an individual with type 1 diabetes is encompassed.

In some embodiments, the administering prevents the death of pancreatic islet cells.

In some embodiments, the administering lowers blood glucose in a subject.

In some embodiments, the administering increases insulin secretion in a subject.

In some embodiments, the administering treats type 1 diabetes in a subject.

In some embodiments, the subject is a mammal. In some embodiments, the mammal is a human.

In some embodiments, the subject has a blood sugar level higher than 11.1 mmol/liter or 200 mg/dl.

In some embodiments, genetically modified beta-like cells are administered via subcutaneous or intraperitoneal injection. In some embodiments, genetically modified beta-like cells are administered by portal vein infusion.

In some embodiments, genetically modified beta-like cells are transplanted. The genetically modified beta-like cells may be transplanted into any tissue that can support their survival/growth. In some embodiments, genetically modified beta-like cells are administered by transplant into the pancreas, liver, or fat pads. In some embodiments, genetically modified beta-like cells are transplanted via surgery, injection, or infusion.

In some embodiments, transplanted genetically modified beta-like cells can survive for 1, 2, 3, 4, 5, 6, 12, 18, 24, 36 months or indefinitely. In some embodiments, transplanted beta-like cells can survive for a year. In some embodiments, transplanted beta-like cells can survive for two years. In some embodiments, transplanted beta-like cells can survive for three years.

In some embodiments, proliferation of genetically modified beta-like cells over 1, 2, 3, 4, 5, 6, 12, 18, 24, or 36 months is improved compared to beta-like cells without the genetic modification.

B. Treatment with Agents Modulating Function of Protein Promoting Beta-Like Cell Death In some embodiments, a method of treating type 1 diabetes, improving glucose tolerance, lowering blood glucose, and increasing insulin secretion in response to glucose in a subject comprises administering a composition that inhibits the function of any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, a method of preventing the death of pancreatic islet cells comprises administering a composition that inhibits the function of any one of human menin (SEQ ID No: 1); transcription factor HIVEP2 (SEQ ID No: 2); renalase (SEQ ID No: 3); lengsin (SEQ ID No: 4); eIF-2-alpha kinase activator GCN1 (SEQ ID No: 5); perilipin-4 (SEQ ID No: 6); mediator of RNA polymerase II transcription subunit 11 (SEQ ID No: 7); protein-glutamine gamma-glutamyltransferase 6 (SEQ ID No: 8); zinc finger BED domain-containing protein 3 (SEQ ID No: 9); and metabotropic glutamate receptor 2 (SEQ ID No: 10).

In some embodiments, composition inhibits the function of metabotropic glutamate receptor 2 (SEQ ID No: 10). In some embodiments, the composition is LY341495, (2S)-α-ethylglutamic acid (EGLU), or MGS-0039.

C. Combination Treatment

In some embodiments, treatment further comprises an additional therapeutic agent.

In some embodiments, the further therapeutic agent is insulin. In some embodiments, the insulin is a rapid-acting, intermediate-acting, or long-acting insulin.

In some embodiments, the further therapeutic agent is an immunosuppressant or immunomodulatory agent. In some embodiments, the further therapeutic agent decreases the autoimmune response of the subject against beta-like cells.

In some embodiments, the further therapeutic agent is a glucagon-like peptide analog or agonist, dipeptidyl peptidase-4 inhibitor, amylin analog, biguanide, thiazolidinedione, sulfonylurea, meglitinide, alpha-glucosidase inhibitor, or sodium/glucose transporter 2 inhibitor.

EXAMPLES

Example 1

Whole-Genome Loss-of-Function (LOF) Screen

Unbiased whole-genome screening is a powerful approach to discover novel genes and signaling pathways that underlie disease. An LOF screen was performed in a mouse model using CRISPR/Cas9 genome editing technology (see Komor A C et al., *Cell* 168(1-2):20-36 (2016)).

This screen took advantage of the NOD mouse model of type 1 diabetes (see Pearson J A et al., *J. Autoimmun.* 66:76-88 (2016)). NOD mice develop type 1 diabetes due to autoimmune attack on beta cells of the pancreas.

In addition, the model used NIT-1 cells that are an immortalized beta cell line derived from NOD mice (see Hamaguchi K et al., *Diabetes* 40:842-9 (1991)). NIT-1 cells can be implanted into NOD mice without triggering alloreactivity, because of the cells' NOD origin. However, NIT-1 cells express all the beta cell antigens that are targeted by the immune system during autoimmunity and so are subject to immune killing in a NOD mouse.

A mouse model of induced attack on beta cells was developed using NIT-1 and NOD.scid mice. NOD.scid mice are NOD mice lacking a normal immune system. The scid mutation prevents the development of mature T and B lymphocytes, so that NOD.scid mice are protected from autoimmunity. Therefore, transplanted NIT-1 cells will not be targeted for immune killing by the NOD.scid immune system, and NIT-1 cells can be used as surrogate beta cells.

To elicit an experimentally regulated autoimmune attack on NIT-1 cells transplanted into the NOD.scid mice model, lymphocytes were transferred from diabetic NOD mice into NOD.scid animals. Autoreactive NOD T cells from the donor lymphocytes can start killing endogenous NOD.scid beta cells, as well as experimentally implanted NIT-1 cells.

This model system was tested as shown in FIG. 1. NIT-1 cells were infected with a lentiviral construct encoding a luciferase reporter at a multiplicity-of-infection (MOI) of 0.3-0.6. Transduced cells were then injected into NOD.scid mice subcutaneously, and some mice were also administered diabetogenic splenocytes (NOD splenocytes) on the same day. As shown in FIG. 1, non-invasive bioluminescence imaging of transplanted cells showed that the NOD splenocytes eliminated most of the implanted NIT-1 cells (~90%) within 15 days (compare the two animals on the right of the images for day 1 and day 15). In contrast, in the absence of autoreactive lymphocytes, NIT-1 cell mass expanded (see the two animals on the left of each image). These data indicate that the autoimmune attack on NIT-1 cells by injected NOD splenocytes can be used as a means of selective pressure on beta cell survival in the NOD.scid mice model.

A series of tools to run a CRISPR/Cas9 mediated whole-genome loss-of-function (LOF) screen were developed. The GeCKO V2 lentiviral pooled library was used that comprises guide RNAs (gRNAs) against every gene (Addgene, targeting >20,000 genes with 6 gRNAs/gene). This library was split into two sub-libraries (A and B), which each cover all targeted genes with 3 gRNAs/gene. These libraries cover the entire coding genome to potentially mutate every gene and also contain >1000 non-targeting gRNAs as internal negative controls. In the GeCKO library, Cas9 and gRNAs were incorporated into a single lentiviral vector to introduce these gene-targeting elements into beta cells by lentiviral infection. This CRISPR/Cas9 LOF system is superior to other previous LOF screening platforms because it is highly efficient and is likely to mutate both copies of a gene simultaneously.

A high-stringency LOF screen was done using a single mouse. In this model, $10^7$ GeCKO library-A infected NIT-1 cells (multiplicity of infection (MOI)=0.3) were injected subcutaneously, and $10^7$ diabetic NOD splenocytes were injected intravenously at the same time.

Figure 2:
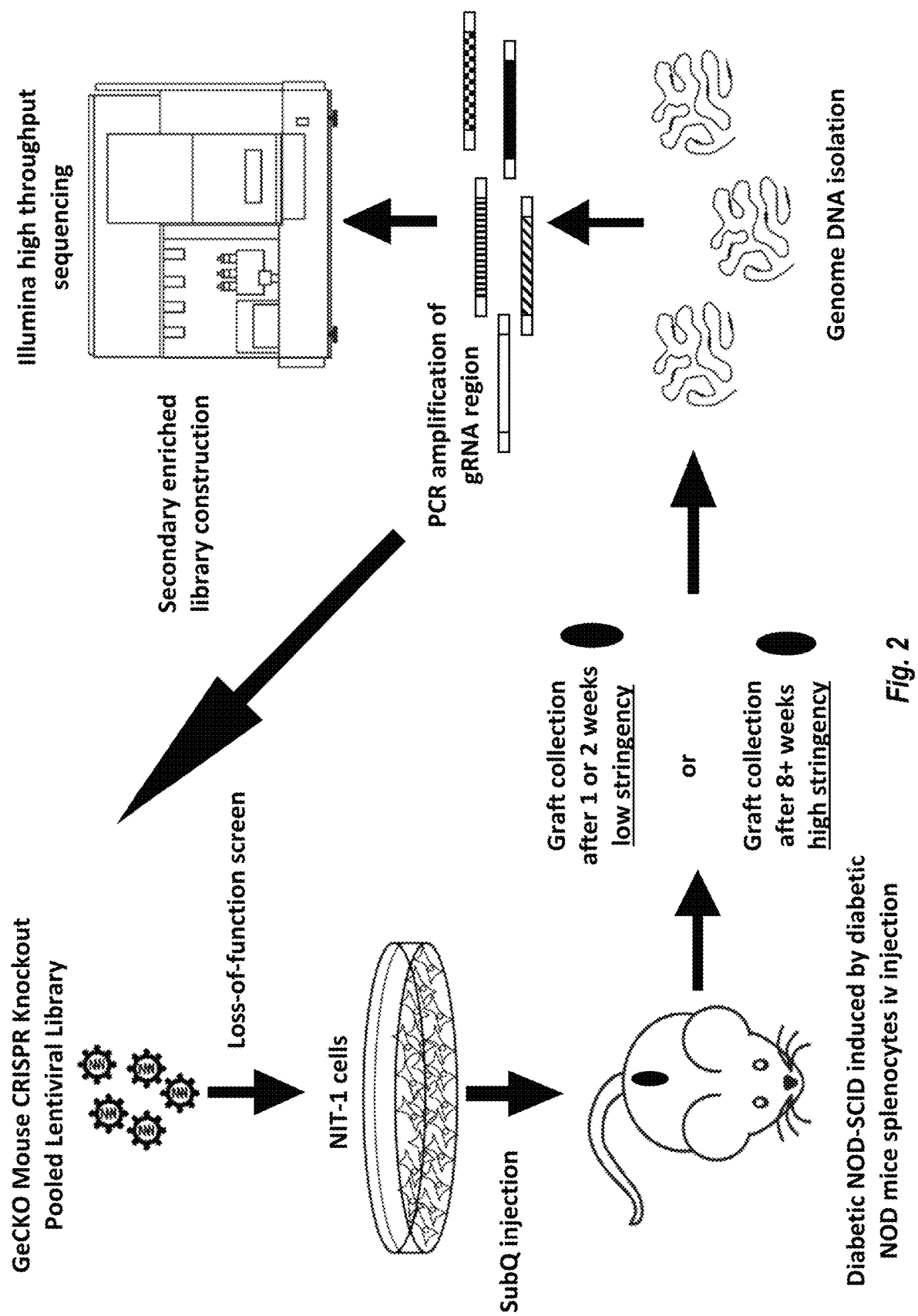
FIG. 2 shows schematic illustration of CRISPR/Cas9 based whole-genome loss-of-function (LOF) screen.

The workflow for the genome-wide LOF CRISPR-Cas9 screenings of beta cells is illustrated in FIG. 2.

Figure 3:
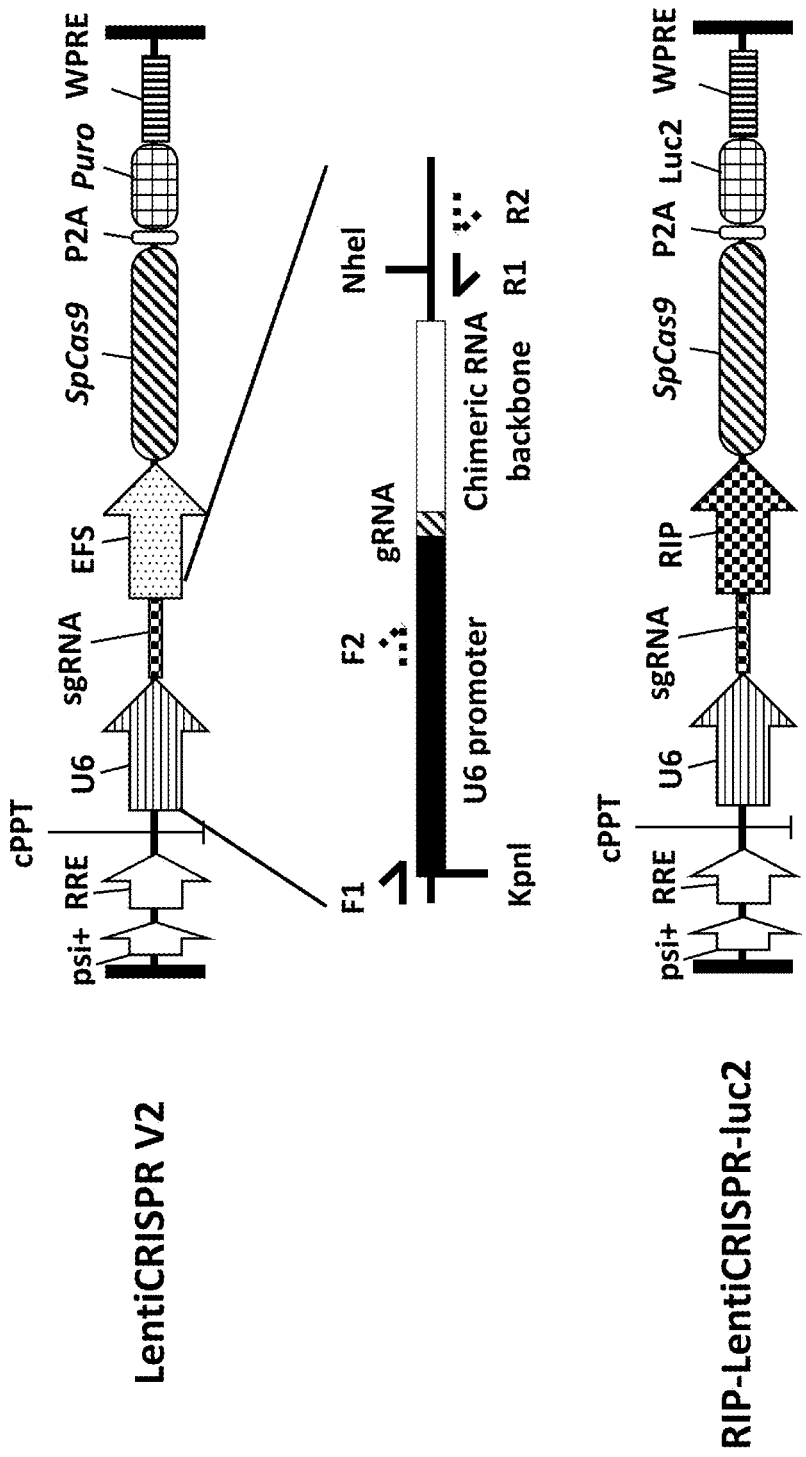
FIG. 3 shows lentiviral constructs used in GeCKO screen and subsequent confirmation in primary beta cells.

For sequencing, genomic DNA from explanted grafts was extracted with genome DNA midi prep kits, and the gRNA region was amplified from genomic DNA using established protocols. As illustrated in FIG. 3, the gRNA region from LentiCRISPR-V2 genomic insertion was amplified by PCR using the primers F2 and R1, barcoded and sequenced.

Figure 4:
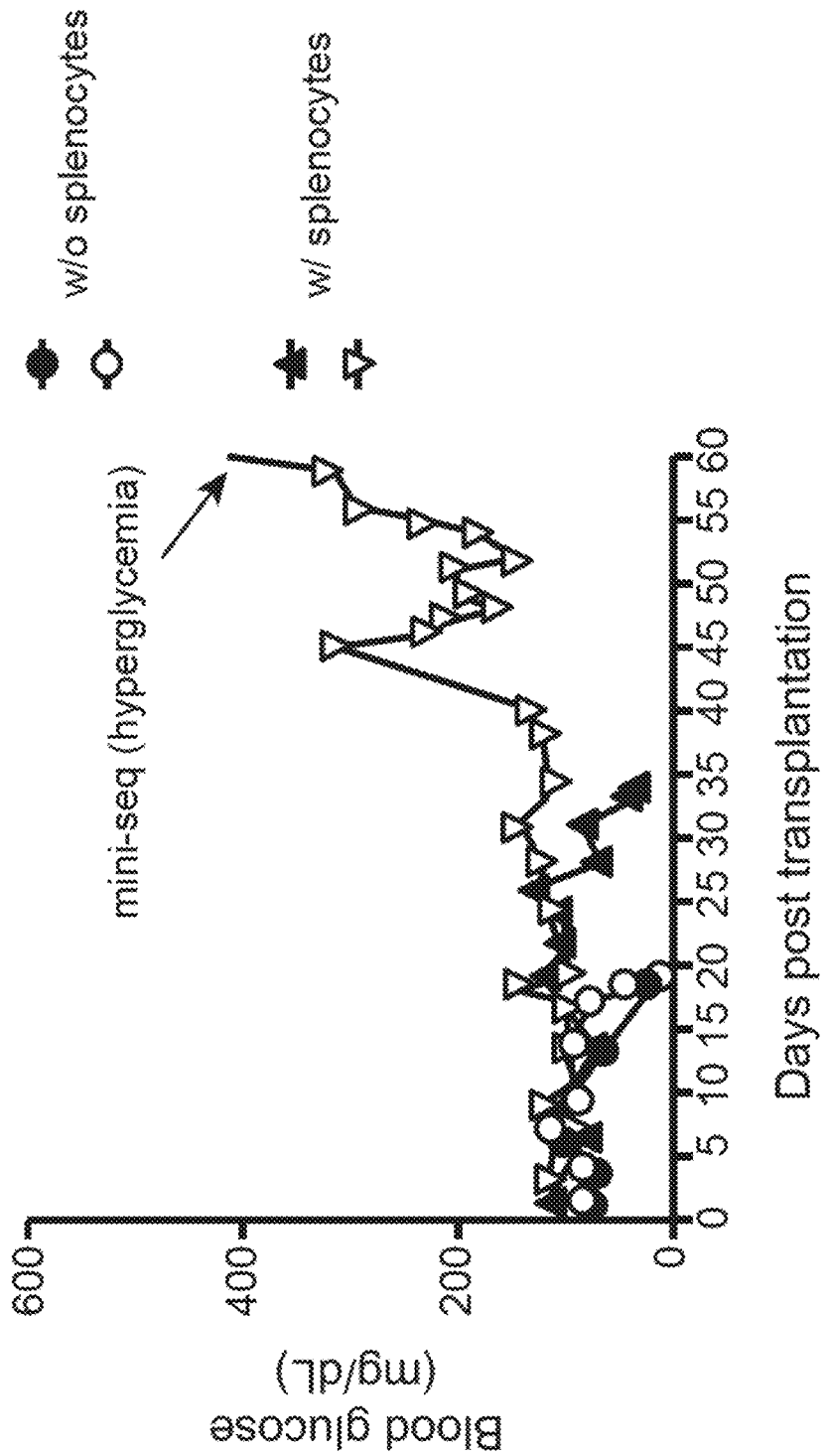
FIG. 4 shows blood glucose levels over 60 days in the LOF screen. The arrow shows blood glucose levels in the NOD.scid mice receiving transplanted NIT-1 cells transduced and splenocytes at the time when samples were taken for sequencing.

Selection pressure (i.e., autoimmune attack) on transplanted NIT-1 cells was maximized by waiting until NOD-.scid mice had become severely hyperglycemic (~60 days, marked by the arrow) as shown in FIG. 4. Even after the blood glucose of one recipient NOD.scid mouse had reached approximately 500 mg/dL, approximately 50,000 cells from the remaining graft could be isolated. gRNAs were amplified from the genome DNA of the graft and surveyed by mini-seq (low-depth sequencing).

Since the GeCKO library (A library) only contain approximately 60,000 unique gRNAs, $10^6$-$10^7$ sequencing reads was sufficient to cover the whole library and to achieve statistical significance. Typically, one high throughput sequencing reaction using the second generation Illumina system (e.g. NextSeq 500) can yield ~150 millions of sequence reads, so multiple samples from different grafts were barcoded, mixed and sequenced together, thus greatly reducing sequencing costs.

The sequencing data was de-barcoded and then analyzed by bioinformatics analysis. Established analysis tools such as HiTSelect or MAGeCK were used for gRNA enrichment analysis. In sum, the ability to amplify, sequence and subclone gRNAs after in vivo selection allowed identification of genes whose suppression improved beta cell survival.

Data from a single recipient of CRISPR-targeted beta cells yielded a surprisingly small number of target genes. As expected with the high stringency selection, only 13 unique gRNAs that target 12 genes out of 22 60,000 gRNAs present in pre-implantation cells were identified. The number of times the gRNA was present in sequence (count), the frequency of the gRNA in the total reads, and the gene targeted by the gRNA are shown in Table 2. Two different gRNAs targeting Men1 were found in the screen. The target genes in Table 2 encode for mouse SEQ ID Nos: 11-22 in Table 1, and the known human equivalents of these gene products are SEQ ID Nos: 1-10 in Table 1.

TABLE 2

Unique gRNAs identified

| Target gene | SEQ IDs | gRNA sequence | Count | Frequency (% of total reads) | Target gene product | Gene product class |
|---|---|---|---|---|---|---|
| Men1 | 23 | CACGCCCGAGCTGTCCAGTT | 4919 | 16.34 | Menin 1 | Known beta cell gene |
| Hivep2 | 24 | TACGCACTCATACTGATGTT | 4073 | 13.53 | human immunodeficiency virus type I enhancer binding protein 2 | Transcriptional repressor |

TABLE 2-continued

Unique gRNAs identified

| Target gene | SEQ IDs | gRNA sequence | Count | Frequency (% of total reads) | Target gene product | Gene product class |
|---|---|---|---|---|---|---|
| Rnls | 25 | CTACTCCTCTCGCTATGCTC | 3810 | 12.66 | renalase, FAD dependent amine oxidase | T1D GWAS gene, strongly associated with T1D only |
| Lgsn | 26 | TGCAACCGCGAACCCTTACC | 3252 | 10.80 | lengsin, lens protein with glutamine synthetase domain | Structural protein |
| GCN1 (Gcn1l1) | 27 | GCTTGACACTGCATCGATAT | 3228 | 10.72 | GCN1 general control of amino-acid synthesis 1-like 1 (yeast) | Transcriptional regulator |
| Gm3604 | 28 | ACTTTCGTATACAGATACTG | 3226 | 10.72 | unknown | Unannotated gene, predicted to be a transcriptional repressor |
| Plin4 | 29 | CTGCCTCCTTAGTTCCGACA | 2529 | 8.40 | perilipin 4 | Associated with lipid metabolism |
| Med11 | 30 | TTTCACGCTCGATATCCTCC | 1346 | 4.47 | mediator complex subunit 11 | Transcriptional regulator |
| Tgm6 | 31 | CATCGGTGGCTGGGTCCTCC | 1225 | 4.07 | trans-glutaminase 6 | Enzyme |
| Zbed3 | 32 | GCGCGAGGCGGCCCTAATGC | 1160 | 3.85 | zinc finger BED-type containing 3 | Possible transcriptional regulator, T2D GWAS gene |
| Men1 | 33 | GCTGTATGACCTCGGACATC | 702 | 2.33 | Menin 1 | Known beta cell gene |
| Olfr911-ps1 | 34 | CTTCAAATGAGATCCACTGC | 503 | 1.67 | olfactory receptor 911, pseudogene 1 (olfactory receptor 909) | GPCR |
| Grm2 | 35 | GCGGCATAACGCCACACCCG | 131 | 0.44 | glutamate receptor, metabotropic 2 | GPCR |

(GPCR = G-protein coupled receptor;
GWAS = genome-wide association study;
T1D = type 1 diabetes mellitus;
T2D = type 2 diabetes mellitus)

As shown in Table 3, ten of the mouse genes targeted by gRNAs in the LOF screen had a known human homolog.

TABLE 3

Mouse genes identified in LOF screen with human homolog

| Mouse gene symbol | Human gene symbol | Human gene ID |
|---|---|---|
| Men1 | MEN1 | 4221 |
| Hivep2 | HIVEP2 | 3097 |
| Rnls | RNLS | 55328 |
| Lgsn | LGSN | 51557 |
| Gcn1l1 | GCN1 | 10985 |
| Plin4 | PLIN4 | 729359 |
| Med11 | MED11 | 400569 |
| Tgm6 | TGM6 | 343641 |
| Zbed3 | ZBED3 | 84327 |
| Grm2 | GRM2 | 2912 |

Several of these selected gRNAs were enriched over 6000 times (>12% in the remaining transplanted cells) in the surviving graft. With the experimental set-up, any given gRNA is initially expected to infect only ~150 cells. Because not every cell carries homozygous mutations, the selected gRNAs are likely to have conferred strong protection even when causing only partial loss of function.

Notably, two of the top gRNA hits target the same Men1 that had previously been implicated in beta cell biology, though not in the context of autoimmunity. This result provides strong evidence that our approach yields highly relevant targets.

Strikingly, the third most enriched gRNA targets the gene Rnls that is a lead candidate for a type 1 diabetes-associated region identified by genome wide association study (GWAS). The Rnls gene has been suggested to associate with the progression rate to overt type 1 diabetes, but how Rnls is involved in pathogenesis is unknown. The fact that the Rnls gene is associated with type 1 diabetes but with no other autoimmune disease indicates that it probably has a non-immune role, likely altering beta cell survival or function.

Interestingly, another one of the 12 targets identified in this preliminary screen is a candidate gene for a type 2 diabetes-associated region (Zbed3). This particular gene had been suggested to participate in insulin secretion. Again, this provides suggestive evidence that this gene's role in type 2 diabetes stems for a key function in beta cell biology.

The remaining candidate genes identified have no clear link with diabetes based on current knowledge. One of these genes has not even been annotated previously (Gm3604), let alone studied. The fact that this screen was able to discover genes that were already associated with type 1 and 2 diabetes or that are known to impact beta cell biology highlights the power of this unbiased yet stringent screening strategy.

Example 2

Confirmation of Candidate Genes

Figure 5A:
FIGS. 5A-5C show confirmation that the gRNAs used in the screen induced editing of the target gene.
Figure 5B:
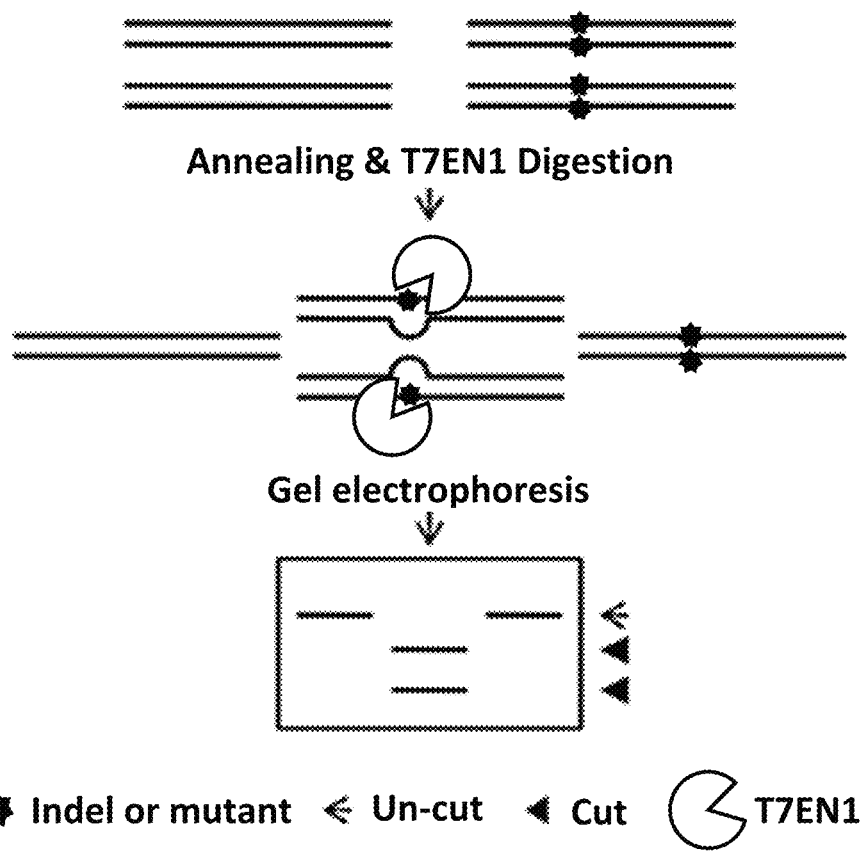
Figure 5C:
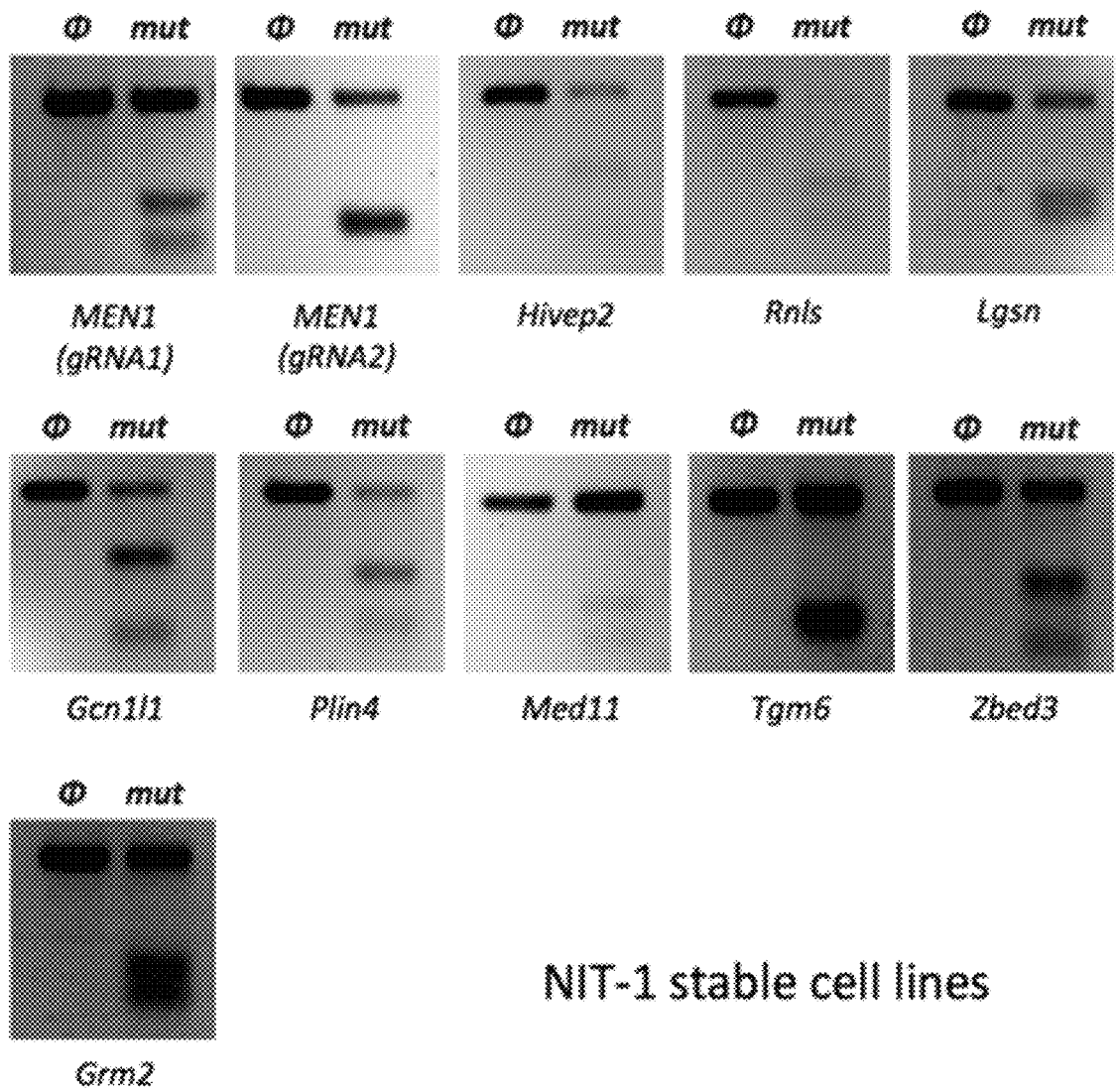

In vitro experiments were performed to confirm the in vivo screen results that inhibition of the genes listed in Table 2 promoted survival of beta cells in a type 1 diabetes model. NIT-1 stable cell lines were prepared for each candidate gene to investigate whether the gRNA used mediated editing of the target gene. To generate NIT-1 stable cell lines, the Cas9 gene and single gRNA targeting each candidate gene were stably incorporated into the genome of NIT-1 cells by lentivirus transduction. The T7E1 assay was used to detect mutations in the target genome locus, with activity based on the capability of T7 endonuclease I to cut mismatched double strand DNA. This strategy means that not all cells will have the homozygous null/missense mutation; therefore, a relative decrease (without total loss of native form) indicates successful editing of the target gene. Data shown in FIGS. 5A-5C shows editing experiments in stable cells lines. FIG. 5A shows the primer locations outside of the targeting site of the gRNA, and FIG. 5B shows the T7E1 assay design. Table 4 provides primers used for the T7E1 experiments.

TABLE 4

Genome PCR primers used for T7E1 assay

| Gene | SEQ ID No: | 5' primer | SEQ ID No: | 3' primer |
|---|---|---|---|---|
| Hivep2 | 36 | TCACAGTGGTC TGCCTCTTC | 49 | TGAAACCTTTC CCTCTCCAA |
| Rnls | 37 | TGGGACTTGTT TAAAGGAGCTT | 50 | TTGCGCTTCTT ATTATCAATGG |
| Lgsn | 38 | GCAGAGACCTG AAGGACAGC | 51 | CAAAGGGATCT CGGAAGGTT |
| Gcn1l1 | 39 | GGCTTACTAGG GCGTCTGGT | 52 | ACTAGGGGCTC TCCCCACT |
| Gm3604 | 40 | GTAACTGGATT GGCCCAAGA | 53 | TGTGGTAAAGC TTGTGTGTGG |
| Plin4 | 41 | GTTTGCAGCTC CCATGACTC | 54 | CAGTGTGACCA GCAGTGAAGA |
| Med11 | 42 | ACTCAGCCCCG CCCTAAG | 55 | CGCACATTAAC AGGCATTTC |
| Tgm6 | 43 | ACTGGTTTGGG GGATCCTT | 56 | AACAGATCAAG TGGGGTTGG |
| Zbed3 | 44 | GAGCTCGCCGA CCACCAT | 57 | TCAGTGCTTCA CGCTCTACC |
| Olfr909 | 45 | TTTTCCCTCTG TTGCAGCTC | 58 | AGGTGAGGAGG GCTGAAGAT |
| Grm2 | 46 | TGACTGGATGC TTTGAGCTG | 59 | CGCCTTAAGGT GCAGACG |
| Men1 (locus 1) | 47 | CCACGTCACCT CAGCTGTCT | 60 | AGTGGATAGGG TGTGTGATGC |
| Men1 (locus 2) | 48 | CAGGTCTGCCA AGTTCCCTA | 61 | CTCCTAGCCCT TCTGTGGTG |

As shown in FIG. 5C, successful editing was seen for all target genes in vitro using the gRNAs found during the in vivo screen. These data confirm that the gRNAs identified in the in vivo screen can successfully edit their target gene.

Figure 6A:
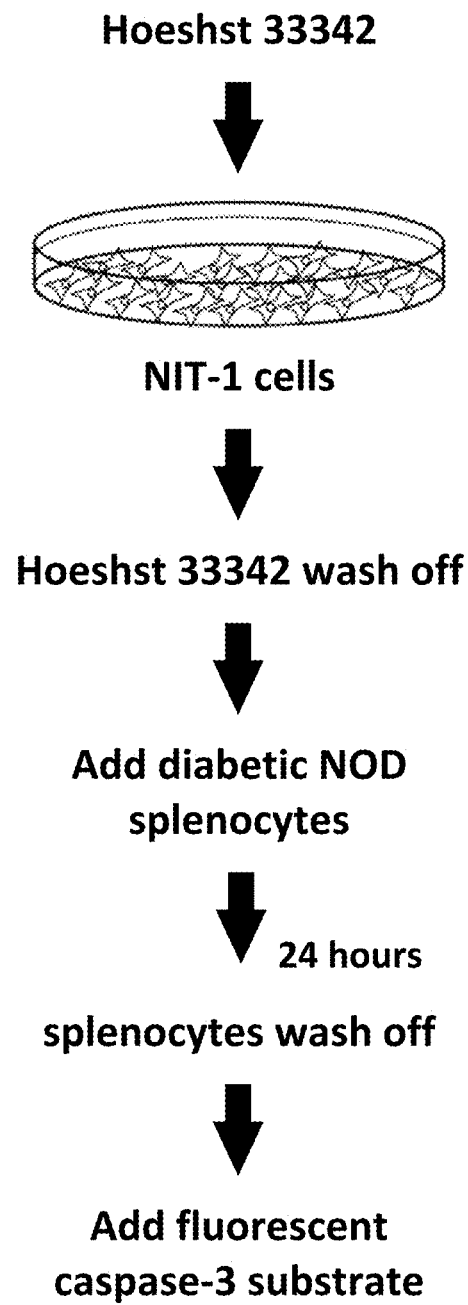
FIGS. 6A-6C show are in vitro co-culture system for studying NIT-1 cell death by NOD splenocytes.
Figure 6B:
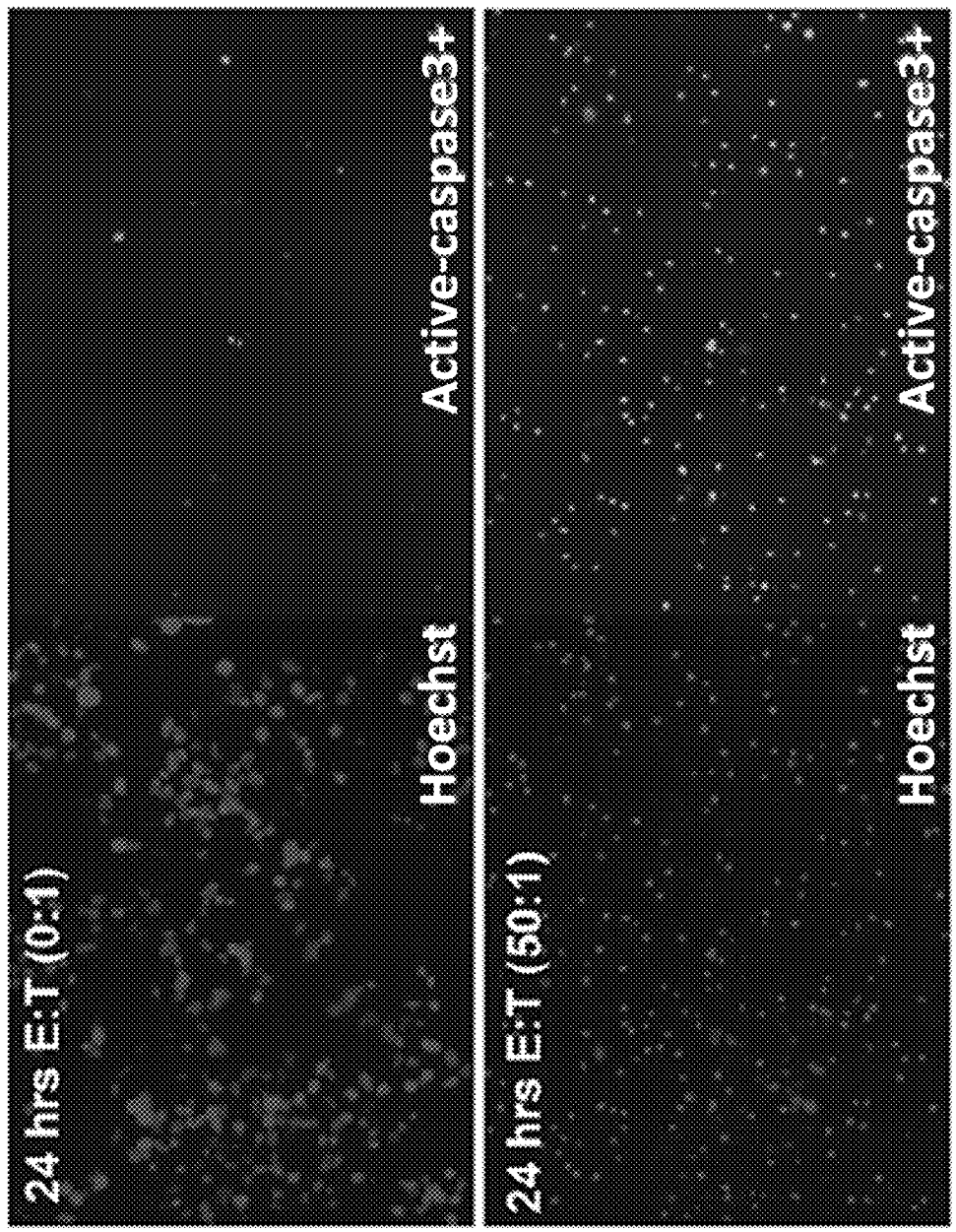
Figure 6C:
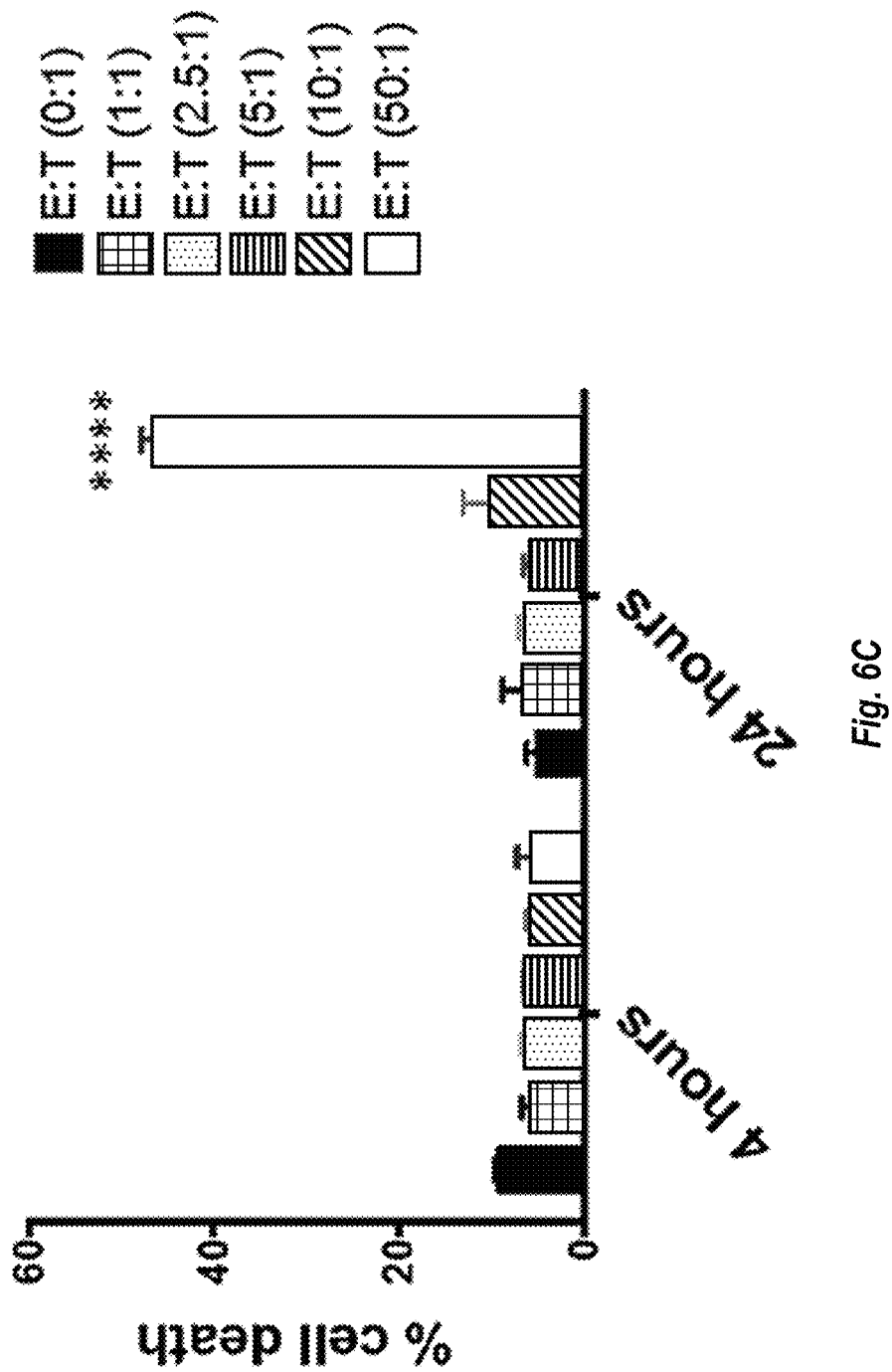

A cellular model of immune killing of stable NIT-1 cell lines was also developed, as shown in FIGS. 6A-6C. As shown in FIG. 6A, a co-culture assay with NIT-1 cells and NOD splenocytes was developed, wherein NIT-1 cells can be co-cultured with different ratios of NOD splenocytes (FIG. 6B). There is little cell death over 24 hours of NIT-1 cells not co-cultured with NOD splenocytes (0:1 ratio of splenocytes to NIT-1 cells in FIG. 6B), as evidenced by weak staining of active caspase-3. In contrast, NIT-1 cells co-cultured with a high ratio of NOD splenocytes (50:1 ratio of splenocytes to NIT-1 cells in FIG. 6B) show high cell death, as evidenced by strong caspase-3 activity. These data are summarized in FIG. 6C, which shows that 24 hour co-culture with a 50:1 ratio of NOD splenocytes:NIT-1 cells lead to a high percentage of cell death. This model can be used to study whether inhibiting or suppressing expression of target genes blocks or inhibits the ability of NOD splenocytes to mediate NIT-1 cell death over time.

Figure 7:
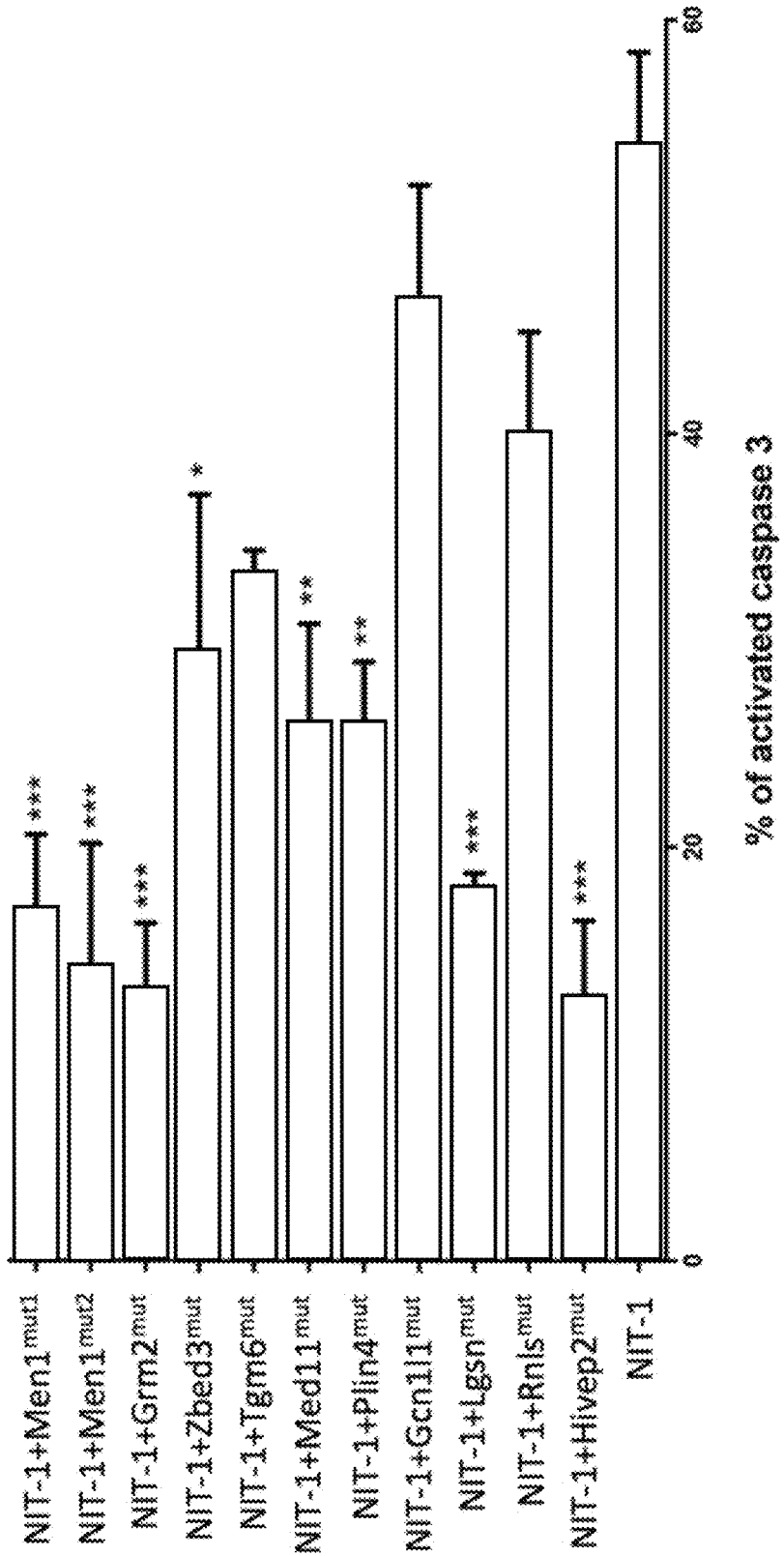
FIG. 7 shows results on activation of caspase 3 in a co-culture system of NOD splenocytes incubated with NIT-1 cells expressing gRNAs for different target genes. NIT-1 cells were incubated for 24 hours with splenocytes at a ratio of 50 splenocytes:1 NIT-1 cell. $P<0.05$=*; $P<0.01$=, and $P<0.001$=*.

FIG. 7 shows killing of NIT-1 cells by NOD splenocytes (measured by activated caspase 3) for NIT-1 cell lines stably expressing gRNAs to inhibit expression of various target genes. While more than 50% of NIT-1 cells without any inhibition of a target gene showed activated caspase 3 staining ("NIT1" group), expression of gRNAs to inhibit many of the target genes significantly decreased caspase 3 activation. For example, both gRNAs targeting menin (SEQ ID No: 23 and SEQ ID No: 33) significantly decreased NIT-1 cell death mediated by NOD splenocytes.

Example 3

Reduction in Endoplasmic Reticulum Stress by Inhibition of Expression of Ruts or Zbed3 in Beta Cells In some instances, beta cell death in Type 1 diabetes is induced by endoplasmic reticulum (ER) stress. Blocking ER stress and subsequent beta cell death has been shown to reverse early-onset Type 1 diabetes in mouse models (see Morita S. et al. *Cell Metabolism* 2017; 25(4):883-897). Therefore, one way to assess whether a therapeutic intervention is capable of protecting beta cells from autoimmune destruction is to assess whether that therapeutic can protect beta cells from death caused by ER stress.

NIT-1 beta cells were genetically modified at two genes— 1) Rnls; and 2) Zbed3 with CRISPR/Cas9 and guide RNAs (gRNAs) targeting Rnls and Zbed3, respectively. The modified NIT-1 cells had reduced expression of renalase (Rnls mutants) or zinc finger BED domain-containing protein 3 (Zbed3 mutants). ER stress was induced by thapsigargin, which blocks the sarco/endoplasmic reticulum $Ca^{2+}$-ATPase (SERCA) pump on the ER, thus depleting calcium from the ER and leading to misfolding of proteins in ER and eventually ER stress induced cell death.

Figure 8:
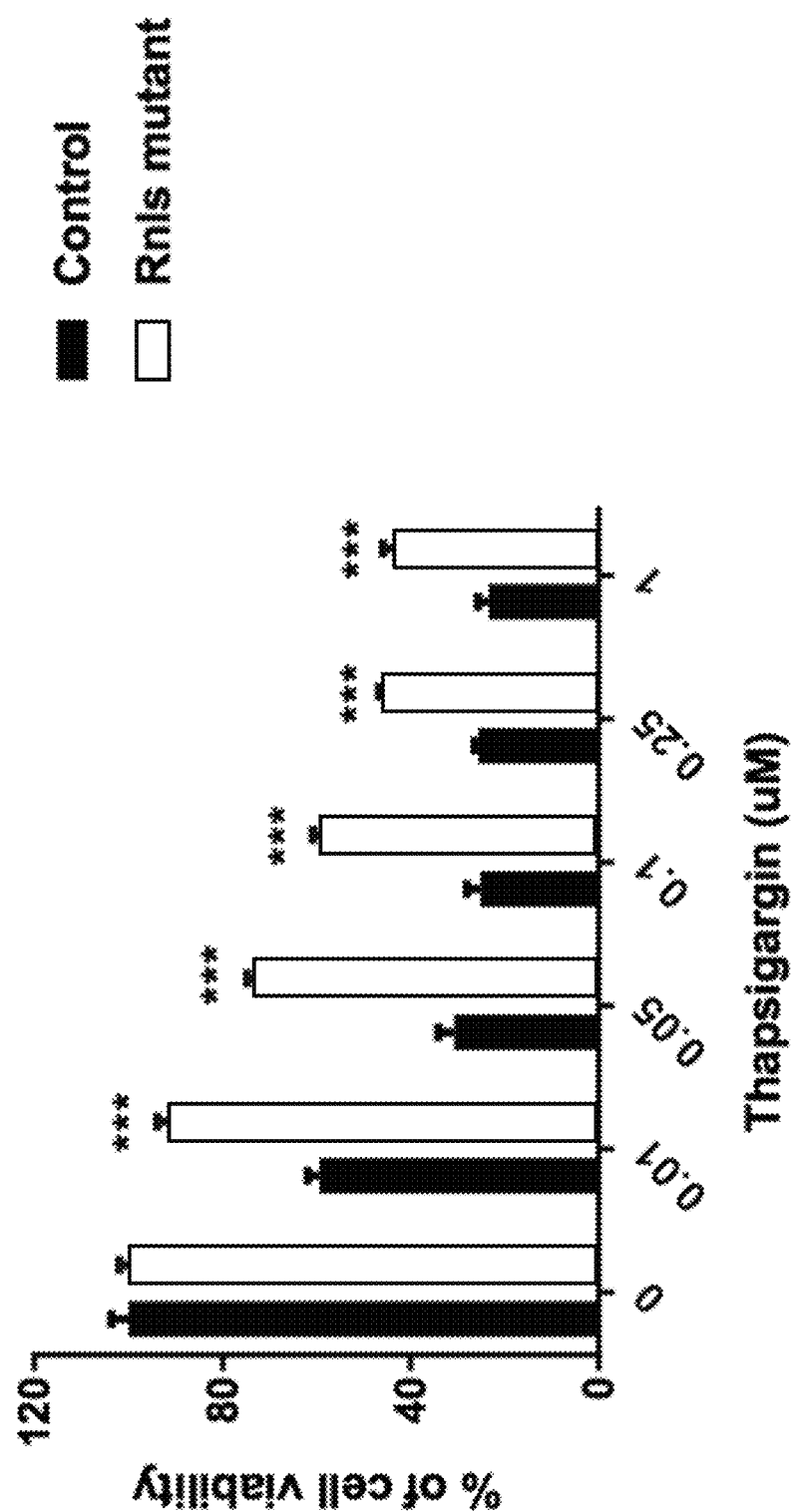
FIG. 8 shows cell viability of control or Rnls mutant NIT-1 cells following thapsigargin treatment.
Figure 9:
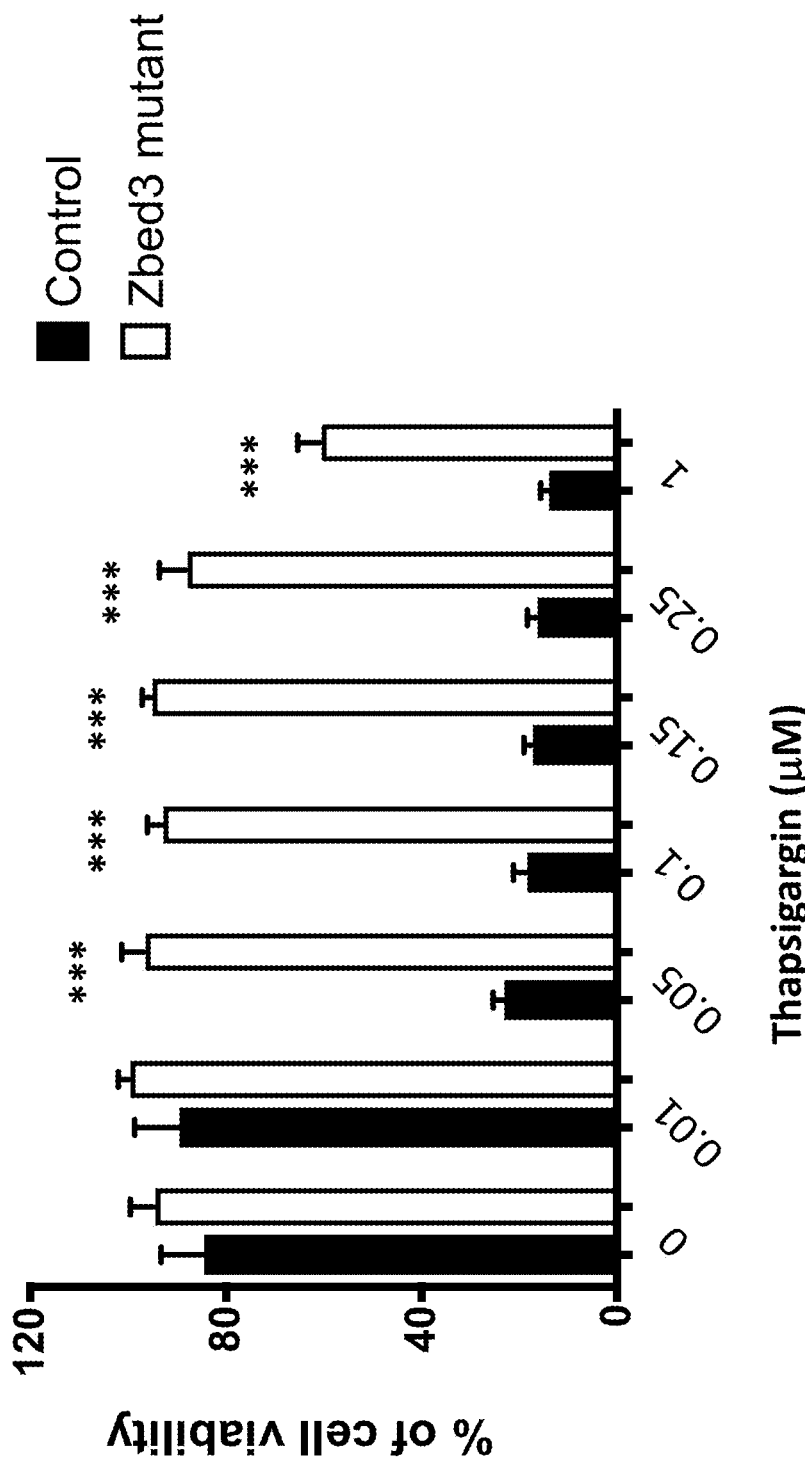
FIG. 9 shows cell viability of control or Zbed3 mutant NIT-1 cells following thapsigargin treatment.

All cells were treated with thapsigargin for 3 days, and cell viability was evaluated by a standard MTT assay (see Mosmann T, *J. Immunol Methods* 65(1-2):55-63 (1983)). Our studies showed that thapsigargin at different dosages induced beta cell death in control cells. However, in Rnls mutant and Zbed3 mutant cells were both resistant to thapsigargin-induced cell death in a dosage-dependent manner. Thus, inhibiting expression of the Rnls or Zbed3 protected beta cells from cell death induced by ER stress. See FIG. 8 (Rnls) and FIG. 9 (Zbed3).

Equivalents

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

---

What is claimed is:

1. A composition comprising (1) a cell capable of producing insulin in response to glucose and (2) a CRISPR/Cas9 system, zinc-finger nuclease, transcription activator-like effector nuclease (TALEN), meganuclease, or group one intron encoded endonuclease (GIIEE) capable of genetically modifying the coding region of a gene encoding renalase to inhibit expression of renalase, wherein the cell is:
   (a) a beta cell;
   (b) a cell generated from a stem cell; or
   (c) a reprogrammed or transdifferentiated pancreatic alpha cell, pancreatic exocrine cell, or a gut or stomach cell.

2. The composition of claim 1, further comprising a CRISPR/Cas9 system, zinc-finger nuclease, TALEN, meganuclease, or GIIEE capable of genetically modifying:

a. the coding region of a gene encoding menin to inhibit expression of menin, b. the coding region of a gene encoding transcription factor HIVEP2 to inhibit expression of HIVEP2, c. the coding region of a gene encoding lengsin to inhibit expression of lengsin, d. the coding region of a gene encoding eIF-2-alpha kinase activator GCN1 to inhibit expression of eIF-2-alpha kinase activator GCN1, e. the coding region of a gene encoding perilipin-4 to inhibit expression of perilipin-4, f. the coding region of a gene encoding mediator of RNA polymerase II transcription subunit 11, to inhibit expression of mediator of RNA polymerase II transcription subunit 11, g. the coding region of a gene encoding protein-glutamine gamma-glutamyltransferase 6 to inhibit expression of protein-glutamine gamma -glutamyltransferase 6, h. the coding region of a gene encoding zinc finger BED domain-containing protein 3 to inhibit expression of zinc finger BED domain-containing protein 3, or i. the coding region of a gene encoding metabotropic glutamate receptor 2 to inhibit expression of metabotropic glutamate receptor 2.

3. The composition of claim 1, wherein the cell is isolated from a human, non-human primate, cow, horse, pig, sheep, goat, dog, cat, or rodent.

4. The composition of claim 1, wherein the stem cell is an adult stem cell, pluripotent stem cell, embryonic stem cell, hematopoietic stem cell, bone marrow stromal stem cell, or mesenchymal stem cell.

5. The composition of claim 1, wherein the CRISPR/Cas9 system, zinc-finger nuclease, TALEN, meganuclease, or GIIEE is capable of generating a substitution, insertion, deletion, or excision of one or more nucleotides.

6. The composition of claim 1, wherein the composition comprises a CRISPR/Cas9 system and further comprises a guide RNA comprising SEQ ID NO: 25.

7. The composition of claim 1, wherein renalase comprises a sequence comprising SEQ ID NO: 3.

8. The composition of claim 2, wherein menin comprises a sequence comprising SEQ ID No: 1, transcription factor HIVEP2 comprises a sequence comprising SEQ ID No: 2, lengsin comprises a sequence comprising SEQ ID No: 4, eIF-2-alpha kinase activator GCN1 comprises a sequence comprising SEQ ID No: 5, perilipin-4 comprises a sequence comprising SEQ ID No: 6, mediator of RNA polymerase II transcription subunit 11 comprises a sequence comprising SEQ ID No: 7, protein-glutamine gamma-glutamyltransferase 6 comprises a sequence comprising SEQ ID No: 8, zinc finger BED domain-containing protein 3 comprises a sequence comprising SEQ ID No: 9, and metabotropic glutamate receptor 2 comprises a sequence comprising SEQ ID No: 10.

9. The composition of claim 1, wherein the genetically modified cell is protected from autoimmune destruction.

* * * * *

UNITED STATES PATENT AND TRADEMARK OFFICE
CERTIFICATE OF CORRECTION

| | |
|---|---|
| PATENT NO. | : 11,708,561 B2 |
| APPLICATION NO. | : 16/542721 |
| DATED | : July 25, 2023 |
| INVENTOR(S) | : Kissler et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 671 days.

Signed and Sealed this
Twelfth Day of November, 2024

Katherine Kelly Vidal
*Director of the United States Patent and Trademark Office*